US010494642B2

(12) United States Patent
Denolf et al.

(10) Patent No.: US 10,494,642 B2
(45) Date of Patent: Dec. 3, 2019

(54) *BRASSICA* PLANTS WITH MODIFIED SEED OIL COMPOSITION

(71) Applicant: BAYER CROPSCIENCE NV, Diegem (BE)

(72) Inventors: Peter Denolf, Velzeke (BE); Benjamin Laga, Wingene (BE)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 0 days.

(21) Appl. No.: 15/570,153

(22) PCT Filed: Apr. 28, 2016

(86) PCT No.: PCT/EP2016/059460
§ 371 (c)(1),
(2) Date: Oct. 27, 2017

(87) PCT Pub. No.: WO2016/174119
PCT Pub. Date: Nov. 3, 2016

(65) Prior Publication Data
US 2019/0024106 A1  Jan. 24, 2019

(30) Foreign Application Priority Data

Apr. 28, 2015 (EP) ..................................... 15165478

(51) Int. Cl.
*A01H 5/10*  (2018.01)
*A01H 1/00*  (2006.01)
*C12N 15/82*  (2006.01)
*A01H 6/20*  (2018.01)
*C07K 14/415*  (2006.01)

(52) U.S. Cl.
CPC ........... *C12N 15/8261* (2013.01); *A01H 5/10* (2013.01); *A01H 6/202* (2018.05); *C07K 14/415* (2013.01); *C12N 15/8247* (2013.01); *C12Y 114/19006* (2013.01)

(58) Field of Classification Search
None
See application file for complete search history.

(56) References Cited

U.S. PATENT DOCUMENTS

| | | |
|---|---|---|
| 5,491,288 A | 2/1996 | Chaubet et al. |
| 5,510,471 A | 4/1996 | Lebrun et al. |
| 5,633,448 A | 5/1997 | Lebrun et al. |
| 5,792,930 A | 8/1998 | Chaubet et al. |
| 5,985,557 A | 11/1999 | Prudent et al. |
| 6,001,567 A | 12/1999 | Brow et al. |
| 2006/0137040 A1 | 6/2006 | Debonte et al. |
| 2013/0298279 A1 | 11/2013 | Gingera et al. |

FOREIGN PATENT DOCUMENTS

| | | |
|---|---|---|
| CA | 2619858 A1 | 8/2009 |
| EP | 0242236 A1 | 10/1987 |
| EP | 0242246 A1 | 10/1987 |
| EP | 0507698 A1 | 10/1992 |
| EP | 0508909 A1 | 10/1992 |
| EP | 0534858 A1 | 3/1993 |
| WO | WO 94/11516 A1 | 5/1994 |
| WO | WO 97/21340 A1 | 6/1997 |
| WO | WO 98/56239 A1 | 12/1998 |
| WO | WO 2006/079567 A2 | 8/2006 |
| WO | WO 2006/105946 A2 | 10/2006 |
| WO | WO 2007/107590 A2 | 9/2007 |
| WO | WO 2007/138444 A2 | 12/2007 |
| WO | WO 2008/084107 A1 | 7/2008 |
| WO | WO 2009/002150 A1 | 12/2008 |
| WO | WO 2009/007091 A2 | 1/2009 |
| WO | WO 2007/099459 A2 | 9/2009 |
| WO | WO 2011/060946 A1 | 5/2011 |
| WO | WO 2012/117256 A2 | 9/2012 |
| WO | WO 2013/049356 A2 | 4/2013 |
| WO | WO 2013/112523 A2 | 8/2013 |
| WO | WO 2014/039692 A2 | 3/2014 |

OTHER PUBLICATIONS

GenBank Locus Tag: AT3G12120, FAD2 fatty acid desaturase 2 [*Arabidopsis thaliana* (thale cress) ], last updated date Jul. 9, 2017 (6 pages).
Azpiroz-Leehan et al., "T-DNA insertion mutagenesis in *Arabidopsis*: going back and forth," 1997, TIG, vol. 13, pp. 152-156.
Broun et al., "Genetic Engineering of Plant Lipids," 1999, Annu. Rev. Nutr., vol. 19, pp. 197-216.
Browse et al., "Glycerolipid Synthesis: Biochemistry and Regulation1" 1991, Annu. Rev. Plant Physiol. Plant Mol. Biol., vol. 42, pp. 467-506.
Chen et al., "Obtaining new germplast of *Brassica napus* with high oleic acid content by RNA interference and marker-free transofmration of Fad2 gene," 2006, J. Plant Physiol. Mol. Biol., vol. 32, pp. 665 (Abstract only).
Doyle et al., "A rapid DNA isolation procedure for small quantities of fresh leaf tissue," 1987, Phytochemistry Bulletin, vol. 19, 1 page (Abstract only).
Gunstone, "Movements Towards Tailor-Made Fats," Prog. Lipid Res., vol. 37, pp. 277-305, 1998.
Henikoff et al., "Tilling. Traditional Mutagenesis Meets Functional Genomics," 2004, Plant Physiology, vol. 135(2) pp. 630-636.
Jaworski et al., "Industrial oils from transgenic plants," 2003, Curr. Opin. Plant Biol., vol. 6, 178-184.
Li et al., "A fast neutron deletion mutagenesis-based reverse genetics system for plants," 2001, The Plant Journal, vol. 27, pp. 235-252.
Li et al., "Reverse genetics by fast neutron mutagenesis in higher plants," 2002, Funct. Integr. Genomics, vol. 2, pp. 254-258.

(Continued)

*Primary Examiner* — Phuong T Bui
(74) *Attorney, Agent, or Firm* — Arent Fox LLP

(57) ABSTRACT

The present invention relates to *Brassica* plants comprising mutant FAD2 genes, FAD2 nucleic acid sequences and proteins, as well as methods for generating and identifying said plants and alleles, which can be used to plants with increased levels of C18:1 in the seed oil. The invention further relates to combining the mutant FAD2 alleles with mutant FAD3 alleles to increase the levels of C18:1 and reduce the levels of C18:3 in the seed oil.

16 Claims, 3 Drawing Sheets

Specification includes a Sequence Listing.

(56) References Cited

OTHER PUBLICATIONS

Mccallum et al., "Targeted screenings of induced mutations," 2000, Nat. Biotechnol., vol. 18, pp. 455-457.

Mccallum et al., "Targeting Induced Local Lesions in Genomes (Tilling) for Plant Functional Genomics," 2000, Plant Physiol., 123: 439-442.

Mckenzie et al., "Tissue-culture enhanced transposition of the maize transposable element Dissociation in *Brassica oleracea* var. *italica*." 2002, Theor. Appl. Genet., vol. 105, pp. 23-33.

Miquel et al., "*Arabidopsis* Mutants Deficient in Polyunsaturated Fatty Acid Synthesis," 1992, J. Biol Chem., vol. 267, pp. 1502-1509.

Mortazavi et al., "Mapping and quantifying mammalian transcriptomes by RNA-Seq," 2008, Nature Methods, vol. 5(7), pp. 621-628.

Needleman et al., "A General Method Applicable to the Search for Similarities in the Amino Acid Sequence of Two Proteins," 1970, J. Mol. Biol., vol. 48(3), pp. 443-453.

Okuley et al., "*Arabidopsis* FAD2 Gene Encodes the Enzyme That is Essential for Polyunsaturated Lipid Synthesis," 1994, Plant Cell, vol. 6, pp. 147-158.

Peng et al., "Simultaneous silencing of FAD2 and FAE1 genes affects both oleic acid and erucic acid contents in *Brassica napus* seeds," 2010, Plant Cell Rep, vol. 29, pp. 317-325.

Peyou-Ndi et al., "Identification and Characterization of an Animal Delta12 Fatty Acid Desaturase Gene by Heterologous Expression," Archives of Biochemistry and Biophysics, vol. 376(2), 2000, pp. 399-408.

Rice et al., "EMBOSS: The European Molecular Biology Open Software Suite," Jun. 2000, TIG, vol. 16(6), pp. 276-277.

Stoutjesdijk et al., "High-oleic acid Australian *Brassica napus* and *B. juncea* varieties produced by co-suppression of endogenous Delta12-desaturases," 2000, Biotech. Soc. Trans., vol. 28, pp. 938-940.

Wells et al., "The control of seed oil polyunsaturated content in the polyploid crop species *Brassica napus*," 2014, Mol Breeding, vol. 33, pp. 349-362.

```
SEQ ID NO:  3    1 mgaggrmpvptsskksetdttkrvpcekppfsvgdlkkaipphcfkrsip
SEQ ID NO:  6    1 mgaggrmqvsppskksetdnikrvpcetppftvgelkkaipphcfkrsip
SEQ ID NO:  9    1 mgaggrmqvsppskksetdtikrvpcetppftvgelkkaipphcfkrsip
SEQ ID NO: 12    1 mgaggrmqvsppssspgtntlkrvpcetppftlgdlkkaipphcfkrsip
SEQ ID NO: 15    1 mgaggrmqispps sspetktlkrvpcetppftlgdlkkaipphcfkrsip
SEQ ID NO: 18    1 mgaggrmqvsppskksetdtikrvpcetppftvgelkkaipphcfkrsip
SEQ ID NO: 21    1 mgaggrmqvsppssspgtntlkrvpcetppftlgdlkkaipphcfkrsip
SEQ ID NO: 24    1 mgaggrmqvsppskksetdtikrvpcetppftvgelkkaipphcfkrsip
SEQ ID NO: 27    1 mgaggrmqvsppssspetktlkrvpcetppftlgdlkkaipphcfkrsip TM-1
SEQ ID NO:  3   51 rsfsylisdiiiascfyyvatnyfsllpqplsylawplywacqgcvltgi
SEQ ID NO:  6   51 rsfsyliwdiiiascfyyvattyfpllphplsyfawplywacqgcvltgv
SEQ ID NO:  9   51 rsfsyliwdiiiascfyyvattyfpllphplsyfawplywacqgcvltgv
SEQ ID NO: 12   51 rsfs---sstssspprllplpplhsllpsplprlt-pl------------
SEQ ID NO: 15   51 rsfsyllfdilvssslyhlstayfpllphplpylawplywacqgcvltgl
SEQ ID NO: 18   51 rsfsyliwdiiiascfyyvattyfpllphplsyfawplywacqgcvltgv
SEQ ID NO: 21   51 rsfs---sstssspprllplpplhsllpsplprlt-pl------------
SEQ ID NO: 24   51 rsfsyliwdiiiascfyyvattyfpllphplsyfawplywacqgcvltgv
SEQ ID NO: 27   51 rsfsyllfdilvssslyhlstayfpllphplpylawplywacqgcvltgl HIS-1          TM-2              HIS-2
SEQ ID NO:  3  101 wviahecghhafsdyqwlddtvglifhsfllvpyfswkyshrrhhsntgs
SEQ ID NO:  6  101 wviahecgHhafsdyqwlddtvglifhsfllvpyfswkyshrrhhsntgs
SEQ ID NO:  9  101 Wviahecghhafsdyqwlddtvglifhsfllvpyfswkyshrrhhsntgs
SEQ ID NO: 12   85 ------------------lgl-----------------------------
SEQ ID NO: 15  101 wviahecghhafsdhqwlddavglvfhsfllvpyfswkyshrrhhsntgs
SEQ ID NO: 18  101 wviahecghhafsdyqwlddtvglifhsfllvpyfswkyshrrhhsntgs
SEQ ID NO: 21   85 ------------------lgl-----------------------------
SEQ ID NO: 24  101 wviahecghhafsdyqwlddtvglifhsfllvpyfswkyshrrhhsntgs
SEQ ID NO: 27  101 wviahecghhafsdhqwlddavglvfhsfllvpyfswkyshrrhhsntgs TM-3
SEQ ID NO:  3  151 lerdevfvpkqksaikwygkylnnplg---rimmltvqfvlgwplylafn
SEQ ID NO:  6  151 lerdevfvpkkksdikwygkylnnplg---rtvmltvqftlgwplylafn
SEQ ID NO:  9  151 lerdevfvpkkksdikwygkylnnplg---rtvmltvqftlgwplylafn
SEQ ID NO: 12   88 --------prlrp---------ngplghsprvrpprlq------------
SEQ ID NO: 15  151 lerdevfvpkkksdikwygkylnnplg---rtvmltvqftlgWplylafn
SEQ ID NO: 18  151 lerdevfvpkkksdikwygkylnnplg---rtvmltvqftlgwplylafn
SEQ ID NO: 21   88 --------prlrp---------ngplghsprvrpprlq------------
SEQ ID NO: 24  151 lerdevfvpkkksdikwygkylnnplg---rtvmltvqftlgwplylafn
SEQ ID NO: 27  151 lerdevfvpkkksdikwygkylnnplg---rtvmltvqftlgwplylafn TM-3                                TM-4
SEQ ID NO:  3  198 vsgrpy-dg-fachffpnapiyndrerlqiylsdagilavcfglyryaaa
SEQ ID NO:  6  198 vsgrpy-dggfachfhpnapiyndrerlqiyisdagilavcyglyryaav
SEQ ID NO:  9  198 vsgrpy-dggfachfhpnapiyndrerlqiyisdagilavcyglfryaaa
SEQ ID NO: 12  109 ---rp--------------pvagrrrprl---------------------
SEQ ID NO: 15  198 vsgrpysdg-fachfhpnapiyndrerlqiyisdagvlsvcyglyryags
SEQ ID NO: 18  198 vsgrpy-dggfachfhpnapiyndrerlqiyisdagilavcyglyryaav
SEQ ID NO: 21  109 ---rp--------------pvagrrrprl---------------------
SEQ ID NO: 24  198 vsgrpy-dggfachfhpnapiyndrerlqiyisdagilavcyglfryaaa
SEQ ID NO: 27  198 vsgrpysdg-fachfhpnapiyndrerlqiyisdagvlsvcyglyryags Figure 1
```

```
                                  TM-5
SEQ ID NO: 3   246 qgmasmiclygvpllivnaflvlitylqhthpslphydssewdwlrgala
SEQ ID NO: 6   247 qgvasmvcfygvpllivngflvlitylqhthpslphydssewdwlrgala
SEQ ID NO: 9   247 qgvasmvcfygvpllivngflvlitylqhthpslphydssewdwlrgala
SEQ ID NO: 12  122 -----------pllpprpvlll----evhp--------------------
SEQ ID NO: 15  247 rgvasmvcvygvplmivncflvlitylqhthpslphydssewdwlrgala
SEQ ID NO: 18  247 qgvasmvcfygvpllivngflvlitylqhthpslphydssewdwlrgala
SEQ ID NO: 21  122 -----------pllpprpvlll----evhp--------------------
SEQ ID NO: 24  247 qgvasmvcfygvpllivngflvlitylqhthpslphydssewdwlrgala
SEQ ID NO: 27  247 rgvasmvcvygvplmivncflvlitylqhthpslphy------ilrsgig HIS-3
SEQ ID NO: 3   296 tvdrdygilnkvfhnitdthvahhlfstmphynameatkaikpilgdyyq
SEQ ID NO: 6   297 tvdrdygilnkvfhnitdthvahhlfstmphyhameatkaikpilgeyyq
SEQ ID NO: 9   297 tvdrdygilnkvfhnitdthvahhlfstmphyhameatkaikpilgeyyq
SEQ ID NO: 12  ---------------------------------------------------
SEQ ID NO: 15  297 tvdrdygilnkvfhnitdthvahhlfstmphynameatkaikpilgeyyq
SEQ ID NO: 18  297 tvdrdygilnkvfhnitdthvahhlfstmphyhameatkaikpilgeyyq
SEQ ID NO: 21  ---------------------------------------------------
SEQ ID NO: 24  297 tvdrdygilnkvfhnitdthvahhlfstmphyhameatkaikpilgeyyq
SEQ ID NO: 27  ---------------------------------------------------

ER
SEQ ID NO: 3   346 fdgtpwyvamyreakeciyvepdregdkkgvywynnkl
SEQ ID NO: 6   347 fdgtpvvkamwreakeciyvepdrqgekkgvfwynnkl
SEQ ID NO: 9   347 fdgtpvvkamwreakeciyvepdrqgekkgvfwynnkl
SEQ ID NO: 12  --------------------------------------
SEQ ID NO: 15  347 fdgtpvvkamwreakeciyvepdrqgekkgvfwynnkl
SEQ ID NO: 18  347 fdgtpvvkamwreakeciyvepdrqgekkgvfwynnkl
SEQ ID NO: 21  --------------------------------------
SEQ ID NO: 24  347 fdgtpvvkamwreakeciyvepdrqgekkgvfwynnkl
SEQ ID NO: 27  --------------------------------------
```

Figure 1, continued

SEQUENCE LISTING

<160> NUMBER OF SEQ ID NOS: 51

<210> SEQ ID NO 1
<211> LENGTH: 2766
<212> TYPE: DNA
<213> ORGANISM: Arabidopsis thaliana
<220> FEATURE:
<221> NAME/KEY: Intron
<222> LOCATION: (173)..(1303)

<400> SEQUENCE: 1
tctcttgcca ttccccatct gaccaccaga agaagagcca cacactcaca aattaaaaag      60
agagagagag agagagagac agagagagag agagattctg cggaggagct tcttcttcgt     120
agggtgttca tcgttattaa cgttatcgcc cctacgtcag ctccatctcc aggtccgtcg     180
cttctcttcc atttcttctc attttcgatt ttgattctta tttcttttcca gtagctcctg    240 ctctgtgaat ttctccgctc acgatagatc tgcttatact ccttacattc aaccttagat    300

```
ctggtctcga ttctctgttt ctctgttttt ttcttttggt cgagaatctg atgtttgttt      360
atgttctgtc accattaata ataatgaact ctctcattca tacaatgatt agtttctctc      420
gtctacaaaa cgatatgttg cattttcact tttcttcttt ttttctaaga tgatttgctt      480
tgaccaattt gtttagatct ttattttatt ttattttctg gtgggttggt ggaaattgaa      540
aaaaaaaaaa acagcataaa ttgttatttg ttaatgtatt cattttttgg ctatttgttc      600
tgggtaaaaa tctgcttcta ctattgaatc tttcctggat tttttactcc tattgggttt      660
ttatagtaaa aatacataat aaaaggaaaa caaagttttt atagattctc ttaaacccct      720
tacgataaaa gttggaatca aaataattca ggatcagatg ctctttgatt gattcagatg      780
cgattacagt tgcatggcaa attttctaga tccgtcgtca cattttattt tctgtttaaa      840
tatctaaatc tgatatatga tgtcgacaaa ttctggtggc ttatacatca cttcaactgt      900
tttcttttgg ctttgtttgt caacttggtt ttcaatacga tttgtgattt cgatcgctga      960 attttttaata caagcaaact gatgttaacc acaagcaaga gatgtgacct gccttattaa     1020
catcgtatta cttactacta gtcgtattct caacgcaatc gttttgtat ttctcacatt      1080 atgccgcttc tctactcttt attccttttg gtccacgcat tttctatttg tggcaatccc     1140
tttcacaacc tgatttccca ctttggatca tttgtctgaa gactctcttg aatcgttacc     1200
acttgtttct tgtgcatgct ctgttttta gaattaatga taaaactatt ccatagtctt     1260
gagttttcag cttgttgatt cttttgcttt tggttttctg cagaaacatg ggtgcaggtg     1320
gaagaatgcc ggttcctact tcttccaaga aatcggaaac cgacaccaca aagcgtgtgc     1380
cgtgcgagaa accgcctttc tcggtgggag atctgaagaa agcaatcccg ccgcattgtt     1440
tcaaacgctc aatccctcgc tctttctcct accttatcag tgacatcatt atagcctcat     1500
gcttctacta cgtcgccacc aattacttct ctctcctccc tcagcctctc tcttacttgg     1560
cttggccact ctattgggcc tgtcaaggct gtgtcctaac tggtatctgg gtcatagccc     1620
acgaatgcgg tcaccacgca ttcagcgact accaatggct ggatgacaca gttggtctta     1680
tcttccattc cttcctcctc gtcccttact tctcctggaa gtatagtcat cgccgtcacc     1740
attccaacac tggatccctc gaaagagatg aagtatttgt cccaaagcag aaatcagcaa     1800
tcaagtggta cgggaaatac ctcaacaacc ctcttggacg catcatgatg ttaaccgtcc     1860
agtttgtcct cgggtggccc ttgtacttag cctttaacgt ctctggcaga ccgtatgacg     1920
ggttcgcttg ccatttcttc cccaacgctc ccatctacaa tgaccgagaa cgcctccaga     1980
tatccctctc tgatgcgggt attctagccg tctgttttgg tctttaccgt tacgctgctg     2040
cacaagggat ggcctcgatg atctgcctct acggagtacc gcttctgata gtgaatgcgt     2100
tcctcgtctt gatcacttac ttgcagcaca ctcatccctc gttgcctcac tacgattcat     2160
cagagtggga ctggctcagg ggagctttgg ctaccgtaga cagagactac ggaatcttga     2220
acaaggtgtt ccacaacatt acagacacac acgtggctca tcacctgttc tcgacaatgc     2280
cgcattataa cgcaatggaa gctacaaagg cgataaagcc aattctggga gactattacc     2340
agttcgatgg aacaccgtgg tatgtagcga tgtatagga ggcaaaggag tgtatctatg     2400
tagaaccgga cagggaaggt gacaagaaag gtgtgtactg gtacaacaat aagttatgag     2460
gatgatggtg aagaaattgt cgacctttct cttgtctgtt tgtctttgt taaagaagct     2520 atgcttcgtt ttaataatct tattgtccat tttgttgtgt tatgacattt tggctgctca     2580
ttatgttatg tgggaagtta gtgttcaaat gttttgtgtc ggtattgttc ttctcatcgc     2640
```

```
tgttttgttg ggatcgtaga aatgtgacct tcggacagta aaactcttgt actaaaacta    2700
tctccctatt ggcatttctt aaactttaa  tagttacgtg ctcgtagtga atcttgactt    2760
gagtca                                                               2766
```

<210> SEQ ID NO 2
<211> LENGTH: 1635
<212> TYPE: DNA
<213> ORGANISM: Arabidopsis thaliana
<220> FEATURE:
<221> NAME/KEY: CDS
<222> LOCATION: (177)..(1328)

<400> SEQUENCE: 2

```
tctcttgcca ttccccatct gaccaccaga agaagagcca cacactcaca aattaaaaag     60
agagagagag agagagagac agagagagag agagattctg cggaggagct tcttcttcgt    120
agggtgttca tcgttattaa cgttatcgcc cctacgtcag ctccatctcc agaaac atg    179
                                                                Met
                                                                 1 ggt gca ggt gga aga atg ccg gtt cct act tct tcc aag aaa tcg gaa    227
Gly Ala Gly Gly Arg Met Pro Val Pro Thr Ser Ser Lys Lys Ser Glu
          5                  10                  15 acc gac acc aca aag cgt gtg ccg tgc gag aaa ccg cct ttc tcg gtg    275
Thr Asp Thr Thr Lys Arg Val Pro Cys Glu Lys Pro Pro Phe Ser Val
         20                  25                  30 gga gat ctg aag aaa gca atc ccg ccg cat tgt ttc aaa cgc tca atc    323
Gly Asp Leu Lys Lys Ala Ile Pro Pro His Cys Phe Lys Arg Ser Ile
     35                  40                  45 cct cgc tct ttc tcc tac ctt atc agt gac atc att ata gcc tca tgc    371
Pro Arg Ser Phe Ser Tyr Leu Ile Ser Asp Ile Ile Ile Ala Ser Cys
 50                  55                  60                  65 ttc tac tac gtc gcc acc aat tac ttc tct ctc ctc cct cag cct ctc    419
Phe Tyr Tyr Val Ala Thr Asn Tyr Phe Ser Leu Leu Pro Gln Pro Leu
                 70                  75                  80 tct tac ttg gct tgg cca ctc tat tgg gcc tgt caa ggc tgt gtc cta    467
Ser Tyr Leu Ala Trp Pro Leu Tyr Trp Ala Cys Gln Gly Cys Val Leu
             85                  90                  95 act ggt atc tgg gtc ata gcc cac gaa tgc ggt cac cac gca ttc agc    515
Thr Gly Ile Trp Val Ile Ala His Glu Cys Gly His His Ala Phe Ser
        100                 105                 110 gac tac caa tgg ctg gat gac aca gtt ggt ctt atc ttc cat tcc ttc    563
Asp Tyr Gln Trp Leu Asp Asp Thr Val Gly Leu Ile Phe His Ser Phe
    115                 120                 125 ctc ctc gtc cct tac ttc tcc tgg aag tat agt cat cgc cgt cac cat    611
Leu Leu Val Pro Tyr Phe Ser Trp Lys Tyr Ser His Arg Arg His His
130                 135                 140                 145 tcc aac act gga tcc ctc gaa aga gat gaa gta ttt gtc cca aag cag    659
Ser Asn Thr Gly Ser Leu Glu Arg Asp Glu Val Phe Val Pro Lys Gln
                150                 155                 160 aaa tca gca atc aag tgg tac ggg aaa tac ctc aac aac cct ctt gga    707
Lys Ser Ala Ile Lys Trp Tyr Gly Lys Tyr Leu Asn Asn Pro Leu Gly
            165                 170                 175 cgc atc atg atg tta acc gtc cag ttt gtc ctc ggg tgg ccc ttg tac    755
Arg Ile Met Met Leu Thr Val Gln Phe Val Leu Gly Trp Pro Leu Tyr
        180                 185                 190 tta gcc ttt aac gtc tct ggc aga ccg tat gac ggg ttc gct tgc cat    803
Leu Ala Phe Asn Val Ser Gly Arg Pro Tyr Asp Gly Phe Ala Cys His
    195                 200                 205 ttc ttc ccc aac gct ccc atc tac aat gac cga gaa cgc ctc cag ata    851
Phe Phe Pro Asn Ala Pro Ile Tyr Asn Asp Arg Glu Arg Leu Gln Ile
```

```
                    210                 215                 220                 225
tac ctc tct gat gcg ggt att cta gcc gtc tgt ttt ggt ctt tac cgt        899
Tyr Leu Ser Asp Ala Gly Ile Leu Ala Val Cys Phe Gly Leu Tyr Arg
                230                 235                 240 tac gct gct gca caa ggg atg gcc tcg atg atc tgc ctc tac gga gta        947
Tyr Ala Ala Ala Gln Gly Met Ala Ser Met Ile Cys Leu Tyr Gly Val
                    245                 250                 255 ccg ctt ctg ata gtg aat gcg ttc ctc gtc ttg atc act tac ttg cag        995
Pro Leu Leu Ile Val Asn Ala Phe Leu Val Leu Ile Thr Tyr Leu Gln
            260                 265                 270 cac act cat ccc tcg ttg cct cac tac gat tca tca gag tgg gac tgg       1043
His Thr His Pro Ser Leu Pro His Tyr Asp Ser Ser Glu Trp Asp Trp
        275                 280                 285 ctc agg gga gct ttg gct acc gta gac aga gac tac gga atc ttg aac       1091
Leu Arg Gly Ala Leu Ala Thr Val Asp Arg Asp Tyr Gly Ile Leu Asn
290                 295                 300                 305 aag gtg ttc cac aac att aca gac aca cac gtg gct cat cac ctg ttc       1139
Lys Val Phe His Asn Ile Thr Asp Thr His Val Ala His His Leu Phe
                310                 315                 320 tcg aca atg ccg cat tat aac gca atg gaa gct aca aag gcg ata aag       1187
Ser Thr Met Pro His Tyr Asn Ala Met Glu Ala Thr Lys Ala Ile Lys
            325                 330                 335 cca att ctg gga gac tat tac cag ttc gat gga aca ccg tgg tat gta       1235
Pro Ile Leu Gly Asp Tyr Tyr Gln Phe Asp Gly Thr Pro Trp Tyr Val
        340                 345                 350 gcg atg tat agg gag gca aag gag tgt atc tat gta gaa ccg gac agg       1283
Ala Met Tyr Arg Glu Ala Lys Glu Cys Ile Tyr Val Glu Pro Asp Arg
    355                 360                 365 gaa ggt gac aag aaa ggt gtg tac tgg tac aac aat aag tta tga           1328
Glu Gly Asp Lys Lys Gly Val Tyr Trp Tyr Asn Asn Lys Leu
370                 375                 380 ggatgatggt gaagaaattg tcgacctttc tcttgtctgt ttgtcttttg ttaaagaagc     1388
tatgcttcgt tttaataatc ttattgtcca ttttgttgtg ttatgacatt ttggctgctc     1448
attatgttat gtgggaagtt agtgttcaaa tgttttgtgt cggtattgtt cttctcatcg     1508
ctgttttgtt gggatcgtag aaatgtgacc ttcggacagt aaaactcttg tactaaaact     1568
atctccctat tggcatttct taaactttta atagttacgt gctcgtagtg aatcttgact     1628
tgagtca                                                                1635
```

<210> SEQ ID NO 3
<211> LENGTH: 383
<212> TYPE: PRT
<213> ORGANISM: Arabidopsis thaliana

<400> SEQUENCE: 3

```
Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
                20                  25                  30

Val Gly Asp Leu Lys Lys Ala Ile Pro Pro His Cys Phe Lys Arg Ser
            35                  40                  45

Ile Pro Arg Ser Phe Ser Tyr Leu Ile Ser Asp Ile Ile Ile Ala Ser
        50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95
```

```
Leu Thr Gly Ile Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380

<210> SEQ ID NO 4
<211> LENGTH: 3689
<212> TYPE: DNA
<213> ORGANISM: Brassica napus
<220> FEATURE:
<221> NAME/KEY: Intron
<222> LOCATION: (966)..(2042)
<220> FEATURE:
<221> NAME/KEY: mutation
<222> LOCATION: (2371)..(2371)
<223> OTHER INFORMATION: C to T in HIOL101

<400> SEQUENCE: 4
gtaacagctg aataaatgaa atgaaatcat ggtaggtgat gatctttaaa gaatgttaaa      60
aataatgtgt cgttataagc ggtaatgcat agaaaaactc taatcatctt aacataagag     120
agagcgatag ctttaataaa gtacttaaat taattactag tcggcagtcg ctgcctactt     180
gtgtaccacc taaattaatt tattataata tatgacgaat ctccaaagta catcacacac     240
actcggggct attcacgtga tctcaaccac aatgtctgca gatatttttt taagttttct     300
```

```
tctcacatgg gagaagaaga agccaagcac gatcctccat cctcaacttt atagcatttt    360
tttcttttct ttccggctac cactaacttc tacagttcta cttgtgagtc ggcaaggacg    420
tttcctcata ttaaagtaaa gacatcaaat accataatct taatgctaat taacgtaacg    480
gatgagttct ataacataac ccaaactagt ctttgtgaac attaggattg ggtaaaccaa    540
tatttacatt ttaaaaacaa aatacaaaaa gaaacgtgat aaactttata aaagcaatta    600
tatgatccac ggcatctttt tcactttttcc gtaaatatat ataagtggtg taaatatcag    660
atatttggag tagaaaaaaa aaaaagaaa aagaaatat gaagagagga aataatggag    720
gggcccactt gtaaaaaga aagaaaagag atgtcactca atcgtctcac acgggccccc    780
gtcaatttaa acggcctgcc ttctgcccaa tcgcatctta ccagaaccag agagattcat    840
taccaaagag atagagagag agagaaagag aggagacaga gagagagttt gaggaggagc    900
ttcttcgtag ggttcatcgt tattaacgtt aaatcttcat ccccccctac gtcagccagc    960
tcaaggtccc tttcttcttc catttcttct catttttacg ttgttttcaa tcttggtctg    1020
ttctttcttt atcgcttttc tattctatct atcatttttg catttcagtc gatttaattc    1080
tagatctgtt aatatttatt gcattaaact atagatctgg tcttgattct ctgttttcat    1140
gtgtgaaatc ttgatgctgt ctttaccatt aatctgatta tattgtctat accgtggaga    1200
atatgaaatg ttgcattttc atttgtccga atacaaactg tttgactttc aatctttttt    1260
aatgatttat tttgatgggt tggtggaggt gaaaaatcac catagcagtc tcacgtcctg    1320
gtcttagaaa tatccttcct attcaaagtt atatatattt gtttacttgt cttagatctg    1380
gacctgagac atgtaagtac ctatttgttg aatctttggg taaaaaactt atgtctctgg    1440
gtaaaatttg cttggagatt tgaccgattc ctattggctc ttgattctgt agttacctaa    1500
tacatgaaaa agtttcattt ggcctatgct cacttcatgc ttacaaactt ttctttgcaa    1560
attaattgga ttagatgctc cttcatagat tcagatgcaa tagatttgca tgaagaaaat    1620
aataggattc atgacagtaa aaaagattgt atttttgttt gtttgtttat gtttaaaagt    1680
ctatatgttg acaatagagt tgctctcaac tgtttcattt agcttttgt ttttgtcaag    1740 ttgcttattc ttagagacat tgtgattatg acttgtcttc tctaacgtag tttagtaata    1800
aaagacgaaa gaaattgata tccacaagaa agagatgtaa gctgtaacgt atcaaatctc    1860
attaataact agtagtattc tcaacgctat cgtttatttc tttctttggt ttgccactat    1920
atgccgcttc tctcctcttt tgtcccacgt actatccatt ttttgaaac tttaataacg    1980 taacactgaa tattaatttg ttggtttttt taactttgag tctttgcttt tggtttatgc    2040
agaaacatgg gtgcaggtgg aagaatgcaa gtgtctcctc cctccaaaaa gtctgaaacc    2100
gacaacatca agcgcgtacc ctgcgagaca ccgcccttca ctgtcggaga actcaagaaa    2160
gcaatcccac cgcactgttt caaacgctcg atccctcgct ctttctccta cctcatctgg    2220
gacatcatca tagcctcctg cttctactac gtcgccacca cttacttccc tctcctccct    2280 cacccctctct cctacttcgc ctggcctctc tactgggcct gccagggctg cgtcctaacc    2340
ggcgtctggg tcatagccca cgagtgcggc caccacgcct tcagcgacta ccagtggctg    2400
gacgacaccg tcggcctcat cttccactcc ttcctcctcg tcccttactt ctcctggaag    2460
tacagtcatc gacgccacca ttccaacact ggctccctcg agagagacga agtgtttgtc    2520
cccaagaaga agtcagacat caagtggtac ggcaagtacc tcaacaaccc tttgggacgc    2580
accgtgatgt taacggttca gttcactctc ggctggcctt tgtacttagc cttcaacgtc    2640
```

```
tcggggagac cttacgacgg cggcttcgct tgccatttcc accccaacgc tcccatctac    2700
aacgaccgtg agcgtctcca gatatacatc tccgacgctg gcatcctcgc cgtctgctac    2760
ggtctctacc gctacgctgc tgtccaagga gttgcctcga tggtctgctt ctacggagtt    2820
cctcttctga ttgtcaacgg gttcttagtt ttgatcactt acttgcagca cacgcatcct    2880
tccctgcctc actatgactc gtctgagtgg gattggttga ggggagcttt ggccaccgtt    2940
gacagagact acggaatctt gaacaaggtc ttccacaata tcacggacac gcacgtggcg    3000
catcacctgt tctcgaccat gccgcattat catgcgatgg aagctacgaa ggcgataaag    3060
ccgatactgg gagagtatta tcagttcgat gggacgccgg tggttaaggc gatgtggagg    3120
gaggcgaagg agtgtatcta tgtggaaccg gacaggcaag gtgagaagaa aggtgtgttc    3180
tggtacaaca ataagttatg aagcaaagaa gaaactgaac cttctcttc tatgattgtc    3240 tttgtttaag aagctatgtt tctgtttcaa taatcttaat tatccatttt gttgtgtttt    3300
ctgacatttt ggctaaaatt atgtgatgtt ggaagttagt gtctaaaatg tcttgtgtct    3360
gtattgttct tcttctcatc gctgttatgt ttgggatcgt tgaaatgtga ctttcggact    3420
agtgaactct tgttctcgaa ctatcttaat gtggatccct gaacagtgta atggcttagc    3480
ttcctctgaa actactatta tgttctagtg aatcttgaca taaagcaact tgtcgtttca    3540
agacatacca atgctttaag aaaaatgttt tactcacctg aagtgaacca taaatctaat    3600
cttcgttaca gttaagttag tttgagttat tgcgttgttt ggttggcaga tcacctttac    3660
tacttatgtg gttcagtctc tttgtaaaa                                      3689
```

<210> SEQ ID NO 5
<211> LENGTH: 1779
<212> TYPE: DNA
<213> ORGANISM: Brassica napus
<220> FEATURE:
<221> NAME/KEY: CDS
<222> LOCATION: (291)..(1445)
<220> FEATURE:
<221> NAME/KEY: mutation
<222> LOCATION: (615)..(615)
<223> OTHER INFORMATION: C to T in HIOL101

<400> SEQUENCE: 5

```
aaaaaaagaa aaaagaaata tgaagagagg aaataatgga ggggcccact tgtaaaaaag     60
aaagaaaaga gatgtcactc aatcgtctca cacgggcccc cgtcaattta acggcctgc    120 cttctgccca atcgcatctt accagaacca gagagattca ttaccaaaga gatagagaga    180
gagagaaaga gaggagacag agagagagtt tgaggaggag cttcttcgta gggttcatcg    240
ttattaacgt taaatcttca tccccccta cgtcagccag ctcaagaaac atg ggt       296
                                                        Met Gly
                                                          1 gca ggt gga aga atg caa gtg tct cct ccc tcc aaa aag tct gaa acc    344
Ala Gly Gly Arg Met Gln Val Ser Pro Pro Ser Lys Lys Ser Glu Thr
       5                  10                  15 gac aac atc aag cgc gta ccc tgc gag aca ccg ccc ttc act gtc gga    392
Asp Asn Ile Lys Arg Val Pro Cys Glu Thr Pro Pro Phe Thr Val Gly
 20                  25                  30 gaa ctc aag aaa gca atc cca ccg cac tgt ttc aaa cgc tcg atc cct    440
Glu Leu Lys Lys Ala Ile Pro Pro His Cys Phe Lys Arg Ser Ile Pro
 35                  40                  45                  50 cgc tct ttc tcc tac ctc atc tgg gac atc atc ata gcc tcc tgc ttc    488
Arg Ser Phe Ser Tyr Leu Ile Trp Asp Ile Ile Ile Ala Ser Cys Phe
             55                  60                  65
```

| | | | | | | | | | | | | | | | | |
|---|---|---|---|---|---|---|---|---|---|---|---|---|---|---|---|---|
| tac | tac | gtc | gcc | acc | act | tac | ttc | cct | ctc | ctc | cct | cac | cct | ctc | tcc | 536 |
| Tyr | Tyr | Val | Ala | Thr | Thr | Tyr | Phe | Pro | Leu | Leu | Pro | His | Pro | Leu | Ser | |
| | | | 70 | | | | 75 | | | | 80 | | | | | |
| tac | ttc | gcc | tgg | cct | ctc | tac | tgg | gcc | tgc | cag | ggc | tgc | gtc | cta | acc | 584 |
| Tyr | Phe | Ala | Trp | Pro | Leu | Tyr | Trp | Ala | Cys | Gln | Gly | Cys | Val | Leu | Thr | |
| | | 85 | | | | | 90 | | | | 95 | | | | | |
| ggc | gtc | tgg | gtc | ata | gcc | cac | gag | tgc | ggc | cac | cac | gcc | ttc | agc | gac | 632 |
| Gly | Val | Trp | Val | Ile | Ala | His | Glu | Cys | Gly | His | His | Ala | Phe | Ser | Asp | |
| 100 | | | | | 105 | | | | | 110 | | | | | | |
| tac | cag | tgg | ctg | gac | gac | acc | gtc | ggc | ctc | atc | ttc | cac | tcc | ttc | ctc | 680 |
| Tyr | Gln | Trp | Leu | Asp | Asp | Thr | Val | Gly | Leu | Ile | Phe | His | Ser | Phe | Leu | |
| 115 | | | | 120 | | | | | 125 | | | | | 130 | | |
| ctc | gtc | cct | tac | ttc | tcc | tgg | aag | tac | agt | cat | cga | cgc | cac | cat | tcc | 728 |
| Leu | Val | Pro | Tyr | Phe | Ser | Trp | Lys | Tyr | Ser | His | Arg | Arg | His | His | Ser | |
| | | | | 135 | | | | | 140 | | | | | 145 | | |
| aac | act | ggc | tcc | ctc | gag | aga | gac | gaa | gtg | ttt | gtc | ccc | aag | aag | aag | 776 |
| Asn | Thr | Gly | Ser | Leu | Glu | Arg | Asp | Glu | Val | Phe | Val | Pro | Lys | Lys | Lys | |
| | | | 150 | | | | | 155 | | | | | 160 | | | |
| tca | gac | atc | aag | tgg | tac | ggc | aag | tac | ctc | aac | aac | cct | ttg | gga | cgc | 824 |
| Ser | Asp | Ile | Lys | Trp | Tyr | Gly | Lys | Tyr | Leu | Asn | Asn | Pro | Leu | Gly | Arg | |
| | | | 165 | | | | | 170 | | | | | 175 | | | |
| acc | gtg | atg | tta | acg | gtt | cag | ttc | act | ctc | ggc | tgg | cct | ttg | tac | tta | 872 |
| Thr | Val | Met | Leu | Thr | Val | Gln | Phe | Thr | Leu | Gly | Trp | Pro | Leu | Tyr | Leu | |
| | 180 | | | | | 185 | | | | | 190 | | | | | |
| gcc | ttc | aac | gtc | tcg | ggg | aga | cct | tac | gac | ggc | ggc | ttc | gct | tgc | cat | 920 |
| Ala | Phe | Asn | Val | Ser | Gly | Arg | Pro | Tyr | Asp | Gly | Gly | Phe | Ala | Cys | His | |
| 195 | | | | | 200 | | | | | 205 | | | | | 210 | |
| ttc | cac | ccc | aac | gct | ccc | atc | tac | aac | gac | cgt | gag | cgt | ctc | cag | ata | 968 |
| Phe | His | Pro | Asn | Ala | Pro | Ile | Tyr | Asn | Asp | Arg | Glu | Arg | Leu | Gln | Ile | |
| | | | | 215 | | | | | 220 | | | | | 225 | | |
| tac | atc | tcc | gac | gct | ggc | atc | ctc | gcc | gtc | tgc | tac | ggt | ctc | tac | cgc | 1016 |
| Tyr | Ile | Ser | Asp | Ala | Gly | Ile | Leu | Ala | Val | Cys | Tyr | Gly | Leu | Tyr | Arg | |
| | | | 230 | | | | | 235 | | | | | 240 | | | |
| tac | gct | gct | gtc | caa | gga | gtt | gcc | tcg | atg | gtc | tgc | ttc | tac | gga | gtt | 1064 |
| Tyr | Ala | Ala | Val | Gln | Gly | Val | Ala | Ser | Met | Val | Cys | Phe | Tyr | Gly | Val | |
| | | | 245 | | | | | 250 | | | | | 255 | | | |
| cct | ctt | ctg | att | gtc | aac | ggg | ttc | tta | gtt | ttg | atc | act | tac | ttg | cag | 1112 |
| Pro | Leu | Leu | Ile | Val | Asn | Gly | Phe | Leu | Val | Leu | Ile | Thr | Tyr | Leu | Gln | |
| | 260 | | | | | 265 | | | | | 270 | | | | | |
| cac | acg | cat | cct | tcc | ctg | cct | cac | tat | gac | tcg | tct | gag | tgg | gat | tgg | 1160 |
| His | Thr | His | Pro | Ser | Leu | Pro | His | Tyr | Asp | Ser | Ser | Glu | Trp | Asp | Trp | |
| 275 | | | | | 280 | | | | | 285 | | | | | 290 | |
| ttg | agg | gga | gct | ttg | gcc | acc | gtt | gac | aga | gac | tac | gga | atc | ttg | aac | 1208 |
| Leu | Arg | Gly | Ala | Leu | Ala | Thr | Val | Asp | Arg | Asp | Tyr | Gly | Ile | Leu | Asn | |
| | | | | 295 | | | | | 300 | | | | | 305 | | |
| aag | gtc | ttc | cac | aat | atc | acg | gac | acg | cac | gtg | gcg | cat | cac | ctg | ttc | 1256 |
| Lys | Val | Phe | His | Asn | Ile | Thr | Asp | Thr | His | Val | Ala | His | His | Leu | Phe | |
| | | | 310 | | | | | 315 | | | | | 320 | | | |
| tcg | acc | atg | ccg | cat | tat | cat | gcg | atg | gaa | gct | acg | aag | gcg | ata | aag | 1304 |
| Ser | Thr | Met | Pro | His | Tyr | His | Ala | Met | Glu | Ala | Thr | Lys | Ala | Ile | Lys | |
| | | 325 | | | | | 330 | | | | | 335 | | | | |
| ccg | ata | ctg | gga | gag | tat | tat | cag | ttc | gat | ggg | acg | ccg | gtg | gtt | aag | 1352 |
| Pro | Ile | Leu | Gly | Glu | Tyr | Tyr | Gln | Phe | Asp | Gly | Thr | Pro | Val | Val | Lys | |
| | 340 | | | | | 345 | | | | | 350 | | | | | |
| gcg | atg | tgg | agg | gag | gcg | aag | gag | tgt | atc | tat | gtg | gaa | ccg | gac | agg | 1400 |
| Ala | Met | Trp | Arg | Glu | Ala | Lys | Glu | Cys | Ile | Tyr | Val | Glu | Pro | Asp | Arg | |
| 355 | | | | | 360 | | | | | 365 | | | | | 370 | |
| caa | ggt | gag | aag | aaa | ggt | gtg | ttc | tgg | tac | aac | aat | aag | tta | tga | | 1445 |
| Gln | Gly | Glu | Lys | Lys | Gly | Val | Phe | Trp | Tyr | Asn | Asn | Lys | Leu | | | |
| | | | | 375 | | | | | 380 | | | | | | | |

```
agcaaagaag aaactgaacc tttctcttct atgattgtct ttgtttaaga agctatgttt    1505
ctgtttcaat aatcttaatt atccattttg ttgtgttttc tgacattttg gctaaaatta    1565
tgtgatgttg gaagttagtg tctaaaatgt cttgtgtctg tattgttctt cttctcatcg    1625
ctgttatgtt tgggatcgtt gaaatgtgac tttcggacta gtgaactctt gttctcgaac    1685
tatcttaatg tggatccctg aacagtgtaa tggcttagct tcctctgaaa ctactattat    1745
gttctagtga atcttgacat aaagcaactt gtcg                                1779
```

<210> SEQ ID NO 6
<211> LENGTH: 384
<212> TYPE: PRT
<213> ORGANISM: Brassica napus

<400> SEQUENCE: 6

```
Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
```

```
                305                 310                 315                 320
Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380

<210> SEQ ID NO 7
<211> LENGTH: 4999
<212> TYPE: DNA
<213> ORGANISM: Brassica napus
<220> FEATURE:
<221> NAME/KEY: Intron
<222> LOCATION: (1794)..(2916)
<220> FEATURE:
<221> NAME/KEY: mutation
<222> LOCATION: (3223)..(3223)
<223> OTHER INFORMATION: G to A in HIOL103

<400> SEQUENCE: 7
gtaacagctg aataaatgaa atgaaatcat ggtaggtgat gatcttaaaa aaaatgttga       60
aaataatgtg cgttgttaca atagcatctc ctaaccactt ttatatatgt ctctataata      120
gcatttagat ttagaagtaa aatcactgca atcctacttt atttcttcct ctaaaataaa      180
aattgttatt ttcacggaaa tacattcctt tataataaaa acatactttt ttattcccaa      240
aataatcttt taattttta ttttaacaat tataacccaa ataaatattt tttaatgaaa      300
atgtaccgtt tatataaata tataatcata cttttattt acataatagt ttctataaaa      360
atattccgta taaataatat catagtttta tgaatgttac cctaaattgg attggttttc      420
aactttccca ataaaaagt actatttata aattagaaa aaaatatatc aagactattc      480 tttttagag gaagaaatag aagaatacat tggaaacaaa tctatctcta ttatatagtt      540
ttcctatttt agaaaaaaaa aatagagaaa tacattggag atggtttaag cggtagtaac      600 acaagaaaa actctaaata tcttaagagc atctctaatg tacacttctg taatttcttc      660
taaaatagag atctctatta tagaggtgaa aatgctccaa tgtatgcctc tataatagaa      720
ttcatctatt ttaaaagaaa atatagagaa aaattacttt ttgcttttat atttaaaggt      780
ggaaataaaa tatctctata taaataaata aactctatta tacatgtata cattggagca      840
ttttcacttt tataatagag tttttttatt ttaagaaaaa atatagagat agaaatagaa      900
atagaaatag agatgagttg gagattagaa atagagatga gtttgagatg ttgttacgta      960
agaaagagct agagctttaa taaagtactt aaattaatta ctagtcggca gtcgctgcct     1020
acttgtttac cacctaaatt aatttattat aatatatatt acgaatctcc aaagtacaca     1080
tcacacacac tctactcacg tgatctcaac cacaatgtct gcagatattt tttatagttt     1140
tttctcacat gggagagaag aagccaagca cgatcctcca tcctcaactt tatagcattt     1200
ttttcttttc tttccggcta ccacttgtga gtcgagtcgg caagggcgtt tccttatatt     1260
aaagtaaaga catcaaatac catcgtctta atgctaatta acgtaattga tgagttctat     1320
aacataatcc aaactagtct ttgtgaacat taggattggg taaaccaata tttacatttt     1380
aaaaacaaaa tacaaaaga aacgtgataa actttataaa agcaattata tgatcactgc     1440
atctttccca ctttccgta aataaataca taaaagtgcc gtaaatatca gatatttgga     1500
```

-continued

```
gtagaaaagt aataaagaaa agaaatatga ggagagggaa taatggaggg ggcccacttg      1560
taaaaaagaa agaaaagaga tgtcactcaa tcgtctccca cgggcccccg tcaattaaac      1620
ggcctgcctt ctgcccaatc gcatcttatc agaaccagac agattcatta ccaaagagat      1680
agagaaagag agagagagag agagagagag agagtgagtt tgaggaggag cttcttcgta      1740
gggttcatcg ttattaacgt taaatcttca cccectacgt cagccagctc aaggtccctt      1800
tcttcttcca tttcttttca ttctacgttg ttttcaatct tatgaaactt tctggtctgt      1860
gcttttctta tcgcttttct attctatcta tcattttgc atttcagtcg atttaattct       1920
agatctgtta atattaaact atagatcgt tcttgattct ctgttttcat gtgtgaaatc      1980
tgatgctgta ttaatctgat tatattgtct ataccgtgga gaatatcaaa tgttgcattt      2040
tcatttgtcc gaatacaaag tgtttgactt tcaatcgttt ttaattatat atatatatat     2100 atttttgat gggttggtgg agttgaaaaa tcaccatagc agtctcacgt cctggtttta     2160
gaaatatcct attcaaaatt atatatttgt ttacttgttt tagatctgga cctgagacat      2220
ataagtacct atttgttgaa tctttgggta aaaacttatg tctctgggta aaatttgctg      2280
ggagatttga ccgattccta ttggctcttg attctgtagt tacgtaatac atgaaaaagt      2340
ttcatttggc ctatgctcac ttcatgctta taaacgtttt cttgcaaatt aattggatta      2400
gatgttattt catagattca gtcattcaga tacaatggag ttgcatgaag aaaataatag      2460
aattcgtgac agtaaaaaag attgtatttt tgtttgtttg tttatgttta aaagtctata      2520
tgttgacaat agagttgctc tcaactgttt catttagctt ctttttttgt caagttgctt      2580
attcttagag acattgtgat tatgacttgt cttctttaac gtagtttagt aataaaagac      2640
gaaagaaatt gatatccaca agaaagagat gtgagctgta gcgtatcaaa tctcgttcat      2700
ttactagtag tattctcaac gctatcgttt atttatttt ctttcgttgg tttgccacta      2760
tatgccactt ctctcctctt tgtcccacgt actatccatt ttttttgtgg tagtccattt      2820
tcttgtaact tataataacg taactctgaa tcttttgtct gtagattaat ttgttggttt      2880
aattaacttt taagtctttg cttttggctt atgcagaaac atgggtgcag gtggaagaat      2940
gcaagtgtct cctccctcca agaagtctga aaccgacacc atcaagcgcg taccctgcga      3000
gacaccgccc ttcactgtcg gagaactcaa gaaagcaatc ccaccgcact gtttcaaacg      3060
ctcgatccct cgctctttct cctacctcat ctgggacatc atcatagcct cctgcttcta      3120
ctacgtcgcc accacttact tccctctcct ccctcaccct ctctcctact cgcctggcc      3180 tctctactgg gcctgccaag ggtgcgtcct aaccggcgtc tgggtcatag cccacgagtg      3240
cggccaccac gccttcagcg actaccagtg gcttgacgac accgtcggtc tcatcttcca      3300
ctccttcctc ctcgtccctt acttctcctg gaagtacagt catcgacgcc accattccaa      3360
cactggctcc ctcgagagag acgaagtgtt tgtccccaag aagaagtcag acatcaagtg      3420
gtacggcaag tacctcaaca acccctttggg acgcaccgtg atgttaacgg ttcagttcac      3480
tctcggctgg ccgttgtact tagccttcaa cgtctcggga agaccttacg acggcggctt      3540
cgcttgccat ttccacccca acgctcccat ctacaacgac cgcgagcgtc tccagatata      3600
catctccgac gctggcatcc tcgccgtctg ctacggtctc ttccgttacg ccgccgcgca      3660
gggagtggcc tcgatggtct gcttctacgg agtcccgctt ctgattgtca atggtttcct      3720
cgtgttgatc acttacttgc agcacacgca tccttccctg cctcactacg attcgtccga      3780
gtgggattgg ttgaggggag ctttggctac cgttgacaga gactacgaa tcttgaacaa      3840 ggtcttccac aatattaccg acacgcacgt ggcgcatcat ctgttctcca cgatgccgca      3900
```

```
ttatcacgcg atggaagcta ccaaggcgat aaagccgata ctgggagagt attatcagtt    3960
cgatgggacg ccggtggtta aggcgatgtg gagggaggcg aaggagtgta tctatgtgga    4020
accggacagg caaggtgaga agaaaggtgt gttctggtac aacaataagt tatgaggata    4080
tgatgatggt gaaagaacaa agaagatatt gtcacgaacc tttctcttgc tgtctctggt    4140
cgtctttgtt ttaagaagct atgttttcgt ttcaataatc ttaactatcc attttgttgt    4200
gttttctgac attttggcta agttatgtga tgtgggacac gttagtgtct aaaatgtctc    4260
tgtgtctgta ttgttcttct catctgtgac tttcggacaa ctaaactctt gttctcgaac    4320
tacctcaatg tggcattaat gaaagtgtta ttgttgattt taatctgaaa ctgctattat    4380
ttagtgaatt tttacatcag ccaacttgtt tgtttaagac ctaccaatgg tataagaagg    4440
tttgtgtact aatgttcacc atgtccatag tgttaagaca taaccatgat cttctgtcca    4500
attaatttgc gtcgagttat cgtgttattt ggcacctta ctatgttttt ttgtaaagaa    4560
ctccttacag aatagctttt tgtaaagaac tacgttttat cttttgtaa gaaccttta    4620 acaaaagcca aattcattat tacctggcac aagaaaaaac tctggtttct tcctctttct    4680
ctgtttttag atttgaggag gaacatgaag atgaagaaaa agaaacaaat aaataacaaa    4740 tctcttttt tccattaacg gcagaaacac caaacagag tgacaacaag aaacaaatgt    4800
agtgaggaaa aaccaaagaa aaagaatat tctgaaacca actcgttgaa catattcaaa    4860
tacgaaacaa tctttcatcc aacggcgagc gtaatctaga agcatttcct gtggactatc    4920
gatggccctg cctcatcata ctcagccttt gctatccaca tctgcaagac caacattgtg    4980
tatcatagtc agcttaaaa                                                 4999

<210> SEQ ID NO 8
<211> LENGTH: 1800
<212> TYPE: DNA
<213> ORGANISM: Brassica napus
<220> FEATURE:
<221> NAME/KEY: CDS
<222> LOCATION: (318)..(1472)
<220> FEATURE:
<221> NAME/KEY: mutation
<222> LOCATION: (620)..(620)
<223> OTHER INFORMATION: G to A in HIOL103

<400> SEQUENCE: 8
gtaaatatca gatatttgga gtagaaaagt aataaagaaa agaaatatga ggagagggaa      60
taatggaggg ggcccacttg taaaaaagaa agaaaagaga tgtcactcaa tcgtctccca     120
cgggcccccg tcaattaaac ggcctgcctt ctgcccaatc gcatcttatc agaaccagac     180
agattcatta ccaaagagat agagaaagag agagagagag agagagagag agagtgagtt     240
tgaggaggag cttcttcgta gggttcatcg ttattaacgt taaatcttca cccctacgt      300 cagccagctc aagaaac atg ggt gca ggt gga aga atg caa gtg tct cct         350
                    Met Gly Ala Gly Gly Arg Met Gln Val Ser Pro
                     1               5                  10 ccc tcc aag aag tct gaa acc gac acc atc aag cgc gta ccc tgc gag        398
Pro Ser Lys Lys Ser Glu Thr Asp Thr Ile Lys Arg Val Pro Cys Glu
             15                  20                  25 aca ccg ccc ttc act gtc gga gaa ctc aag aaa gca atc cca ccg cac        446
Thr Pro Pro Phe Thr Val Gly Glu Leu Lys Lys Ala Ile Pro Pro His
         30                  35                  40 tgt ttc aaa cgc tcg atc cct cgc tct ttc tcc tac ctc atc tgg gac        494
Cys Phe Lys Arg Ser Ile Pro Arg Ser Phe Ser Tyr Leu Ile Trp Asp
     45                  50                  55
```

```
atc atc ata gcc tcc tgc ttc tac tac gtc gcc acc act tac ttc cct       542
Ile Ile Ile Ala Ser Cys Phe Tyr Tyr Val Ala Thr Thr Tyr Phe Pro
60              65                  70                  75 ctc ctc cct cac cct ctc tcc tac ttc gcc tgg cct ctc tac tgg gcc       590
Leu Leu Pro His Pro Leu Ser Tyr Phe Ala Trp Pro Leu Tyr Trp Ala
            80                  85                  90 tgc caa ggg tgc gtc cta acc ggc gtc tgg gtc ata gcc cac gag tgc       638
Cys Gln Gly Cys Val Leu Thr Gly Val Trp Val Ile Ala His Glu Cys
        95                  100                 105 ggc cac cac gcc ttc agc gac tac cag tgg ctt gac gac acc gtc ggt       686
Gly His His Ala Phe Ser Asp Tyr Gln Trp Leu Asp Asp Thr Val Gly
    110                 115                 120 ctc atc ttc cac tcc ttc ctc ctc gtc cct tac ttc tcc tgg aag tac       734
Leu Ile Phe His Ser Phe Leu Leu Val Pro Tyr Phe Ser Trp Lys Tyr
125                 130                 135 agt cat cga cgc cac cat tcc aac act ggc tcc ctc gag aga gac gaa       782
Ser His Arg Arg His His Ser Asn Thr Gly Ser Leu Glu Arg Asp Glu
140             145                 150                 155 gtg ttt gtc ccc aag aag aag tca gac atc aag tgg tac ggc aag tac       830
Val Phe Val Pro Lys Lys Lys Ser Asp Ile Lys Trp Tyr Gly Lys Tyr
                160                 165                 170 ctc aac aac cct ttg gga cgc acc gtg atg tta acg gtt cag ttc act       878
Leu Asn Asn Pro Leu Gly Arg Thr Val Met Leu Thr Val Gln Phe Thr
            175                 180                 185 ctc ggc tgg ccg ttg tac tta gcc ttc aac gtc tcg gga aga cct tac       926
Leu Gly Trp Pro Leu Tyr Leu Ala Phe Asn Val Ser Gly Arg Pro Tyr
        190                 195                 200 gac ggc ggc ttc gct tgc cat ttc cac ccc aac gct ccc atc tac aac       974
Asp Gly Gly Phe Ala Cys His Phe His Pro Asn Ala Pro Ile Tyr Asn
    205                 210                 215 gac cgc gag cgt ctc cag ata tac atc tcc gac gct ggc atc ctc gcc      1022
Asp Arg Glu Arg Leu Gln Ile Tyr Ile Ser Asp Ala Gly Ile Leu Ala
220                 225                 230                 235 gtc tgc tac ggt ctc ttc cgt tac gcc gcc gcg cag gga gtg gcc tcg      1070
Val Cys Tyr Gly Leu Phe Arg Tyr Ala Ala Ala Gln Gly Val Ala Ser
                240                 245                 250 atg gtc tgc ttc tac gga gtc ccg ctt ctg att gtc aat ggt ttc ctc      1118
Met Val Cys Phe Tyr Gly Val Pro Leu Leu Ile Val Asn Gly Phe Leu
            255                 260                 265 gtg ttg atc act tac ttg cag cac acg cat cct tcc ctg cct cac tac      1166
Val Leu Ile Thr Tyr Leu Gln His Thr His Pro Ser Leu Pro His Tyr
        270                 275                 280 gat tcg tcc gag tgg gat tgg ttg agg gga gct ttg gct acc gtt gac      1214
Asp Ser Ser Glu Trp Asp Trp Leu Arg Gly Ala Leu Ala Thr Val Asp
    285                 290                 295 aga gac tac gga atc ttg aac aag gtc ttc cac aat att acc gac acg      1262
Arg Asp Tyr Gly Ile Leu Asn Lys Val Phe His Asn Ile Thr Asp Thr
300                 305                 310                 315 cac gtg gcg cat cat ctg ttc tcc acg atg ccg cat tat cac gcg atg      1310
His Val Ala His His Leu Phe Ser Thr Met Pro His Tyr His Ala Met
                320                 325                 330 gaa gct acc aag gcg ata aag ccg ata ctg gga gag tat tat cag ttc      1358
Glu Ala Thr Lys Ala Ile Lys Pro Ile Leu Gly Glu Tyr Tyr Gln Phe
            335                 340                 345 gat ggg acg ccg gtg gtt aag gcg atg tgg agg gag gcg aag gag tgt      1406
Asp Gly Thr Pro Val Val Lys Ala Met Trp Arg Glu Ala Lys Glu Cys
        350                 355                 360 atc tat gtg gaa ccg gac agg caa ggt gag aag aaa ggt gtg ttc tgg      1454
Ile Tyr Val Glu Pro Asp Arg Gln Gly Glu Lys Lys Gly Val Phe Trp
```

```
                365             370             375
tac aac aat aag tta tga ggatatgatg atggtgaaag aacaaagaag        1502
Tyr Asn Asn Lys Leu
380 atattgtcac gaacctttct cttgctgtct ctggtcgtct ttgttttaag aagctatgtt  1562 ttcgtttcaa taatcttaac tatccatttt gttgtgtttt ctgacatttt ggctaagtta  1622 tgtgatgtgg gacacgttag tgtctaaaat gtctctgtgt ctgtattgtt cttctcatct  1682 gtgactttcg gacaactaaa ctcttgttct cgaactacct caatgtggca ttaatgaaag  1742 tgttattgtt gattttaatc tgaaactgct attatttagt gaattttttac atcagcca   1800
```

<210> SEQ ID NO 9
<211> LENGTH: 384
<212> TYPE: PRT
<213> ORGANISM: Brassica napus
<400> SEQUENCE: 9

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
```

```
            290                 295                 300
Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380
```

<210> SEQ ID NO 10
<211> LENGTH: 3255
<212> TYPE: DNA
<213> ORGANISM: Brassica napus
<220> FEATURE:
<221> NAME/KEY: Intron
<222> LOCATION: (774)..(1388)
<220> FEATURE:
<221> NAME/KEY: mutation
<222> LOCATION: (2057)..(2057)
<223> OTHER INFORMATION: C to T mutation in HIOL111

<400> SEQUENCE: 10

```
gttcacatgg gctaaaggga gaagaagcca aacacgatac tccatttttcc actttcagca      60
accttttttta tttcccgaca ccagtatttt tgtgacttgt ggagtcgcca cgccaaggac     120
gttgcttcat taaatgaaag gcatcatcaa ctaccatcta cttctacttc ttctgcttat     180
tcttgattat tacgaccgac gaattattaa tcaatatatg aatagttggg cgtcttaatt     240
atcaccactt tatcaagttg tttctaatct catattaaga aatgatacat gattgactta     300
cgtagagaaa actggttcaa acaagtacc gcatgtgtta ttgcgttcca aagtgattaa      360
gtaaataaca tgatacgacc atttttttatt acattacata ggtaaccaag ataacgtgga     420
cgagaaaaag agagaatgtc gtagtaatat cacctttttca tcactgtaac ttttacatttt    480
tggtaaattc taaactaatg gtcgttcgtt ggcccagttg aaaataagag aaaagagggg     540
cccagttgaa aaagaagag atgtcattca aatgccttcc tctctcatca atttaaaaac      600
ggccctgcct attgccactc ccatctgacc agacaaacta caacgattg agaaagtgcc      660
gagacaagag agagaaagag aagaaagata gattctttgg aggagcttca ttgtagggtt     720
catcgttatt aacgtaaaat ctctcccccc accctacgtc agcagctttc aaggtcttct     780
tcttcttctt ctcatttttcc tcttattttt atgaatttct ggtctgtgtt tatctcgtcg     840
cgtccatctc tctagtattt ggaatttcaa tcgataaatc tactaatctt attgcattca     900
actataaatc tgcttctctg tttccattttg acaaatctta tcatgttcct ttcatctcac     960
acattaataa tgattactgt ctatcgtctc gcatatgcac ccatgttttct tctcaattat     1020
gattagtgcc ttcttcacta tctatttaga actctcttta ttccataggt tggttagaaa     1080
aatcacctat tgttgaatct tttgattgac ttgaccgatt cctattggtt cttggtactg     1140
tatataaata cttaataaat ggaagaacgt tcattgact tataataagc tcatcaactt     1200
tgtacaaata aaacgatga tttaaattag gtaggtactt cagggttcag atgctctttc     1260
atagattcaa atgcataaag agtttgcatg tacaaatttg attaaagaat aaaaaaaaaa     1320
aaaaagtac tccctgtctc cataacatta acttcttttt cctttttttt ttttggtttt     1380
ctctacagaa acaaacatgg gcgcaggtgg aagaatgcaa gtctctcctc cctccagctc     1440
```

```
ccccggaacc aacaccctca aacgcgtccc ctgcgagaca ccaccattca ctctcggaga    1500
cctcaagaaa gcaatcccac ctcactgctt caaacgctcc atcccacgct ccttctcctc    1560
ttcgacatca tcatctcctc ctcggctcct ccctctacca cctctccaca gcctacttcc    1620
ctctccctta cctcgcctga cccctctact gggcctgcca aggctgcgtc taacgggcc     1680 tctgggtcat agcccacgag tgcggccacc acgccttcag cgaccaccag tggctggacg    1740
acgccgtcgg cctcgtcttc cactccttcc tcctcgtccc gtacttctcc tggaagtaca    1800
tccatgatac atcaagtggt acggcaagta cctcaacaac ccgctaggac gcacggtgat    1860
gctaaccgtc cagttcaagc tcggctggcc gttgtactta gccttcaacg tctcgggaag    1920
accttacagc gacggtttcg cttgccattt ccacccgaac gctcccatct acaacgaccg    1980
cgagcgtctc cagatataca tctctgacgc tggcgtcctc tccgtatgtt acggtctcta    2040
ccgttacgct gcttcgcgag gagtagcctc tgtggtctgt gtctacggag ttccgcttct    2100
aattgtcaac tgtttcctcg tcttgatcac ttacttgcag cacacgcacc cttcgctgcc    2160
tcactatgat tcttccgagt gggattggtt gagaggagct ttggctactg tggatagaga    2220
ctatggaatc ttgaacaagg tgttccataa catcacggac acgcacgtgg cgcatcatct    2280
gttctcgacg atgccgcatt ataacgcgat ggaagcgacc aaggcgataa agccgatact    2340
ttggagagta ttaccagttt gatggaacgc cggcggttaa ggcgatgtgg agggaggcga    2400
aggagtgtat ctatgttgaa ccggataggc aaggtgagaa gaaggtgtg ttctggtaca     2460 acaataagtt atgaggatga tgatgatgat gatgatagtg gaaggacaga gttaaaagtt    2520
gttgtcgact tttctcttgg tctggtttag tctttgttct aattagaaac tatgtatttt    2580
ttttggtagg ctgcaggcct acttttatt caaatcaaaa caaaacaact acaggcaaat     2640
ttgtcgagtt ctggacactc cgttacaatc ttctaacaaa actgaagcaa catgctctgg    2700
agccgactca aaataatgta aaccaaacgg taaagaaaac gcatagttag ctaatccatc    2760
tgctagacaa ttagcctccc tatacacgtg agaaattttg actatccagt ctcttgaaat    2820
gaagtcatag cacaaacgta ctaggaagga tatgggatga gaatcatgaa tccctgtctg    2880
aagaaaaccc gccacactct ctgaatcaac ttccacctct agcctccgaa taccacaatc    2940
tcatgctatg cacagtccat agtaaacacc ccacagttct gccaacggag ccaaacaaat    3000
acctatatta atcgcaaaac ctcctttcca cattccaaat tcgtctcgca cagctcctcc    3060
cgctgtggcc agtccagggt taccctaga tgctccatca atgttcaatt taagccagcc     3120
attaacgggt cgctgccatg cgatttgctt ctccaccccgg cccctagcac aagaacgatc   3180
tcgcaaatgc ttatttgctt ccaacacttc tctggacttt tctttaacaa actgcactct    3240
gtctcgacat gtcct                                                     3255
```

<210> SEQ ID NO 11
<211> LENGTH: 1333
<212> TYPE: DNA
<213> ORGANISM: Brassica napus
<220> FEATURE:
<221> NAME/KEY: CDS
<222> LOCATION: (138)..(548)
<220> FEATURE:
<221> NAME/KEY: mutation
<222> LOCATION: (798)..(798)
<223> OTHER INFORMATION: C to T mutation in HIOL111

<400> SEQUENCE: 11

```
agattgagaa agtgccgaga caagagagag aaagagaaga aagatagatt ctttggagga     60
```

```
gcttcattgt agggttcatc gttattaacg taaaatctct cccccacccc tacgtcagca    120
gctttcaaga aacaaac atg ggc gca ggt gga aga atg caa gtc tct cct      170
                Met Gly Ala Gly Gly Arg Met Gln Val Ser Pro
                1               5                   10 ccc tcc agc tcc ccc gga acc aac acc ctc aaa cgc gtc ccc tgc gag    218
Pro Ser Ser Ser Pro Gly Thr Asn Thr Leu Lys Arg Val Pro Cys Glu
            15                  20                  25 aca cca cca ttc act ctc gga gac ctc aag aaa gca atc cca cct cac    266
Thr Pro Pro Phe Thr Leu Gly Asp Leu Lys Lys Ala Ile Pro Pro His
        30                  35                  40 tgc ttc aaa cgc tcc atc cca cgc tcc ttc tcc tct tcg aca tca tca    314
Cys Phe Lys Arg Ser Ile Pro Arg Ser Phe Ser Ser Ser Thr Ser Ser
    45                  50                  55 tct cct cct cgg ctc ctc cct cta cca cct ctc cac agc cta ctt ccc    362
Ser Pro Pro Arg Leu Leu Pro Leu Pro Pro Leu His Ser Leu Leu Pro
60                  65                  70                  75 tct ccc tta cct cgc ctg acc cct cta ctg ggc ctg cca agg ctg cgt    410
Ser Pro Leu Pro Arg Leu Thr Pro Leu Leu Gly Leu Pro Arg Leu Arg
                80                  85                  90 cct aac ggg cct ctg ggt cat agc cca cga gtg cgg cca cca cgc ctt    458
Pro Asn Gly Pro Leu Gly His Ser Pro Arg Val Arg Pro Pro Arg Leu
            95                  100                 105 cag cga cca cca gtg gct gga cga cgc cgt cgg cct cgt ctt cca ctc    506
Gln Arg Pro Pro Val Ala Gly Arg Arg Arg Pro Arg Leu Pro Leu
        110                 115                 120 ctt cct cct cgt ccc gta ctt ctc ctg gaa gta cat cca tga            548
Leu Pro Pro Arg Pro Val Leu Leu Leu Glu Val His Pro
    125                 130                 135 tacatcaagt ggtacggcaa gtacctcaac aacccgctag acgcacggt gatgctaacc     608 gtccagttca agctcggctg ccgttgtac ttagccttca acgtctcggg aagaccttac     668
agcgacggtt tcgcttgcca tttccacccg aacgctccca tctacaacga ccgcgagcgt    728
ctccagatat acatctctga cgctggcgtc tctccgtat gttacggtct ctaccgttac     788
gctgcttcgc gaggagtagc ctctgtggtc tgtgtctacg gagttccgct tctaattgtc    848
aactgtttcc tcgtcttgat cacttacttg cagcacacgc accttcgct gcctcactat    908 gattcttccg agtgggattg gttgagagga gctttggcta ctgtggatag agactatgga   968
atcttgaaca aggtgttcca taacatcacg gacacgcacg tggcgcatca tctgttctcg   1028
acgatgccgc attataacgc gatggaagcg accaaggcga taaagccgat actttggaga   1088
gtattaccag tttgatggaa cgccggcggt taaggcgatg tggagggagg cgaaggagtg   1148
tatctatgtt gaaccggata ggcaaggtga aagaaaggt gtgttctggt acaacaataa    1208
gttatgagga tgatgatgat gatgatgata gtggaaggac agagttaaaa gttgttgtcg   1268
acttttctct tggtctggtt tagtctttgt tctaattaga aactatgtat ttttttggt    1328 aggct                                                              1333
```

<210> SEQ ID NO 12
<211> LENGTH: 136
<212> TYPE: PRT
<213> ORGANISM: Brassica napus

<400> SEQUENCE: 12

```
Met Gly Ala Gly Gly Arg Met Gln Val Ser Pro Pro Ser Ser Ser Pro
1               5                   10                  15

Gly Thr Asn Thr Leu Lys Arg Val Pro Cys Glu Thr Pro Pro Phe Thr
```

```
              20                  25                  30
Leu Gly Asp Leu Lys Lys Ala Ile Pro Pro His Cys Phe Lys Arg Ser
         35                  40                  45

Ile Pro Arg Ser Phe Ser Ser Thr Ser Ser Pro Pro Arg Leu
 50                  55                  60

Leu Pro Leu Pro Pro Leu His Ser Leu Leu Pro Ser Pro Leu Pro Arg
 65                  70                  75                  80

Leu Thr Pro Leu Leu Gly Leu Pro Arg Leu Arg Pro Asn Gly Pro Leu
                 85                  90                  95

Gly His Ser Pro Arg Val Arg Pro Arg Leu Gln Arg Pro Pro Val
             100                 105                 110

Ala Gly Arg Arg Arg Pro Arg Leu Pro Leu Leu Pro Arg Pro
             115                 120                 125

Val Leu Leu Leu Glu Val His Pro
             130                 135

<210> SEQ ID NO 13
<211> LENGTH: 3300
<212> TYPE: DNA
<213> ORGANISM: Brassica napus
<220> FEATURE:
<221> NAME/KEY: Intron
<222> LOCATION: (816)..(1750)
<220> FEATURE:
<221> NAME/KEY: mutation
<222> LOCATION: (2327)..(2327)
<223> OTHER INFORMATION: G to A in HIOL109

<400> SEQUENCE: 13
attactagtt tcttttcgtc tgccaacaaa tttgattatt ataagtatca aagatgatta    60
cacatacata acaaattgta ataagaaaaa gaaaagagag agaaatcctc acgtgagcat   120
caccacaatt tgtctgttac atatttctgt aagttcttgt gtgttcacat gggcaaaagt   180
gagaagaagc caaacacgat actccatttt caggcatcaa ctaccatctt cttcttcttc   240
ttctttatca agttgtttct aatgtcatat taagaaatga tacatgattg acttacgtag   300
agaaaaactg attcaaacaa gtaccgcatg tgtcattgcg ttccaaagtg attaagtcaa   360
taacatgata cgacctttt tattacatta catacataac caagataacg tggacgagaa   420
aaagagagaa cgtcgtagta atatcacctt tcatcactc taacttttac attttggtaa    480
attctaaatt aatggtcgtt ccttgagtta aatatcagat attttgaaca gaggggccca   540
gttgtaaaaa taagagaaaa gaggggccag ttgtaagaat aagagatgtc attcaaatgc   600
cttcctgtct ctcatcaatt taaaaacggc cctgcctatt gccactcgca tctgaccaga   660
caaaccacaa cagattgaga gaagtgccga gacaagagag agagagagag aaagagaaga   720
gagagagata gattctttgg aggagcttca ttgtagggtt catcgttatt aacgtaaaat   780
ctctctcccc ccaccctacg tcagcagctt tcagggtccc cttcttcttc ttcttcttct   840
cattttcctc ttattttat gaattcctgg tctgtgttca cctcgtccat ctctctagca    900
gtctagcatt tggcatttaa atcgatagat ctgccagtct ttattgcatt caactaaaga   960
tctgttcctc tgtttccatt tgacaaatct tgtgtcatgt ttctttcatc tcaccgttaa  1020
ataatgatta ctgtctatgg tctagcatat gaaatgttgc aactttctat ctattcagaa  1080
atctttttat tcaataggtt ggtgaaatag aaaaggtcaa atctccaaaa tagcaacttt  1140
ctaagtttat atcacaaaaa tagcactcaa aaattaaaat gaccaaaata ttattttatc  1200
ttttgaaaat tttaattttt ttatttttca aaatttgaaa tcttatcccc aaaaacctcat  1260
```

```
ttctcaactc taaaccctaa actctgaacc ataaaccta aacctaaac tctaaaccct      1320
aaaccctaaa ccctaaaccc cacccttaa ctctaaacca taagtttgtg acttttgata     1380
aaatattaag tgatattttt gtgacttttg accttgagtg ctagtttggg aacaaaaact   1440
tggtttagtg ctattttgt ttttttcaa tataaaaatc acttattgtt gaacctttga      1500
tagatttgac cgattcctac tggttcttgc tactgttatt tcttaataaa tggaagaacg    1560
tttcattgac ttataagctc atcaactttg tacaaataaa acggatgatt taaagtaggt    1620
aggtacttca gggtttagat gttctttat agattcaaat gcatgaagag ttgcatatac    1680
aactttgatt aaaggataaa aagtctccgt cctccataac attattatta tttttggtt    1740
ttctctacag aaacaaacat gggcgcaggt ggaagaatgc aaatctctcc tccctccagc    1800
tcccccgaaa ccaaaaccct caaacgcgtc cctgcgaga caccaccctt cactctcgga    1860
gacctcaaga aagcaatccc acctcactgc ttcaaacgct ccatccctcg ctccttctcc    1920
tacctcctct tcgacatcct cgtcctcc tccctctacc acctccac agcctacttc       1980
cctctcctcc cccaccctct cccttacctc gcctggcccc tctactgggc ctgccaaggc   2040
tgcgtcctaa cgggcctctg ggtcatcgcc cacgaatgcg gccaccacgc cttcagcgac   2100
caccagtggc tggacgacgc cgtgggcctc gtcttccact ccttcctcct cgtcccttac   2160
ttctcctgga agtacagcca tcgacgccac cattccaaca ccggatccct cgagagggat   2220
gaagtgttcg tccccaagaa gaaatccgac atcaagtggt acggaaagta cctcaacaac   2280
ccgctaggac gcacggtgat gctaaccgtc cagttcacgc tcggctggcc gttgtactta   2340
gccttcaacg tctctggaag accttacagc gacggttcg cttgccattt ccacccgaac    2400
gctcccatct acaacgaccg cgagcgtctc cagatataca tctctgacgc tggcgtcctc   2460
tccgtatgtt acggtctcta ccgctacgct ggttcgcgag gagtggcctc gatggtctgt   2520
gtctacggag ttccgcttat gattgtcaac tgtttcctcg tcttgatcac ttacttgcag   2580
cacacgcacc cttcgctgcc tcactatgat tcttcggagt gggattggtt gagaggagct   2640
ttggctactg tggatagaga ctatggaatc ttgaacaagg tgtttcataa catcacggac   2700
acgcacgtgg cgcatcatct gttctcgacg atgccgcatt ataacgcgat ggaagcgacc   2760
aaggcgataa agccgatact ggagagtat taccagtttg atggaacgcc ggtggttaag    2820
gcgatgtgga gggaggcgaa ggagtgtatc tatgttgaac cggataggca aggtgagaag   2880
aaaggtgtgt tctggtacaa caataagtta tgaggatgat gatgatgatg atgatgatga   2940
tgatgatgat gatgatggtg gaaggacaga gttaaaagtt gttgtcgact tttctcttgg   3000
tctggtttag tctttgttct aattagaaac tatgtatttg ttacagtaat gttattattg   3060
tctcattttg ttgtgttatg acattttggc ttaaattaag tatgttttag cattttctt    3120
gcttaaacca aaaaaaaatg tgaatggggg aatcaaagat catattgtgc tctacctaca    3180
gaacctaata tgctaagtta tggggccagt aaaagcatct taaaaagaaa attcaccatc   3240
cgtcctctat attattcttt gcttaccttt cattgatcat tgtgaattta tctgattcta   3300
```

<210> SEQ ID NO 14
<211> LENGTH: 1498
<212> TYPE: DNA
<213> ORGANISM: Brassica napus
<220> FEATURE:
<221> NAME/KEY: CDS
<222> LOCATION: (153)..(1307)
<220> FEATURE:
<221> NAME/KEY: mutation
<222> LOCATION: (721)..(721)
<223> OTHER INFORMATION: G to A in HIOL109

<400> SEQUENCE: 14

| | |
|---|---|
| agattgagag aagtgccgag acaagagaga gagagagaga aagagaagag agagagatag | 60 |
| attctttgga ggagcttcat tgtagggttc atcgttatta acgtaaaatc tctctccccc | 120 |
| caccctacgt cagcagcttt caggaaacaa ac atg ggc gca ggt gga aga atg<br>                                                  Met Gly Ala Gly Gly Arg Met<br>                                                1             5 | 173 |
| caa atc tct cct ccc tcc agc tcc ccc gaa acc aaa acc ctc aaa cgc<br>Gln Ile Ser Pro Pro Ser Ser Ser Pro Glu Thr Lys Thr Leu Lys Arg<br>        10                    15                     20 | 221 |
| gtc ccc tgc gag aca cca ccc ttc act ctc gga gac ctc aag aaa gca<br>Val Pro Cys Glu Thr Pro Pro Phe Thr Leu Gly Asp Leu Lys Lys Ala<br>25                    30                    35 | 269 |
| atc cca cct cac tgc ttc aaa cgc tcc atc cct cgc tcc ttc tcc tac<br>Ile Pro Pro His Cys Phe Lys Arg Ser Ile Pro Arg Ser Phe Ser Tyr<br>40                    45                    50                    55 | 317 |
| ctc ctc ttc gac atc ctc gtc tcc tcc ctc tac cac ctc tcc aca<br>Leu Leu Phe Asp Ile Leu Val Ser Ser Ser Leu Tyr His Leu Ser Thr<br>                    60                            65                        70 | 365 |
| gcc tac ttc cct ctc ctc ccc cac cct ctc cct tac ctc gcc tgg ccc<br>Ala Tyr Phe Pro Leu Leu Pro His Pro Leu Pro Tyr Leu Ala Trp Pro<br>          75                          80                          85 | 413 |
| ctc tac tgg gcc tgc caa ggc tgc gtc cta acg ggc ctc tgg gtc atc<br>Leu Tyr Trp Ala Cys Gln Gly Cys Val Leu Thr Gly Leu Trp Val Ile<br>              90                          95                      100 | 461 |
| gcc cac gaa tgc ggc cac cac gcc ttc agc gac cac cag tgg ctg gac<br>Ala His Glu Cys Gly His His Ala Phe Ser Asp His Gln Trp Leu Asp<br>105                   110                    115 | 509 |
| gac gcc gtg ggc ctc gtc ttc cac tcc ttc ctc ctc gtc cct tac ttc<br>Asp Ala Val Gly Leu Val Phe His Ser Phe Leu Leu Val Pro Tyr Phe<br>120                   125                    130                    135 | 557 |
| tcc tgg aag tac agc cat cga cgc cac cat tcc aac acc gga tcc ctc<br>Ser Trp Lys Tyr Ser His Arg Arg His His Ser Asn Thr Gly Ser Leu<br>                 140                    145                    150 | 605 |
| gag agg gat gaa gtg ttc gtc ccc aag aag aaa tcc gac atc aag tgg<br>Glu Arg Asp Glu Val Phe Val Pro Lys Lys Lys Ser Asp Ile Lys Trp<br>              155                    160                    165 | 653 |
| tac gga aag tac ctc aac aac ccg cta gga cgc acg gtg atg cta acc<br>Tyr Gly Lys Tyr Leu Asn Asn Pro Leu Gly Arg Thr Val Met Leu Thr<br>              170                    175                    180 | 701 |
| gtc cag ttc acg ctc ggc tgg ccg ttg tac tta gcc ttc aac gtc tct<br>Val Gln Phe Thr Leu Gly Trp Pro Leu Tyr Leu Ala Phe Asn Val Ser<br>185                   190                    195 | 749 |
| gga aga cct tac agc gac ggt ttc gct tgc cat ttc cac ccg aac gct<br>Gly Arg Pro Tyr Ser Asp Gly Phe Ala Cys His Phe His Pro Asn Ala<br>200                   205                    210                    215 | 797 |
| ccc atc tac aac gac cgc gag cgt ctc cag ata tac atc tct gac gct<br>Pro Ile Tyr Asn Asp Arg Glu Arg Leu Gln Ile Tyr Ile Ser Asp Ala<br>                 220                    225                    230 | 845 |
| ggc gtc ctc tcc gta tgt tac ggt ctc tac cgc tac gct ggt tcg cga<br>Gly Val Leu Ser Val Cys Tyr Gly Leu Tyr Arg Tyr Ala Gly Ser Arg<br>              235                    240                    245 | 893 |
| gga gtg gcc tcg atg gtc tgt gtc tac gga gtt ccg ctt atg att gtc<br>Gly Val Ala Ser Met Val Cys Val Tyr Gly Val Pro Leu Met Ile Val<br>            250                    255                    260 | 941 |
| aac tgt ttc ctc gtc ttg atc act tac ttg cag cac acg cac cct tcg<br>Asn Cys Phe Leu Val Leu Ile Thr Tyr Leu Gln His Thr His Pro Ser | 989 |

```
                    265                 270                 275
ctg cct cac tat gat tct tcg gag tgg gat tgg ttg aga gga gct ttg        1037
Leu Pro His Tyr Asp Ser Ser Glu Trp Asp Trp Leu Arg Gly Ala Leu
280                 285                 290                 295 gct act gtg gat aga gac tat gga atc ttg aac aag gtg ttt cat aac        1085
Ala Thr Val Asp Arg Asp Tyr Gly Ile Leu Asn Lys Val Phe His Asn
                300                 305                 310 atc acg gac acg cac gtg gcg cat cat ctg ttc tcg acg atg ccg cat        1133
Ile Thr Asp Thr His Val Ala His His Leu Phe Ser Thr Met Pro His
            315                 320                 325 tat aac gcg atg gaa gcg acc aag gcg ata aag ccg ata ctt gga gag        1181
Tyr Asn Ala Met Glu Ala Thr Lys Ala Ile Lys Pro Ile Leu Gly Glu
        330                 335                 340 tat tac cag ttt gat gga acg ccg gtg gtt aag gcg atg tgg agg gag        1229
Tyr Tyr Gln Phe Asp Gly Thr Pro Val Val Lys Ala Met Trp Arg Glu
    345                 350                 355 gcg aag gag tgt atc tat gtt gaa ccg gat agg caa ggt gag aag aaa        1277
Ala Lys Glu Cys Ile Tyr Val Glu Pro Asp Arg Gln Gly Glu Lys Lys
360                 365                 370                 375 ggt gtg ttc tgg tac aac aat aag tta tga ggatgatgat gatgatgatg         1327
Gly Val Phe Trp Tyr Asn Asn Lys Leu
                380 atgatgatga tgatgatgat gatggtggaa ggacagagtt aaaagttgtt gtcgactttt     1387 ctcttggtct ggtttagtct tgttctaat  tagaaactat gtatttgtta cagtaatgtt     1447 attattgtct cattttgttg tgttatgaca ttttggctta aattaagtat g              1498

<210> SEQ ID NO 15
<211> LENGTH: 384
<212> TYPE: PRT
<213> ORGANISM: Brassica napus

<400> SEQUENCE: 15

Met Gly Ala Gly Gly Arg Met Gln Ile Ser Pro Pro Ser Ser Pro
1               5                   10                  15

Glu Thr Lys Thr Leu Lys Arg Val Pro Cys Glu Thr Pro Pro Phe Thr
                20                  25                  30

Leu Gly Asp Leu Lys Lys Ala Ile Pro Pro His Cys Phe Lys Arg Ser
            35                  40                  45

Ile Pro Arg Ser Phe Ser Tyr Leu Leu Phe Asp Ile Leu Val Ser Ser
        50                  55                  60

Ser Leu Tyr His Leu Ser Thr Ala Tyr Phe Pro Leu Leu Pro His Pro
65                  70                  75                  80

Leu Pro Tyr Leu Ala Trp Pro Leu Tyr Trp Ala Cys Gln Gly Cys Val
                85                  90                  95

Leu Thr Gly Leu Trp Val Ile Ala His Glu Cys Gly His His Ala Phe
            100                 105                 110

Ser Asp His Gln Trp Leu Asp Asp Ala Val Gly Leu Val Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190
```

```
Tyr Leu Ala Phe Asn Val Ser Gly Arg Pro Tyr Ser Asp Gly Phe Ala
            195                 200                 205

Cys His Phe His Pro Asn Ala Pro Ile Tyr Asn Asp Arg Glu Arg Leu
    210                 215                 220

Gln Ile Tyr Ile Ser Asp Ala Gly Val Leu Ser Val Cys Tyr Gly Leu
225                 230                 235                 240

Tyr Arg Tyr Ala Gly Ser Arg Gly Val Ala Ser Met Val Cys Val Tyr
            245                 250                 255

Gly Val Pro Leu Met Ile Val Asn Cys Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
            325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 16
<211> LENGTH: 3654
<212> TYPE: DNA
<213> ORGANISM: Brassica rapa
<220> FEATURE:
<221> NAME/KEY: Intron
<222> LOCATION: (929)..(2003)

<400> SEQUENCE: 16
gtaacagctg aataaatgaa atgaaatcat ggtaggtgat gatctttaaa aaatgttgaa      60
aataatgtgt gtcgttataa gcggtaatgc atagaaaaac tctaaatcat aagtacttaa     120
attaattact agtcggcagt cgctgcctac ttgtgtacca cctaaattaa tttattataa     180
tatatgacga atctccaaag tacatcacac acactcgggg ctattcacgt gatctcaacc     240
acaatgtctg cagatatttt tttaagtttt cttctcacat gggagaagaa gaagccaagc     300
acgatcctcc atcctcaact ttatagcatt ttttttcttt ctttccggct accactaact     360
tctacagttc tacttgtgag tcggcaagga cgtttcctca tattaaagta aagacatcaa     420
ataccataat cttaatgcta attaacgtaa cggatgagtt ctataacata acccaaacta     480
gtctttgtga acattaggat tgggtaaacc aatatttaca ttttaaaaac aaaatacaaa     540
aagaaacgtg ataaacttta taaaagcaat tatatgatca cggcatcttt ttcactttc     600 cgtaaatata tataagtggt gtaaatatca gatatttgga gtagaaaaaa aaaaaaaaa     660 aaaagaaata tgaagagagg aaataatgga ggggcccact agtaaaaaag aaagaaaga     720 gatgtcactc aatcgtctca cacgggcccc cgtcaattta aacggcctgc cttctgccca     780
atcgcatctt accagaacca gagagattca ttaccaaaga gatagagaga gaaagagagg     840
agacagagag agtttgagga ggtgcttctt cgtagggttc atcgttatta acgttaaatc     900
ttcatccccc tacgtcaacc agctcaaggt ccctttcttc ttccatttct tctcattttt     960
```

```
acgttgtttt caatcttggt ctgttctttt cttatcgctt ttctattcta tctatcattt    1020
ttgcttttca gtcgatttaa ttctagatct gttaatattt attgcattaa actatagatc    1080
tgttcttgat tctctgtttt cttgtgtgaa atcttgatgc tgtctttacc attaatctga    1140
ttatattgtc tataccttgg agaatatgaa atgttgcatt tcatttgtc cgaatacaaa     1200 ctgtttgact ttcaatcttt tttaatgatt tattttgatg ggttggtgga gttgaaaaat    1260
caccatagca gtctcacgtc ctggtcttag aaatatcctt cctattcaaa gttatatata    1320
tttgtttact tgtcttagat ctggacctga gacatgtaag tacctatttg ttgaatcttt    1380
gggtaaaaaa cttatgtctc tgggtaaaat ttgcttggag atttgaccga ttcctattgg    1440
ctcttgattc tgtaattacg taatacatga aaaatgtttc atttggccta tgctcacttc    1500
atgcttataa acttttcctt gcaaattaat tggattagat gctccttcat agattcagat    1560
gcaatagatt tgcatgaaga aaataataga attcatgata gtaaaagat tgtatttttg     1620 tttgtttgtt tatgtttaaa agtctatatg ttgacaatag agttgctatc aactgtttca    1680
tttaggttta tgttttgtc aagttgctta ttctaagaga cattgtgatt atgacttgtc     1740
ttctctaacg tagtttagta ataaaagacg aaagaaattg atatccacaa gaaagagatg    1800
taagctgtaa cgtatcaaat ctcattaata actagtagta ttctcaacgc tatcgtttat    1860
ttctttcttt ggtttgccac tatatgccgc ttctctcctc ttttgtccca cgtactatcc    1920 attttttga aactttaata cgtaacact gaatattaat ttgttggttt aattaacttt      1980
gagtttgttt ttggtttatg cagaaacatg ggtgcaggtg gaagaatgca agtgtctcct    2040
ccctcgaaga agtctgaaac cgacaccatc aagcgcgtac cctgcgagac accgcccttc    2100
actgtcggag aactcaagaa agcaatccca ccgcactgtt tcaaacgctc gatccctcgc    2160
tctttctcct acctcatctg gacatcatc atagcctcct gcttctacta cgtcgccacc     2220
acttacttcc ctctcctccc tcaccctctc tcctacttcg cctggcctct ctactgggcc    2280
tgccagggct gcgtcctaac cggcgtctgg gtcatagccc acgagtgcgg ccaccacgcc    2340
ttcagcgact accagtggct tgacgacacc gtcggtctca tcttccactc cttcctcctc    2400
gtcccttact tctcctggaa gtacagtcat cgacgccacc attccaacac tggctccctc    2460
gagagagacg aagtgtttgt ccccaagaag aagtcagaca tcaagtggta cggcaagtac    2520
ctcaacaacc ctttgggacg caccgtgatg ttaacggttc agttcactct cggctggcct    2580
ttgtacttag ccttcaacgt ctcgggaaga ccttacgacg gcggcttcgc ttgccatttc    2640
caccctaacg ctcccatcta caacgaccgc gagcgtctcc agatatacat ctccgacgct    2700
ggcatcctcg ccgtctgcta cggtctctac cgctacgctg ctgtccaagg agttgcctcg    2760
atggtctgct tctacggagt cccgcttctg atagtcaacg ggttcttagt tttgatcact    2820
tacttgcagc acacgcatcc ttccctgcct cactacgatt cgtctgagtg ggattggttg    2880
aggggagcgt tggctaccgt tgacagagac tacgggatct tgaacaaggt cttccacaat    2940
atcacggaca cgcacgtggc gcatcacctg ttctcgacca tgccgcatta tcacgcgatg    3000
gaagctacca aggcgataaa gccgatactg gagagtatt atcagttcga tgggacgccg     3060
gtggttaagg cgatgtggag ggaggcgaag gagtgtatct atgtggaacc ggacaggcaa    3120
ggtgagaaga aggtgtgtt ctggtacaac aataagttat gaagcaaaga agaaactgaa     3180
cctttctctt ctatgattgt ctttgtttaa gaagctatgt ttctgtttca ataatcttaa    3240
ttatccattt tgttgtgttt tctgacattt tggctaaaat tatgtgatgt tggaagttag    3300
```

```
tgtctaaaat gtcttgtgtc tgtattgttc ttcttctcat cgctgttatg tttgggatcg    3360
ttgaaatgtg actttcggac tagtgaactc ttgttctcga actgtattaa tgtggatccc    3420
tgaaaagtgt aatggcttat cttcctctga aactactatt atgttctagt gaatcttgac    3480
ataaagcaac ttgtctttta ccaatgctat aagaaggttt gtgcacaaaa tgttttactc    3540
acctgaagtg aaccataaat ctaatcttcg ttacagttaa gttagtttga gttattgcgt    3600
tgtttggttg gcagatcacc tttaccactc atgtggttca gtctctttgt aaaa          3654

<210> SEQ ID NO 17
<211> LENGTH: 1440
<212> TYPE: DNA
<213> ORGANISM: Brassica rapa
<220> FEATURE:
<221> NAME/KEY: CDS
<222> LOCATION: (133)..(1287)

<400> SEQUENCE: 17
gagagattca ttaccaaaga gatagagaga gaaagagagg agacagagag agtttgagga      60
ggtgcttctt cgtagggttc atcgttatta acgttaaatc ttcatccccc tacgtcaacc    120
agctcaagaa ac atg ggt gca ggt gga aga atg caa gtg tct cct ccc tcg    171
              Met Gly Ala Gly Gly Arg Met Gln Val Ser Pro Pro Ser
                1               5                   10 aag aag tct gaa acc gac acc atc aag cgc gta ccc tgc gag aca ccg      219
Lys Lys Ser Glu Thr Asp Thr Ile Lys Arg Val Pro Cys Glu Thr Pro
 15                  20                  25 ccc ttc act gtc gga gaa ctc aag aaa gca atc cca ccg cac tgt ttc      267
Pro Phe Thr Val Gly Glu Leu Lys Lys Ala Ile Pro Pro His Cys Phe
 30                  35                  40                  45 aaa cgc tcg atc cct cgc tct ttc tcc tac ctc atc tgg gac atc atc      315
Lys Arg Ser Ile Pro Arg Ser Phe Ser Tyr Leu Ile Trp Asp Ile Ile
                 50                  55                  60 ata gcc tcc tgc ttc tac tac gtc gcc acc act tac ttc cct ctc ctc      363
Ile Ala Ser Cys Phe Tyr Tyr Val Ala Thr Thr Tyr Phe Pro Leu Leu
             65                  70                  75 cct cac cct ctc tcc tac ttc gcc tgg cct ctc tac tgg gcc tgc cag      411
Pro His Pro Leu Ser Tyr Phe Ala Trp Pro Leu Tyr Trp Ala Cys Gln
         80                  85                  90 ggc tgc gtc cta acc ggc gtc tgg gtc ata gcc cac gag tgc ggc cac      459
Gly Cys Val Leu Thr Gly Val Trp Val Ile Ala His Glu Cys Gly His
 95                 100                 105 cac gcc ttc agc gac tac cag tgg ctt gac gac acc gtc ggt ctc atc      507
His Ala Phe Ser Asp Tyr Gln Trp Leu Asp Asp Thr Val Gly Leu Ile
110                 115                 120                 125 ttc cac tcc ttc ctc ctc gtc cct tac ttc tcc tgg aag tac agt cat      555
Phe His Ser Phe Leu Leu Val Pro Tyr Phe Ser Trp Lys Tyr Ser His
                130                 135                 140 cga cgc cac cat tcc aac act ggc tcc ctc gag aga gac gaa gtg ttt      603
Arg Arg His His Ser Asn Thr Gly Ser Leu Glu Arg Asp Glu Val Phe
            145                 150                 155 gtc ccc aag aag aag tca gac atc aag tgg tac ggc aag tac ctc aac      651
Val Pro Lys Lys Lys Ser Asp Ile Lys Trp Tyr Gly Lys Tyr Leu Asn
        160                 165                 170 aac cct ttg gga cgc acc gtg atg tta acg gtt cag ttc act ctc ggc      699
Asn Pro Leu Gly Arg Thr Val Met Leu Thr Val Gln Phe Thr Leu Gly
    175                 180                 185 tgg cct ttg tac tta gcc ttc aac gtc tcg gga aga cct tac gac ggc      747
Trp Pro Leu Tyr Leu Ala Phe Asn Val Ser Gly Arg Pro Tyr Asp Gly
190                 195                 200                 205
```

-continued

| | |
|---|---|
| ggc ttc gct tgc cat ttc cac cct aac gct ccc atc tac aac gac cgc<br>Gly Phe Ala Cys His Phe His Pro Asn Ala Pro Ile Tyr Asn Asp Arg<br>             210                  215                  220 | 795 |
| gag cgt ctc cag ata tac atc tcc gac gct ggc atc ctc gcc gtc tgc<br>Glu Arg Leu Gln Ile Tyr Ile Ser Asp Ala Gly Ile Leu Ala Val Cys<br>         225                  230                  235 | 843 |
| tac ggt ctc tac cgc tac gct gct gtc caa gga gtt gcc tcg atg gtc<br>Tyr Gly Leu Tyr Arg Tyr Ala Ala Val Gln Gly Val Ala Ser Met Val<br>     240                  245                  250 | 891 |
| tgc ttc tac gga gtc ccg ctt ctg ata gtc aac ggg ttc tta gtt ttg<br>Cys Phe Tyr Gly Val Pro Leu Leu Ile Val Asn Gly Phe Leu Val Leu<br> 255                  260                  265 | 939 |
| atc act tac ttg cag cac acg cat cct tcc ctg cct cac tac gat tcg<br>Ile Thr Tyr Leu Gln His Thr His Pro Ser Leu Pro His Tyr Asp Ser<br>270                  275                  280                  285 | 987 |
| tct gag tgg gat tgg ttg agg gga gcg ttg gct acc gtt gac aga gac<br>Ser Glu Trp Asp Trp Leu Arg Gly Ala Leu Ala Thr Val Asp Arg Asp<br>             290                  295                  300 | 1035 |
| tac ggg atc ttg aac aag gtc ttc cac aat atc acg gac acg cac gtg<br>Tyr Gly Ile Leu Asn Lys Val Phe His Asn Ile Thr Asp Thr His Val<br>         305                  310                  315 | 1083 |
| gcg cat cac ctg ttc tcg acc atg ccg cat tat cac gcg atg gaa gct<br>Ala His His Leu Phe Ser Thr Met Pro His Tyr His Ala Met Glu Ala<br>     320                  325                  330 | 1131 |
| acc aag gcg ata aag ccg ata ctg gga gag tat tat cag ttc gat ggg<br>Thr Lys Ala Ile Lys Pro Ile Leu Gly Glu Tyr Tyr Gln Phe Asp Gly<br> 335                  340                  345 | 1179 |
| acg ccg gtg gtt aag gcg atg tgg agg gag gcg aag gag tgt atc tat<br>Thr Pro Val Val Lys Ala Met Trp Arg Glu Ala Lys Glu Cys Ile Tyr<br>350                  355                  360                  365 | 1227 |
| gtg gaa ccg gac agg caa ggt gag aag aaa ggt gtg ttc tgg tac aac<br>Val Glu Pro Asp Arg Gln Gly Glu Lys Lys Gly Val Phe Trp Tyr Asn<br>             370                  375                  380 | 1275 |
| aat aag tta tga agcaaagaag aaactgaacc tttctcttct atgattgtct<br>Asn Lys Leu | 1327 |
| ttgtttaaga agctatgttt ctgtttcaat aatcttaatt atccattttg ttgtgttttc | 1387 |
| tgacattttg gctaaaatta tgtgatgttg gaagttagtg tctaaaatgt ctt | 1440 |

<210> SEQ ID NO 18
<211> LENGTH: 384
<212> TYPE: PRT
<213> ORGANISM: Brassica rapa

<400> SEQUENCE: 18

Met Gly Ala Gly Gly Arg Met Gln Val Ser Pro Pro Ser Lys Lys Ser
1                 5                    10                 15

Glu Thr Asp Thr Ile Lys Arg Val Pro Cys Glu Thr Pro Pro Phe Thr
               20                    25                    30

Val Gly Glu Leu Lys Lys Ala Ile Pro Pro His Cys Phe Lys Arg Ser
          35                    40                    45

Ile Pro Arg Ser Phe Ser Tyr Leu Ile Trp Asp Ile Ile Ala Ser
50                   55                    60

Cys Phe Tyr Tyr Val Ala Thr Thr Tyr Phe Pro Leu Leu Pro His Pro
65                    70                    75                    80

Leu Ser Tyr Phe Ala Trp Pro Leu Tyr Trp Ala Cys Gln Gly Cys Val
               85                    90                    95

Leu Thr Gly Val Trp Val Ile Ala His Glu Cys Gly His His Ala Phe
          100                    105                   110

Ser Asp Tyr Gln Trp Leu Asp Thr Val Gly Leu Ile Phe His Ser
    115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
        210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
370                 375                 380

<210> SEQ ID NO 19
<211> LENGTH: 3654
<212> TYPE: DNA
<213> ORGANISM: Brassica rapa
<220> FEATURE:
<221> NAME/KEY: Intron
<222> LOCATION: (265)..(880)

<400> SEQUENCE: 19
tggcccagtt gaaataaga gaaagaggg gcccagttga aaaagaaga gatgtcattc       60 aaatgccttc ctctctcatc aatttaaaaa cggccctgcc tattgccact cccatctgac     120
cagacaaact acaacagatt gagaaagtgc cgagacaaga gagagaaaga gaagaaagat    180
agattctttg gaggagcttc attgtagggt tcatcgttat taacgtaaaa tctctccccc    240
caccctacgt cagcagcttt caaggtcttc ttcttcttct tctcattttc ctcttatttt    300
tatgaatttc tggtctgtgt ttatctcgtc gcgtccatct ctctagtatt tggaatttca    360
atcgataaat ctactaatct tattgcattc aactataaat ctgcttctct gtttccattt    420
gacaaatctt atcatgttcc tttcatctca cacattaata atgattactg tctatcgtct    480

```
cgcatatgca cccatgtttc ttctcaatta tgattagtgc cttcttcact atctatttag    540
aactctcttt attccatagg ttggttagaa aaatcaccta ttgttgaatc ttttgattga    600
cttgaccgat tcctattggt tcttggtact gtatataaat acttaataaa tggaagaacg    660
tttcattgac ttataataag ctcatcaact ttgtacaaat aaaacggatg atttaaatta    720
ggtaggtact tcagggttca gatgctcttt catagattca aatgcataaa gagtttgcat    780
gtacaaattt gattaaagat aaaaaaaaaa aaaaaaagtc tccctgtctc cataacatta    840
actttctttt cctttttttt tttttggtt ttctctacag aaacaaacat gggcgcaggt    900
ggaagaatgc aagtctctcc tccctccagc tcccccggaa ccaacaccct caaacgcgtc    960
ccctgcgaga caccaccatt cactctcgga gacctcaaga aagcaatccc acctcactgc   1020
ttcaaacgct ccatcccacg ctccttctcc tcttcgacat catcatctcc tcctcggctc   1080
ctccctctac cacctctcca cagcctactt ccctctccct tacctcgcct gacccctcta   1140
ctgggcctgc caaggctgcg tcctaacggg cctctgggtc atagcccacg agtgcggcca   1200
ccacgccttc agcgaccacc agtggctgga cgacgccgtc ggcctcgtct tccactcctt   1260
cctcctcgtc ccgtacttct cctggaagta catccatgac gccaccattc aacaccgga    1320 tccctcgata gggacgaagt gttcgtcccc aagaagaaat ccgacatcaa gtggtacggc   1380
aagtacctca caacccgct aggacgcacg gtgatgctaa ccgtccagtt caagctcggc    1440
tggccgttgt acttagcctt caacgtctcg ggaagacctt acagcgacgg tttcgcttgc   1500
catttccacc cgaacgctcc catctacaac gaccgcgagc gtctccagat atacatctct   1560
gacgctggcg tcctctccgt atgttacggt ctctaccgtt acgctgcttc gcgaggagta   1620
gcctctgtgg tctgtgtcta cggagttccg cttctaattg tcaactgttt cctcgtcttg   1680
atcacttact tgcagcacac gcacccttcg ctgcctcact atgattcttc cgagtgggat   1740
tggttgagag gagctttggc tactgtggat agagactatg gaatcttgaa caaggtgttc   1800
cataacatca cggacacgca cgtggcgcat catctgttct cgacgatgcc gcattataac   1860
gcgatggaag cgaccaaggc gataaagccg atactttgga gagtattacc agtttgatgg   1920
aacgccggcg gttaaggcga tgtggaggga ggcgaaggag tgtatctatg ttgaaccgga   1980
taggcaaggt gagaagaaag gtgtgttctg gtacaacaat aagttatgag gatgatgatg   2040
atgatgatga tagtggaagg acagagttaa aagatgttgt cgacttttct cttggtctgg   2100
tttagtcttt gttctaatta gaaactatgt attttttttg gtaggctgca ggcctacttt   2160
ttattcaaat caaaaacaaa acaactacag gcaaatttgt cgagttctgg acactccgtt   2220
acaatcttct aacaaaactg aagcaacatg ctctggagcc gactcaaaat aatgtaaacc   2280
aaacggtaaa gaaaacgcat agttagctaa tccatctgct agacaattag cctccctata   2340
cacgtgagaa attttgacta tccagtctct tgaaatgaag tcatagcaca aacgtactag   2400
gaaggatatg ggatgagaat catgaatccc tgtctgaaga aaaccgcca cactctctga    2460 atcaacttcc acctctagcc tccgaatacc acaatctcat gctatgcaca gtccatagta   2520
aacaccccac agttctgcca acggagccaa acaaataccc tatattaatcg caaaacctcc   2580 tttccacatt ccaaattcgt ctcgcacagc tcctcccgct gtggccagtc cagggttacc   2640
cctagatgct ccatcaatgt tcaatttaag ccagccatta acgggtcgct gccatgcgat   2700
ttgcttctcc acccggcccc tagcacaaga acgatctcgc aaatgcttat tgcttccaa    2760 cacttctctg acttttcttt taacaaactg cactctgtct cgacatgtcc ttgtttcacc   2820
aaatacatag ccacatcacc atttccagca ccaccacaca gtgaaggcaa aaagtgttgg   2880
```

-continued

```
ccattggtct ccattacccg gcttgtccct ccccagattc tcgtagagcc attgcaatag    2940
aggtaagcta agaaatgct gttgtctact cggaatcatg attttcaccc atattccaac     3000
tgctgcctga cagtctcgaa gaacatggag aatggtttcg tctccatctc tacacaacgg    3060
gcacacaaca ttatcactca aatgtctacg cttccgttcc atgttcgtca tgataacctg    3120
atgtgttacc aaccataaga agactcggac tcgttctgga gcaactagac accacaccag    3180
gctgtatagg gattccatgt ttggtctcag tacttcatct ctagtcagta aggcatacgc    3240
atatttaaca gaaaacaatc catctttgct ctcttcccac gacattctat ctcggactcc    3300
agtaacatca tcaatcacta cttcagctag tcttaactga ttctatactg acatatacgg    3360
ctcaatagct tgaagtagcc aactggttcc attctgccat aagtctcggg cccttgcttc    3420
taagatcggc tctgggatat gcaccatact tgattcgtat aggggctcgt tcaacaacca    3480
attgtctttc cagaaacgaa cccggcggcc gtcccccaag atccaacacg ttcccagaat    3540
aacaacttct ctgatacccca ccactaggct tctccaagtc ggtgaccagg tcccctggac    3600
tatcaaccat gttgggtcat atagctcccc actcggaact ttttccgcag cacc          3654
```

<210> SEQ ID NO 20
<211> LENGTH: 1243
<212> TYPE: DNA
<213> ORGANISM: Brassica rapa
<220> FEATURE:
<221> NAME/KEY: CDS
<222> LOCATION: (138)..(548)

<400> SEQUENCE: 20

```
agattgagaa agtgccgaga caagagagag aaagagaaga agatagatt ctttggagga     60 gcttcattgt agggttcatc gttattaacg taaaatctct ccccccaccc tacgtcagca    120
gctttcaaga aacaaac atg ggc gca ggt gga aga atg caa gtc tct cct        170
                   Met Gly Ala Gly Gly Arg Met Gln Val Ser Pro
                    1               5                  10 ccc tcc agc tcc ccc gga acc aac acc ctc aaa cgc gtc ccc tgc gag      218
Pro Ser Ser Ser Pro Gly Thr Asn Thr Leu Lys Arg Val Pro Cys Glu
            15                  20                  25 aca cca cca ttc act ctc gga gac ctc aag aaa gca atc cca cct cac      266
Thr Pro Pro Phe Thr Leu Gly Asp Leu Lys Lys Ala Ile Pro Pro His
        30                  35                  40 tgc ttc aaa cgc tcc atc cca cgc tcc ttc tcc tct tcg aca tca tca      314
Cys Phe Lys Arg Ser Ile Pro Arg Ser Phe Ser Ser Ser Thr Ser Ser
    45                  50                  55 tct cct cct cgg ctc ctc cct cta cca cct ctc cac agc cta ctt ccc      362
Ser Pro Pro Arg Leu Leu Pro Leu Pro Pro Leu His Ser Leu Leu Pro
60                  65                  70                  75 tct ccc tta cct cgc ctg acc cct cta ctg ggc ctg cca agg ctg cgt      410
Ser Pro Leu Pro Arg Leu Thr Pro Leu Leu Gly Leu Pro Arg Leu Arg
                80                  85                  90 cct aac ggg cct ctg ggt cat agc cca cga gtg cgg cca cca cgc ctt      458
Pro Asn Gly Pro Leu Gly His Ser Pro Arg Val Arg Pro Pro Arg Leu
            95                 100                 105 cag cga cca cca gtg gct gga cga cgc cgt cgg cct cgt ctt cca ctc      506
Gln Arg Pro Pro Val Ala Gly Arg Arg Arg Pro Arg Leu Pro Leu
        110                 115                 120 ctt cct cct cgt ccc gta ctt ctc ctg gaa gta cat cca tga              548
Leu Pro Pro Arg Pro Val Leu Leu Leu Glu Val His Pro
    125                 130                 135 cgccaccatt ccaacaccgg atccctcgat agggacgaag tgttcgtccc caagaagaaa    608
```

```
tccgacatca agtggtacgg caagtacctc aacaacccgc taggacgcac ggtgatgcta      668
accgtccagt tcaagctcgg ctggccgttg tacttagcct tcaacgtctc gggaagacct      728
tacagcgacg gtttcgcttg ccatttccac ccgaacgctc ccatctacaa cgaccgcgag      788
cgtctccaga tatacatctc tgacgctggc gtcctctccg tatgttacgg tctctaccgt      848
tacgctgctt cgcgaggagt agcctctgtg gtctgtgtct acggagttcc gcttctaatt      908
gtcaactgtt tcctcgtctt gatcacttac ttgcagcaca cgcacccttc gctgcctcac      968
tatgattctt ccgagtggga ttggttgaga ggagctttgg ctactgtgga tagagactat     1028
ggaatcttga acaaggtgtt ccataacatc acggacacgc acgtggcgca tcatctgttc     1088
tcgacgatgc cgcattataa cgcgatggaa gcgaccaagg cgataaagcc gatactttgg     1148
agagtattac cagtttgatg gaacgccggc ggttaaggcg atgtggaggg aggcgaagga     1208
gtgtatctat gttgaaccgg ataggcaagg tgaga                                1243

<210> SEQ ID NO 21
<211> LENGTH: 136
<212> TYPE: PRT
<213> ORGANISM: Brassica rapa

<400> SEQUENCE: 21

Met Gly Ala Gly Gly Arg Met Gln Val Ser Pro Pro Ser Ser Pro
1               5                   10                  15

Gly Thr Asn Thr Leu Lys Arg Val Pro Cys Glu Thr Pro Pro Phe Thr
            20                  25                  30

Leu Gly Asp Leu Lys Lys Ala Ile Pro Pro His Cys Phe Lys Arg Ser
        35                  40                  45

Ile Pro Arg Ser Phe Ser Ser Ser Thr Ser Ser Ser Pro Pro Arg Leu
    50                  55                  60

Leu Pro Leu Pro Pro Leu His Ser Leu Leu Pro Ser Pro Leu Pro Arg
65                  70                  75                  80

Leu Thr Pro Leu Leu Gly Leu Pro Arg Leu Arg Pro Asn Gly Pro Leu
                85                  90                  95

Gly His Ser Pro Arg Val Arg Pro Pro Arg Leu Gln Arg Pro Pro Val
            100                 105                 110

Ala Gly Arg Arg Arg Arg Pro Arg Leu Pro Leu Leu Pro Pro Arg Pro
        115                 120                 125

Val Leu Leu Leu Glu Val His Pro
    130                 135

<210> SEQ ID NO 22
<211> LENGTH: 4970
<212> TYPE: DNA
<213> ORGANISM: Brassica oleracea
<220> FEATURE:
<221> NAME/KEY: Intron
<222> LOCATION: (1765)..(2887)

<400> SEQUENCE: 22
gtaacagctg aataaatgaa atgaaatcat ggtaggtgat gatctttaaa aaaatgttga       60
aaataatgtg cgttgttaca atagcatctc ctaaccactt ttatatatgc ctctataata      120
gtatttagat ttagaactaa atcactgct tgcaaccta ctttatttct tcctttaaaa        180
taaaaattgt tattttcaca gaaatacatt cctttataat aaaacatac ttttttattc      240 acaaaataat cttttaattt tttatttta caattataac caaaataaat attttttaat      300
```

```
gaaaatgtac tgtttatata aatatataat catactttt atttacataa tagtttctat      360
aaaaatattc agtataaata atatcatagt tttatgaatg ttacactaaa ttggattggt      420
tttcaacttt cacaaataaa aaatactatt tataaaatta gaaaaaaata tatcaagact      480 attcttttt agaagaatac attggaaaca aatctatctc tattatataa tttctctgtt      540
ttagaaaaaa aatagagaaa tacattggag atggtttaag cggtagtaac acaaagaaaa      600
actctaatca tcttaagagc atctctaatg tacaattctg taacttcctc taaaatagag      660
atctctatta tagaagtgaa aatgttccaa tgtatgcttg tataatagaa ttcttctatt      720
ttaaaagaaa atatagagaa aaattacttt ttgcttttat atttaaaggt ggaaataaaa      780
tatctctata ttttgcccta taaatagatg aattctatta tacaagtata cattggaaca      840
tttttatttt tataatagag ttttctatt ttaggaaaaa atatagagat gtaaatagaa      900
atagagatga cttggagatg gtcttgcgta ggaaagagct agagctttga taaagtactt      960
aaatcaatta ctagtcggca gtcgctgcct acttgtgtac caccaaaatt aatttattat     1020
aatatatatt acgaatctcc aaagtacaca tcacacacac tctactcacg tgatctcaac     1080
cacaatgtct gcagatattt tttatagttt tttctcacat gggagagaag aagccaagca     1140
cgatcctcca tcctcaactt tatagcattt ttttcttttc tttccggcta ccacttgtga     1200
gtcgagtcga cgagggcgtt tccttatatt aaagtaaaga catcaaatac catcgtctta     1260
atgctaatta acgtaacgga tgagttctat aacataatcc aaactagtct ttgtgaacat     1320
taggattggg taaaccaata tttacatttt aaaaacaaaa tacaaaaaga aacgtgataa     1380
actttataaa agcaattata tgatcactgc atctttttcca cttttccgta aataaaataca     1440 taaaagtgcc gtaaatatca gatatttgga gtagaaaagt aataagaaaa gaaaatatga     1500
ggagagggaa taatggaggg ggcccacttg taaaaaagaa agaaaagaga tgtcactcaa     1560
tcgtctccca cgggcccccg tcaatttaaa cggcctgcct tctgcccaat cgcatcttat     1620
cagaaccaga cagattcatt accaaagaga tagagaaaga gagagagaga gagagagaga     1680
gagagtgagt ttgaggagga gcttcttcgt agggttcatc gttattaacg ttaaatcttc     1740
accccctacg tcagccagct caaggtccct ttcttcttcc atttcttttc attctacgtt     1800
gttttcaatc ttatgaaact ttctggtctg tgcttttctt atcgcttttc tattctatct     1860
atcatttttg catttcagtc gatttaattc tagatctgtt aatattaaac tatagatctg     1920
ttcttgattc tctgttttca tgtgtgaaat ctgatgctgt attaatctga ttatattgtc     1980
tataccgtgg agaatatcaa atgttgcatt tcatttgtc cgaatacaaa gtgtttgact     2040
ttcaatcgtt tttaattata tatatatata tatttttga tgggttggtg gagttgaaaa     2100
atcaccatag cagtctcacg tcctggtttt agaaatatcc tattcaaaat tatatatttg     2160
tttacttgtt ttagatctgg acctgagaca tataagtacc tatttgttga atctttgggt     2220
aaaaacttat gtctctgggt aaaatttgct gggagatttg accgattcct attggctctt     2280
gattctgtag ttacgtaata catgaaaaag tttcatttgg cctatgctca cttcatgctt     2340
ataaacgttt tcttgcaaat taattggatt agatgttatt tcatagattc agtcattcag     2400
atacaatgga gttgcatgaa gaaaataata gaattcgtga cagtaaaaaa gattgtattt     2460
ttgtttgttt gtttatgttt aaaagtctat atgttgacaa tagagttgct ctcaactgtt     2520
tcatttagct tctttttttg tcaagttgct tattcttaga gacattgtga ttatgacttg     2580
tcttctttaa cgtagtttag taataaaaga cgaaagaaat tgatatccac aagaaagaga     2640
tgtgagctgt agcgtatcaa atctcgttca tttactagta gtattctcaa cgctatcgtt     2700
```

```
tatttatttt tctttcgttg gtttgccact atatgccact tctctcctct ttgtcccacg   2760
tactatccat ttttttttgtg gtagtccatt ttcttgtaac ttataataac gtaactctga   2820
atcttttgtc tgtagattaa tttgttggtt taattaactt ttaagtcttt gcttttggct   2880
tatgcagaaa catgggtgca ggtggaagaa tgcaagtgtc tcctccctcc aagaagtctg   2940
aaaccgacac catcaagcgc gtaccctgcg agacaccgcc cttcactgtc ggagaactca   3000
agaaagcaat cccaccgcac tgtttcaaac gctcgatccc tcgctctttc tcctacctca   3060
tctgggacat catcatagcc tcctgcttct actacgtcgc caccacttac ttccctctcc   3120
tccctcaccc tctctcctac ttcgcctggc ctctctactg ggcctgccaa gggtgcgtcc   3180
taaccggcgt ctgggtcata gcccacgagt gcggccacca cgccttcagc gactaccagt   3240
ggcttgacga caccgtcggt ctcatcttcc actccttcct cctcgtccct tacttctcct   3300
ggaagtacag tcatcgacgc caccattcca acactggctc cctcgagaga gacgaagtgt   3360
ttgtccccaa gaagaagtca gacatcaagt ggtacggcaa gtacctcaac aacccctttgg  3420
gacgcaccgt gatgttaacg gttcagttca ctctcggctg gccgttgtac ttagccttca   3480
acgtctcggg aagaccttac gacggcggct tcgcttgcca tttccacccc aacgctccca   3540
tctacaacga ccgcgagcgt ctccagatat acatctccga cgctggcatc ctcgccgtct   3600
gctacggtct cttccgttac gccgccgcgc agggagtggc ctcgatggtc tgcttctacg   3660
gagtcccgct tctgattgtc aatggttttcc tcgtgttgat cacttacttg cagcacacgc   3720
atccttccct gcctcactac gattcgtccg agtgggattg gttgaggga gctttggcta    3780
ccgttgacag agactacgga atcttgaaca aggtcttcca caatattacc gacacgcacg   3840
tggcgcatca tctgttctcc acgatgccgc attatcacgc gatggaagct accaaggcga   3900
taaagccgat actgggagag tattatcagt tcgatgggac gccggtggtt aaggcgatgt   3960
ggagggaggc gaaggagtgt atctatgtgg aaccggacag gcaaggtgag aagaaaggtg   4020
tgttctggta caacaataag ttatgaggat atgatgatgg tgaaagaaca aagaagatat   4080
tgtcacgaac ctttctcttg ctgtctctgg tcgtctttgt tttaagaagc tatgttttcg   4140
tttcaataat cttaactatc cattttgttg tgttttctga cattttggct aagttatgtg   4200
atgtgggaca cgttagtgtc taaaatgtct ctgtgtctgt attgttcttc tcatctgtga   4260
ctttcggaca actaaactct tgttctcgaa ctacctcaat gtggcattaa tgaaagtgtt   4320
attgttgatt ttaatctgaa actgctatta tttagtgaat ttttacatca gccaacttgt   4380
ttgtttaaga cctaccaatg gtataagaaa gttttgtgtac taatgttcac catgtccata   4440
gtgttaagac ataaccatga tcttctgtcc aattaatttg cgtcgagtta tcgtgttatt   4500
tggcaccttt actatgtttt tttgtaaaga actccttaca gaatagcttt ttgtaaagaa   4560
ctacgtttta tcttttttgta agaacctttt aacaaaagcc aaattcatta ttacctggca   4620
caagaaaaaa ctctggtttc ttcctctttc tctgttttta gatttgagga gaacatgaa    4680
gatgaagaaa aagaaacaaa taaataacaa atctcttttt ttccattaac ggcagaaaca   4740
ccaaaacaga gtgacaacaa gaaacaaatg tagtgaggaa aaaccaaaga aaaagaata    4800
ttctgaaacc aactcgttga acatattcaa atacgaaaca atctttcatc caacggcgag   4860
cgtaatctag aagcatttcc tgtggactat cgatggccct gcctcatcat actcagcctt   4920
tgctatccac atctgcaaga ccaacattgt gtatcatagt cagcttaaaa              4970
```

<210> SEQ ID NO 23

```
<211> LENGTH: 1605
<212> TYPE: DNA
<213> ORGANISM: Brassica oleracea
<220> FEATURE:
<221> NAME/KEY: CDS
<222> LOCATION: (141)..(1295)

<400> SEQUENCE: 23
gacagattca ttaccaaaga gatagagaaa gagagagaga gagagagaga gagagagtga      60
gtttgaggag gagcttcttc gtagggttca tcgttattaa cgttaaatct tcaccccta     120 cgtcagccag ctcaagaaac atg ggt gca ggt gga aga atg caa gtg tct cct    173
                     Met Gly Ala Gly Gly Arg Met Gln Val Ser Pro
                       1               5                  10 ccc tcc aag aag tct gaa acc gac acc atc aag cgc gta ccc tgc gag      221
Pro Ser Lys Lys Ser Glu Thr Asp Thr Ile Lys Arg Val Pro Cys Glu
             15                  20                  25 aca ccg ccc ttc act gtc gga gaa ctc aag aaa gca atc cca ccg cac      269
Thr Pro Pro Phe Thr Val Gly Glu Leu Lys Lys Ala Ile Pro Pro His
         30                  35                  40 tgt ttc aaa cgc tcg atc cct cgc tct ttc tcc tac ctc atc tgg gac      317
Cys Phe Lys Arg Ser Ile Pro Arg Ser Phe Ser Tyr Leu Ile Trp Asp
     45                  50                  55 atc atc ata gcc tcc tgc ttc tac tac gtc gcc acc act tac ttc cct      365
Ile Ile Ile Ala Ser Cys Phe Tyr Tyr Val Ala Thr Thr Tyr Phe Pro
 60                  65                  70                  75 ctc ctc cct cac cct ctc tcc tac ttc gcc tgg cct ctc tac tgg gcc      413
Leu Leu Pro His Pro Leu Ser Tyr Phe Ala Trp Pro Leu Tyr Trp Ala
                 80                  85                  90 tgc caa ggg tgc gtc cta acc ggc gtc tgg gtc ata gcc cac gag tgc      461
Cys Gln Gly Cys Val Leu Thr Gly Val Trp Val Ile Ala His Glu Cys
             95                 100                 105 ggc cac cac gcc ttc agc gac tac cag tgg ctt gac gac acc gtc ggt      509
Gly His His Ala Phe Ser Asp Tyr Gln Trp Leu Asp Asp Thr Val Gly
        110                 115                 120 ctc atc ttc cac tcc ttc ctc ctc gtc cct tac ttc tcc tgg aag tac      557
Leu Ile Phe His Ser Phe Leu Leu Val Pro Tyr Phe Ser Trp Lys Tyr
    125                 130                 135 agt cat cga cgc cac cat tcc aac act ggc tcc ctc gag aga gac gaa      605
Ser His Arg Arg His His Ser Asn Thr Gly Ser Leu Glu Arg Asp Glu
140                 145                 150                 155 gtg ttt gtc ccc aag aag aag tca gac atc aag tgg tac ggc aag tac      653
Val Phe Val Pro Lys Lys Lys Ser Asp Ile Lys Trp Tyr Gly Lys Tyr
                160                 165                 170 ctc aac aac cct ttg gga cgc acc gtg atg tta acg gtt cag ttc act      701
Leu Asn Asn Pro Leu Gly Arg Thr Val Met Leu Thr Val Gln Phe Thr
            175                 180                 185 ctc ggc tgg ccg ttg tac tta gcc ttc aac gtc tcg gga aga cct tac      749
Leu Gly Trp Pro Leu Tyr Leu Ala Phe Asn Val Ser Gly Arg Pro Tyr
        190                 195                 200 gac ggc ggc ttc gct tgc cat ttc cac ccc aac gct ccc atc tac aac      797
Asp Gly Gly Phe Ala Cys His Phe His Pro Asn Ala Pro Ile Tyr Asn
    205                 210                 215 gac cgc gag cgt ctc cag ata tac atc tcc gac gct ggc atc ctc gcc      845
Asp Arg Glu Arg Leu Gln Ile Tyr Ile Ser Asp Ala Gly Ile Leu Ala
220                 225                 230                 235 gtc tgc tac ggt ctc ttc cgt tac gcc gcc gcg cag gga gtg gcc tcg      893
Val Cys Tyr Gly Leu Phe Arg Tyr Ala Ala Ala Gln Gly Val Ala Ser
                240                 245                 250 atg gtc tgc ttc tac gga gtc ccg ctt ctg att gtc aat ggt ttc ctc      941
Met Val Cys Phe Tyr Gly Val Pro Leu Leu Ile Val Asn Gly Phe Leu
```

```
                255                 260                 265
gtg ttg atc act tac ttg cag cac acg cat cct tcc ctg cct cac tac    989
Val Leu Ile Thr Tyr Leu Gln His Thr His Pro Ser Leu Pro His Tyr
        270                 275                 280 gat tcg tcc gag tgg gat tgg ttg agg gga gct ttg gct acc gtt gac    1037
Asp Ser Ser Glu Trp Asp Trp Leu Arg Gly Ala Leu Ala Thr Val Asp
285                 290                 295 aga gac tac gga atc ttg aac aag gtc ttc cac aat att acc gac acg    1085
Arg Asp Tyr Gly Ile Leu Asn Lys Val Phe His Asn Ile Thr Asp Thr
300                 305                 310                 315 cac gtg gcg cat cat ctg ttc tcc acg atg ccg cat tat cac gcg atg    1133
His Val Ala His His Leu Phe Ser Thr Met Pro His Tyr His Ala Met
            320                 325                 330 gaa gct acc aag gcg ata aag ccg ata ctg gga gag tat tat cag ttc    1181
Glu Ala Thr Lys Ala Ile Lys Pro Ile Leu Gly Glu Tyr Tyr Gln Phe
                335                 340                 345 gat ggg acg ccg gtg gtt aag gcg atg tgg agg gag gcg aag gag tgt    1229
Asp Gly Thr Pro Val Val Lys Ala Met Trp Arg Glu Ala Lys Glu Cys
            350                 355                 360 atc tat gtg gaa ccg gac agg caa ggt gag aag aaa ggt gtg ttc tgg    1277
Ile Tyr Val Glu Pro Asp Arg Gln Gly Glu Lys Lys Gly Val Phe Trp
365                 370                 375 tac aac aat aag tta tga ggatatgatg atggtgaaag aacaaagaag           1325
Tyr Asn Asn Lys Leu
380 atattgtcac gaacctttct cttgctgtct ctggtcgtct ttgttttaag aagctatgtt  1385 ttcgtttcaa taatcttaac tatccatttt gttgtgtttt ctgacatttt ggctaagtta  1445 tgtgatgtgg gacacgttag tgtctaaaat gtctctgtgt ctgtattgtt cttctcatct  1505 gtgactttcg gacaactaaa ctcttgttct cgaactacct caatgtggca ttaatgaaag  1565 tgttattgtt gattttaatc tgaaactgct attatttagt                        1605

<210> SEQ ID NO 24
<211> LENGTH: 384
<212> TYPE: PRT
<213> ORGANISM: Brassica oleracea

<400> SEQUENCE: 24

Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140
```

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380

<210> SEQ ID NO 25
<211> LENGTH: 3883
<212> TYPE: DNA
<213> ORGANISM: Brassica oleracea
<220> FEATURE:
<221> NAME/KEY: Intron
<222> LOCATION: (816)..(1869)

<400> SEQUENCE: 25
attactagtt tcttttcgtc tgccaacaaa tttgattatt ataagtatca aagatgatta      60
cacatacata acaaattgta ataagaaaaa gaaagagag agaaatcctc acgtgagcat     120
caccacaatt tgtctgttac atatttctgt aagttcttgt gtgttcacat gggcaaaagt     180
gagaagaagc caaacacgat actccatttt caggcatcaa ctaccatctt cttcttcttc     240
ttctttatca agttgtttct aatgtcatat taagaaatga tacatgattg acttacgtag     300
agaaaaactg attcaaacaa gtaccgcatg tgtcattgcg ttccaaagtg attaagtcaa     360
taacatgata cgaccttttt tattacatta catacataac caagataacg tggacgagaa     420
aaagagagaa cgtcgtagta atatcacctt tcatcactc taactttac attttggtaa     480 attctaaatt aatggtcgtt ccttgagtta aatatcagat attttgaaca gaggggccca     540
gttgtaaaaa taagagaaaa gaggggccag ttgtaagaat aagagatgtc attcaaatgc     600
cttcctgtct ctcatcaatt taaaacggc cctgcctatt gccactcgca tctgaccaga     660
caaaccacaa cagattgaga gaagtgccga gacaagagag agagagagag aaagagaaga     720

```
gagagagata gattctttgg aggagcttca ttgtagggtt catcgttatt aacgtaaaat    780
ctctctcccc ccaccctacg tcagcagctt tcagggtccc cttcttcttc ttcttcttct    840
cattttcctc ttattttat gaattcctgg tctgtgttca tctcgtccat ctctctagca    900
gtctagcatt tggcatttaa atcgatagat ctgccagtct ttattgcatt caactaaaga    960
tctgttcctc tgtttccatt tgacaaatct tgtgtcatgt ttctttcatc tcaccgttaa   1020
ataatgatta ctgtctatcg tctagcatat gaaatgttgc aactttctat ctattcagaa   1080 atcttttat tcaataggtt ggtgaaatag aaaaggtcaa atctccaaaa tagcaacttt   1140
ctaagtttat atcacaaaaa tagcactcaa aaattaaaat gaccaaaata ttattttatc   1200
ttttgaaaat tttaattttt ttattttca aatttgaaa tcttatcccc aaaacctcat   1260
ttctcaactc taaaccctaa actctgaacc ataaacccta aacccaaaac tctaaaccct   1320
aaaccctaaa ccctaaatcc taaaccccac cctttaactc taaaccctaa gtttgtgact   1380
tttgataaaa cattaagtac tattttgtga cttttgacct tgagtgctag tttgggaaca   1440
aaaacttgat ttagtgttat ttttgtcttt ttctcatctt atttccttt ccttgtattt   1500 attctaaatg atggatgtcc ataaccggtt cggtccataa ccggcccaat acctagagag   1560
agagaggttg ccacgcatgg aaagagcaat ataaaaatca cttattgttg aacctttgat   1620
agatttgacc gattcctact ggttcttgct actgttattt cttaataaat ggaagaacgt   1680
ttcattgact tataagctca tcaactttgt acaaataaaa cggatgattt aaagtaggta   1740
ggtacttcag ggtttagatg ttctttata gattcaaatg catgaagagt tgcatataca   1800
actttgatta aaggataaaa agtctccgtc ctccataaca ttattattat ttttggttt   1860 tctctacaga aacaaacatg ggcgcaggtg gaagaatgca agtctctcct ccctccagct   1920
cccccgaaac caaaccctc aaacgcgtcc cctgcgagac accacccttc actctcggag   1980
acctcaagaa agcaatccca cctcactgct tcaaacgctc catccctcgc tccttctcct   2040
acctcctctt cgacatcctc gtctcctcct ccctctacca cctctccaca gcctacttcc   2100
ctctcctccc ccaccctctc ccttacctcg cctggcccct ctactgggcc tgccaaggct   2160
gcgtcctaac gggcctctgg gtcatcgccc acgaatgcgg ccaccacgcc ttcagcgacc   2220
accagtggct ggacgacgcc gtgggcctcg tcttccactc cttcctcctc gtcccttact   2280
tctcctggaa gtacagccat cgacgccacc attccaacac cggatccctc gagagggatg   2340
aagtgttcgt ccccaagaag aaatccgaca tcaagtggta cggaaagtac ctcaacaacc   2400
cgctaggacg cacggtgatg ctaaccgtcc agttcacgct cggctggccg ttgtacttag   2460
ccttcaacgt ctctggaaga ccttacagcg acggtttcgc ttgccatttc caccgaacg   2520 ctcccatcta caacgaccgc gagcgtctcc agatatacat ctctgacgct ggcgtcctct   2580
ccgtatgtta cggtctctac cgctacgctg ttcgcgagg agtggcctcg atggtctgtg   2640
tctacggagt tccgcttatg attgtcaact gtttcctcgt cttgatcact tacttgcagc   2700
acacgcaccc ttcgctgcct cactatattc ttcggagtgg gattggttga gaggagcttt   2760
ggctactgtg gatagagact atggaatctt gaacaaggtg tttcataaca tcacggacac   2820
gcacgtggcg catcatctgt tctcgacgat gccgcattat aacgcgatgg aagcgaccaa   2880
ggcgataaag ccgatacttg gagagtatta ccagtttgat ggaacgccgg tggttaaggc   2940
gatgtggagg gaggcgaagg agtgtatcta tgttgaaccg gataggcaag gtgagaagaa   3000
aggtgtgttc tggtacaaca ataagttatg aggatgatga tgatgatgat gatgatgatg   3060
```

```
atgatgatga tgatgatgat gatgatgatg atgatgatga tgatgatgat gatgatgatg    3120
atgatgatga tgatgatgat gatgatgatg atgatgatga tgatgatgat gatgatgatg    3180
atgatgatga tgatgatgat gatgatgatg atgatgatga tgatgatgat gatgatgatg    3240
atgatgatga tgatgatgat gatgatgatg atgatgatga tgatgatgat gatgatgatg    3300
atgatgatga tgatgatgat gatgatgatg atgatgatga tgatgatgat gatgatgatg    3360
atgatgatga tgatgatgat gatgatgatg atgatgatga tgatgatgat gatgatgatg    3420
atgatgatga tgatgatgat gatgatgatg atgatgatga tgatgatgat gatgatgatg    3480
atgatgatga tgatgatgat gatgatgatg atgatgatga tgatgatgat gatgatgatg    3540
gtggaaggac agagttaaaa gttgttgtcg acttttctct tggtctggtt tagtctttgt    3600
tctaattaga aactatgtat ttgttacagt aatgttatta ttgtctcatt ttgttgtgtt    3660 atgacattt ggcttaaatt aagtatgttt tagcattttt cttgcttaaa ccaaaaaaaa    3720
atgtgaatgg gggaatcaaa gatcatattg tgctctacct acagaaccta atatgctaag    3780
ttatggggcc agtaaaagca tcttaaaaag aaaattcacc atccgtcctc tatattattc    3840
tttgcttacc tttcattgat cattgtgaat ttatctgatt cta                      3883

<210> SEQ ID NO 26
<211> LENGTH: 1962
<212> TYPE: DNA
<213> ORGANISM: Brassica oleracea
<220> FEATURE:
<221> NAME/KEY: CDS
<222> LOCATION: (153)..(1025)

<400> SEQUENCE: 26
agattgagag aagtgccgag acaagagaga gagagagaga aagagaagag agagagatag     60
attctttgga ggagcttcat tgtagggttc atcgttatta acgtaaaatc tctctccccc    120
```

| | | | | | | | | | | | | | | | | | |
|---|---|---|---|---|---|---|---|---|---|---|---|---|---|---|---|---|---|
| caccctacgt cagcagcttt caggaaacaa ac | atg<br>Met<br>1 | ggc<br>Gly | gca<br>Ala | ggt<br>Gly | gga<br>Gly | aga<br>Arg<br>5 | atg<br>Met | | | | | | | | | | 173 |

```
caa gtc tct cct ccc tcc agc tcc ccc gaa acc aaa acc ctc aaa cgc     221
Gln Val Ser Pro Pro Ser Ser Ser Pro Glu Thr Lys Thr Leu Lys Arg
    10                  15                  20 gtc ccc tgc gag aca cca ccc ttc act ctc gga gac ctc aag aaa gca    269
Val Pro Cys Glu Thr Pro Pro Phe Thr Leu Gly Asp Leu Lys Lys Ala
 25                  30                  35 atc cca cct cac tgc ttc aaa cgc tcc atc cct cgc tcc ttc tcc tac    317
Ile Pro Pro His Cys Phe Lys Arg Ser Ile Pro Arg Ser Phe Ser Tyr
 40                  45                  50                  55 ctc ctc ttc gac atc ctc gtc tcc tcc tcc ctc tac cac ctc tcc aca    365
Leu Leu Phe Asp Ile Leu Val Ser Ser Ser Leu Tyr His Leu Ser Thr
                 60                  65                  70 gcc tac ttc cct ctc ctc ccc cac cct ctc cct tac ctc gcc tgg ccc    413
Ala Tyr Phe Pro Leu Leu Pro His Pro Leu Pro Tyr Leu Ala Trp Pro
         75                  80                  85 ctc tac tgg gcc tgc caa ggc tgc gtc cta acg ggc ctc tgg gtc atc    461
Leu Tyr Trp Ala Cys Gln Gly Cys Val Leu Thr Gly Leu Trp Val Ile
         90                  95                 100 gcc cac gaa tgc ggc cac cac gcc ttc agc gac cac cag tgg ctg gac    509
Ala His Glu Cys Gly His His Ala Phe Ser Asp His Gln Trp Leu Asp
            105                 110                 115 gac gcc gtg ggc ctc gtc ttc cac tcc ttc ctc ctc gtc cct tac ttc    557
Asp Ala Val Gly Leu Val Phe His Ser Phe Leu Leu Val Pro Tyr Phe
120                 125                 130                 135
```

| | | | | | | | | | | | | | | |
|---|---|---|---|---|---|---|---|---|---|---|---|---|---|---|
| tcc | tgg | aag | tac | agc | cat | cga | cgc | cac | cat | tcc | aac | acc | gga | tcc | ctc | 605 |
| Ser | Trp | Lys | Tyr | Ser | His | Arg | Arg | His | His | Ser | Asn | Thr | Gly | Ser | Leu |
| | | | 140 | | | | | 145 | | | | | 150 | | |

```
tcc tgg aag tac agc cat cga cgc cac cat tcc aac acc gga tcc ctc      605
Ser Trp Lys Tyr Ser His Arg Arg His His Ser Asn Thr Gly Ser Leu
            140                 145                 150 gag agg gat gaa gtg ttc gtc ccc aag aag aaa tcc gac atc aag tgg      653
Glu Arg Asp Glu Val Phe Val Pro Lys Lys Lys Ser Asp Ile Lys Trp
            155                 160                 165 tac gga aag tac ctc aac aac ccg cta gga cgc acg gtg atg cta acc      701
Tyr Gly Lys Tyr Leu Asn Asn Pro Leu Gly Arg Thr Val Met Leu Thr
            170                 175                 180 gtc cag ttc acg ctc ggc tgg ccg ttg tac tta gcc ttc aac gtc tct      749
Val Gln Phe Thr Leu Gly Trp Pro Leu Tyr Leu Ala Phe Asn Val Ser
            185                 190                 195 gga aga cct tac agc gac ggt ttc gct tgc cat ttc cac ccg aac gct      797
Gly Arg Pro Tyr Ser Asp Gly Phe Ala Cys His Phe His Pro Asn Ala
200             205                 210                 215 ccc atc tac aac gac cgc gag cgt ctc cag ata tac atc tct gac gct      845
Pro Ile Tyr Asn Asp Arg Glu Arg Leu Gln Ile Tyr Ile Ser Asp Ala
                220                 225                 230 ggc gtc ctc tcc gta tgt tac ggt ctc tac cgc tac gct ggt tcg cga      893
Gly Val Leu Ser Val Cys Tyr Gly Leu Tyr Arg Tyr Ala Gly Ser Arg
                235                 240                 245 gga gtg gcc tcg atg gtc tgt gtc tac gga gtt ccg ctt atg att gtc      941
Gly Val Ala Ser Met Val Cys Val Tyr Gly Val Pro Leu Met Ile Val
            250                 255                 260 aac tgt ttc ctc gtc ttg atc act tac ttg cag cac acg cac cct tcg      989
Asn Cys Phe Leu Val Leu Ile Thr Tyr Leu Gln His Thr His Pro Ser
            265                 270                 275 ctg cct cac tat att ctt cgg agt ggg att ggt tga gaggagcttt         1035
Leu Pro His Tyr Ile Leu Arg Ser Gly Ile Gly
280                 285                 290 ggctactgtg gatagagact atggaatctt gaacaaggtg tttcataaca tcacggacac   1095
gcacgtggcg catcatctgt tctcgacgat gccgcattat aacgcgatgg aagcgaccaa   1155
ggcgataaag ccgatacttg gagagtatta ccagtttgat ggaacgccgg tggttaaggc   1215
gatgtggagg gaggcgaagg agtgtatcta tgttgaaccg gataggcaag gtgagaagaa   1275
aggtgtgttc tggtacaaca ataagttatg aggatgatga tgatgatgat gatgatgatg   1335
atgatgatga tgatgatgat gatgatgatg atgatgatga tgatgatgat gatgatgatg   1395
atgatgatga tgatgatgat gatgatgatg atgatgatga tgatgatgat gatgatgatg   1455
atgatgatga tgatgatgat gatgatgatg atgatgatga tgatgatgat gatgatgatg   1515
atgatgatga tgatgatgat gatgatgatg atgatgatga tgatgatgat gatgatgatg   1575
atgatgatga tgatgatgat gatgatgatg atgatgatga tgatgatgat gatgatgatg   1635
atgatgatga tgatgatgat gatgatgatg atgatgatga tgatgatgat gatgatgatg   1695
atgatgatga tgatgatgat gatgatgatg atgatgatga tgatgatgat gatgatgatg   1755
atgatgatga tgatgatgat gatgatgatg atgatgatga tgatgatgat gatgatgatg   1815
gtggaaggac agagttaaaa gttgttgtcg acttttctct tggtctggtt tagtctttgt   1875
tctaattaga aactatgtat ttgttacagt aatgttatta ttgtctcatt ttgttgtgtt   1935
atgacatttt ggcttaaatt aagtatg                                      1962
```

<210> SEQ ID NO 27
<211> LENGTH: 290
<212> TYPE: PRT
<213> ORGANISM: Brassica oleracea

<400> SEQUENCE: 27

-continued

```
Met Gly Ala Gly Gly Arg Met Gln Val Ser Pro Pro Ser Ser Ser Pro
1               5                   10                  15

Glu Thr Lys Thr Leu Lys Arg Val Pro Cys Glu Thr Pro Pro Phe Thr
            20                  25                  30

Leu Gly Asp Leu Lys Lys Ala Ile Pro Pro His Cys Phe Lys Arg Ser
        35                  40                  45

Ile Pro Arg Ser Phe Ser Tyr Leu Leu Phe Asp Ile Leu Val Ser Ser
50                  55                  60

Ser Leu Tyr His Leu Ser Thr Ala Tyr Phe Pro Leu Leu Pro His Pro
65                  70                  75                  80

Leu Pro Tyr Leu Ala Trp Pro Leu Tyr Trp Ala Cys Gln Gly Cys Val
                85                  90                  95

Leu Thr Gly Leu Trp Val Ile Ala His Glu Cys Gly His His Ala Phe
            100                 105                 110

Ser Asp His Gln Trp Leu Asp Asp Ala Val Gly Leu Val Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Ser Asp Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Val Leu Ser Val Cys Tyr Gly Leu
225                 230                 235                 240

Tyr Arg Tyr Ala Gly Ser Arg Gly Val Ala Ser Met Val Cys Val Tyr
                245                 250                 255

Gly Val Pro Leu Met Ile Val Asn Cys Phe Leu Val Leu Ile Thr Tyr
            260                 265                 270

Leu Gln His Thr His Pro Ser Leu Pro His Tyr Ile Leu Arg Ser Gly
        275                 280                 285

Ile Gly
    290
```

<210> SEQ ID NO 28
<211> LENGTH: 42
<212> TYPE: DNA
<213> ORGANISM: artificial
<220> FEATURE:
<223> OTHER INFORMATION: primer

<400> SEQUENCE: 28
gaaggtgacc aagttcatgc tgtagtcgct gaaggcgtgg tg                    42

<210> SEQ ID NO 29
<211> LENGTH: 42
<212> TYPE: DNA
<213> ORGANISM: artificial
<220> FEATURE:
<223> OTHER INFORMATION: primer

<400> SEQUENCE: 29

```
gaaggtcgga gtcaacggat tgtagtcgct gaaggcgtgg ta                          42
```

<210> SEQ ID NO 30
<211> LENGTH: 19
<212> TYPE: DNA
<213> ORGANISM: artificial
<220> FEATURE:
<223> OTHER INFORMATION: primer

<400> SEQUENCE: 30

```
tctctactgg gcctgccag                                                   19
```

<210> SEQ ID NO 31
<211> LENGTH: 41
<212> TYPE: DNA
<213> ORGANISM: artificial
<220> FEATURE:
<223> OTHER INFORMATION: primer

<400> SEQUENCE: 31

```
gaaggtgacc aagttcatgc tcgcactcgt gggctatgac c                          41
```

<210> SEQ ID NO 32
<211> LENGTH: 42
<212> TYPE: DNA
<213> ORGANISM: artificial
<220> FEATURE:
<223> OTHER INFORMATION: primer

<400> SEQUENCE: 32

```
gaaggtcgga gtcaacggat tccgcactcg tgggctatga ct                         42
```

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33

```
tctactgggc ctgccaaggg                                                  20
```

<210> SEQ ID NO 34
<211> LENGTH: 41
<212> TYPE: DNA
<213> ORGANISM: artificial
<220> FEATURE:
<223> OTHER INFORMATION: primer

<400> SEQUENCE: 34

```
gaaggtgacc aagttcatgc tgtccagttc acgctcggct g                          41
```

<210> SEQ ID NO 35
<211> LENGTH: 42
<212> TYPE: DNA
<213> ORGANISM: artificial
<220> FEATURE:
<223> OTHER INFORMATION: primer

<400> SEQUENCE: 35

```
gaaggtcgga gtcaacggat tcgtccagtt cacgctcggc ta                         42
```

<210> SEQ ID NO 36
<211> LENGTH: 21
<212> TYPE: DNA

```
<213> ORGANISM: artificial
<220> FEATURE:
<223> OTHER INFORMATION: primer

<400> SEQUENCE: 36
ccgtcgctgt aaggtcttcc a                                          21

<210> SEQ ID NO 37
<211> LENGTH: 2985
<212> TYPE: DNA
<213> ORGANISM: Brassica napus
<220> FEATURE:
<221> NAME/KEY: CDS
<222> LOCATION: (1)..(281)
<220> FEATURE:
<221> NAME/KEY: CDS
<222> LOCATION: (838)..(927)
<220> FEATURE:
<221> NAME/KEY: CDS
<222> LOCATION: (1463)..(1529)
<220> FEATURE:
<221> NAME/KEY: CDS
<222> LOCATION: (1931)..(2023)
<220> FEATURE:
<221> NAME/KEY: CDS
<222> LOCATION: (2128)..(2313)
<220> FEATURE:
<221> NAME/KEY: CDS
<222> LOCATION: (2391)..(2471)
<220> FEATURE:
<221> NAME/KEY: CDS
<222> LOCATION: (2559)..(2696)
<220> FEATURE:
<221> NAME/KEY: CDS
<222> LOCATION: (2791)..(2985)

<400> SEQUENCE: 37
```

| | | | | | | | | | | | | | | | | |
|---|---|---|---|---|---|---|---|---|---|---|---|---|---|---|---|---|
| atg | gtt | gtc | gct | atg | gac | cag | cgt | agc | aat | gcg | aac | gga | gac | gaa | agg | 48 |
| Met | Val | Val | Ala | Met | Asp | Gln | Arg | Ser | Asn | Ala | Asn | Gly | Asp | Glu | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | gat | ccg | agc | gca | caa | cca | ccg | ttc | aag | atc | gga | gat | ata | agg | gcg | 96 |
| Phe | Asp | Pro | Ser | Ala | Gln | Pro | Pro | Phe | Lys | Ile | Gly | Asp | Ile | Arg | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| gcc | att | cct | aag | cat | tgt | tgg | gta | aag | agt | cct | ttg | aga | tcc | atg | agc | 144 |
| Ala | Ile | Pro | Lys | His | Cys | Trp | Val | Lys | Ser | Pro | Leu | Arg | Ser | Met | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| tat | gtc | gcc | aga | gac | att | ttc | gcc | gtc | gtg | gct | ctt | gcc | gtc | gcc | gcc | 192 |
| Tyr | Val | Ala | Arg | Asp | Ile | Phe | Ala | Val | Val | Ala | Leu | Ala | Val | Ala | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| gtg | tat | ttt | gat | agc | tgg | ttc | ttt | tgg | cct | ctt | tat | tgg | gcc | gcc | caa | 240 |
| Val | Tyr | Phe | Asp | Ser | Trp | Phe | Phe | Trp | Pro | Leu | Tyr | Trp | Ala | Ala | Gln | |
| 65 | | | | | 70 | | | | | 75 | | | | | 80 | |

| | | | | | | | | | | | | |
|---|---|---|---|---|---|---|---|---|---|---|---|---|
| gga | acc | ctg | ttc | tgg | gct | atc | ttc | gta | ctc | ggc | cac | gac | tg | 281 |
| Gly | Thr | Leu | Phe | Trp | Ala | Ile | Phe | Val | Leu | Gly | His | Asp | Cys | |
| | | | | 85 | | | | | 90 | | | | | |

```
gtaatttaat ttttctttca acttcttaat tttgatatgt ttatatgttt ttttcgtttt    341
ttgcattgtc tttgatttct tgaccgtacg ttcgatatga gattttcact gacttcaaga    401
tttgattctc ttcaggttta ctttttttcaa tttaattat tatgttcacc caatttggcc    461 tatttttaaaa gcaaaagggg atctaagatt tttaattctt tgtttttttt ttgttctttt    521
tcattagtcg taacactcct aactaaacat ctttttcttt cctataatta ctgttgtttc    581
cgcattttat ggatctacgt ttgaaatttt caataaacac acattttatt gttttctgta    641
acaatttaat tactgtatat tggttctttt aattattgtg tgttgttcca atctattttc    701
gaaatatagt catgtgacac gtcatattct attttttgtta ccttgttgaa acgtttgaat    761
```

```
tgagtaaagt tcagttaaca ttgtgcaata aatgataaat gtgtttatga tgtaaaattt      821
aatttgaata atacag t gga cat ggg agc ttc tca gac att cct ctt ctg        871
                    Gly His Gly Ser Phe Ser Asp Ile Pro Leu Leu
                     95              100                 105 aat act gcg gtt ggt cat att ctt cat tcc ttc att ctc gtt cca tac        919
Asn Thr Ala Val Gly His Ile Leu His Ser Phe Ile Leu Val Pro Tyr
                110                 115                 120 cat ggt tg gtaagtcatt tattttaact tcttttttca tgcaaattta                 967
His Gly Trp ttcttgtttt cgtatttctt acattttcct tgtcattctt ggtgcatgtt agcaaacagt      1027
aatctgataa ctgaaaatat attaattttt catagtaaaa aatgcatgt gactaaaagt       1087 ctaaaagcat caaaatcttt agcatccatg aaaaagaaac aaaacttta tttaatgcta       1147 tgggcctatt tatggtccaa ttagctatta tcatatgaca tgtccttgaa taaattaatg      1207
tataagttta ataatattta tatttttg ttttaatggc ttatttatt gttaaatgga        1267 tacatcagct tgaaatatct atgaacatgc atcattttcc taagatacat ttgtttgttg      1327
ctcaaaaaat aaataactag ttaaacgagt gagattctta gcatctgcct cgaaaacgat      1387
atgttattga caattccaat ttcattttta tgaaaataaa ataatagttt atttataat       1447 tggggttggt tgcag g aga ata agc cat cgg aca cac cac cag aac cat         1496
                  Arg Ile Ser His Arg Thr His His Gln Asn His
                      125                 130                 135 ggc cat gtt gaa aac gac gag tct tgg gtt ccg gtaatctttc cctctctcat      1549
Gly His Val Glu Asn Asp Glu Ser Trp Val Pro
                140                 145 atttttttc ttttttgaa attctttcat tttaattttc ttaggattct atgtatttat        1609
ttaaatcaat ccttttttcca gtttgaggct tggacgacca cttgtcagat tcgtcgttta     1669
gctgtagtaa acaactgatt taaattgttt atagtactgt agttaacttt aacaacgggc      1729
cacttatatt cgagccattg cataaaaatg attcttctcg aaattcgttt acttttctta      1789 gtattttttca gttttggagt ttacgtagaa ctaataaaaa taaattttg tataaacata     1849 ccacatgcaa tgaataaatt cgaatatata accatactgt taaatattaa ttaacatttt      1909
aatcttaatt ttgcattcca g ttg cca gaa aaa tta tac aag aat ttg tcc        1960
                      Leu Pro Glu Lys Leu Tyr Lys Asn Leu Ser
                          150                 155 cac agt aca cgg atg ctc aga tac act gtc cct ctc ccc atg ctc gct        2008
His Ser Thr Arg Met Leu Arg Tyr Thr Val Pro Leu Pro Met Leu Ala
                160                 165                 170 tac cct ctc tat ctg gtaaatccta attcctaatt tcttcctga ttataattac         2063
Tyr Pro Leu Tyr Leu
        175 aattttgaat tttagattt tgagtattaa ctaaatataa attaatgttt ggggatgact       2123 acag tgg tac aga agt cct ggt aaa gaa ggg tca cat tat aac cca tac       2172
     Trp Tyr Arg Ser Pro Gly Lys Glu Gly Ser His Tyr Asn Pro Tyr
         180                 185                 190 agt agt tta ttt gct cca agc gag aga aag ctt att gca act tca act        2220
Ser Ser Leu Phe Ala Pro Ser Glu Arg Lys Leu Ile Ala Thr Ser Thr
                195                 200                 205 act tgc tgg tcg atc atg ttg gcc act ctt gtt tat cta tca ttc ctc        2268
Thr Cys Trp Ser Ile Met Leu Ala Thr Leu Val Tyr Leu Ser Phe Leu
        210                 215                 220 gtt ggt cca gtc aca gtt ctc aaa gtc tat gga gtt cct tac att            2313
Val Gly Pro Val Thr Val Leu Lys Val Tyr Gly Val Pro Tyr Ile
225                 230                 235
```

```
gtaagtttca tatattacat tattatatca ttgctaatat aatttgtttt tgacataaag    2373
ttttggaaaa atttcag atc ttt gta atg tgg ttg gac gct gtc acg tac      2423
                   Ile Phe Val Met Trp Leu Asp Ala Val Thr Tyr
                   240             245                 250 ttg cat cat cat ggt cac gat gat aag ttg cct tgg tac aga ggc aag     2471
Leu His His His Gly His Asp Asp Lys Leu Pro Trp Tyr Arg Gly Lys
                255                 260                 265 gtaagtagat caacattaat ttataagaag caataatgat tagtatttga ttaatctaaa    2531
ttattgatgt tttgtataca ataatag gaa tgg agt tat tta cgt gga gga tta   2585
                              Glu Trp Ser Tyr Leu Arg Gly Gly Leu
                                  270                 275 aca act att gat aga gat tac ggg atc ttc aac aac att cat cac gat     2633
Thr Thr Ile Asp Arg Asp Tyr Gly Ile Phe Asn Asn Ile His His Asp
                280                 285                 290 att gga act cac gtg atc cat cat ctt ttc cca caa atc cct cac tat     2681
Ile Gly Thr His Val Ile His His Leu Phe Pro Gln Ile Pro His Tyr
                295                 300                 305 cac ttg gtc gat gcc gtgagtgatc tcgctctctc tctagttcca tttgattaaa     2736
His Leu Val Asp Ala
            310 attaaagggt gattaattac taaattagtg atcttaatta atgatatgcg acag acg     2793
                                                             Thr aaa gca gct aaa cat gtg ttg gga aga tac tac aga gaa cca aag acg     2841
Lys Ala Ala Lys His Val Leu Gly Arg Tyr Tyr Arg Glu Pro Lys Thr
           315                 320                 325 tca gga gca ata ccg atc cac ttg gtg gaa agt ttg gtg gca agt att     2889
Ser Gly Ala Ile Pro Ile His Leu Val Glu Ser Leu Val Ala Ser Ile
330             335                 340                 345 aag aaa gat cat tac gtc agt gac act ggt gat att gtc ttc tac gag     2937
Lys Lys Asp His Tyr Val Ser Asp Thr Gly Asp Ile Val Phe Tyr Glu
                350                 355                 360 aca gat cca gat ctc tac gtt tat gct tct gac aaa tcc aaa atc aac     2985
Thr Asp Pro Asp Leu Tyr Val Tyr Ala Ser Asp Lys Ser Lys Ile Asn
                365                 370                 375

<210> SEQ ID NO 38
<211> LENGTH: 377
<212> TYPE: PRT
<213> ORGANISM: Brassica napus

<400> SEQUENCE: 38

Met Val Val Ala Met Asp Gln Arg Ser Asn Ala Asn Gly Asp Glu Arg
1               5                   10                  15

Phe Asp Pro Ser Ala Gln Pro Pro Phe Lys Ile Gly Asp Ile Arg Ala
                20                  25                  30

Ala Ile Pro Lys His Cys Trp Val Lys Ser Pro Leu Arg Ser Met Ser
            35                  40                  45

Tyr Val Ala Arg Asp Ile Phe Ala Val Ala Leu Ala Val Ala Ala
        50                  55                  60

Val Tyr Phe Asp Ser Trp Phe Trp Pro Leu Tyr Trp Ala Ala Gln
65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110

Leu His Ser Phe Ile Leu Val Pro Tyr His Gly Trp Arg Ile Ser His
        115                 120                 125
```

```
Arg Thr His His Gln Asn His Gly His Val Glu Asn Asp Glu Ser Trp
    130                 135                 140
Val Pro Leu Pro Glu Lys Leu Tyr Lys Asn Leu Ser His Ser Thr Arg
145                 150                 155                 160
Met Leu Arg Tyr Thr Val Pro Leu Pro Met Leu Ala Tyr Pro Leu Tyr
                165                 170                 175
Leu Trp Tyr Arg Ser Pro Gly Lys Glu Gly Ser His Tyr Asn Pro Tyr
            180                 185                 190
Ser Ser Leu Phe Ala Pro Ser Glu Arg Lys Leu Ile Ala Thr Ser Thr
        195                 200                 205
Thr Cys Trp Ser Ile Met Leu Ala Thr Leu Val Tyr Leu Ser Phe Leu
    210                 215                 220
Val Gly Pro Val Thr Val Leu Lys Val Tyr Gly Val Pro Tyr Ile Ile
225                 230                 235                 240
Phe Val Met Trp Leu Asp Ala Val Thr Tyr Leu His His His Gly His
                245                 250                 255
Asp Asp Lys Leu Pro Trp Tyr Arg Gly Lys Glu Trp Ser Tyr Leu Arg
            260                 265                 270
Gly Gly Leu Thr Thr Ile Asp Arg Asp Tyr Gly Ile Phe Asn Asn Ile
        275                 280                 285
His His Asp Ile Gly Thr His Val Ile His His Leu Phe Pro Gln Ile
    290                 295                 300
Pro His Tyr His Leu Val Asp Ala Thr Lys Ala Ala Lys His Val Leu
305                 310                 315                 320
Gly Arg Tyr Tyr Arg Glu Pro Lys Thr Ser Gly Ala Ile Pro Ile His
                325                 330                 335
Leu Val Glu Ser Leu Val Ala Ser Ile Lys Lys Asp His Tyr Val Ser
            340                 345                 350
Asp Thr Gly Asp Ile Val Phe Tyr Glu Thr Asp Pro Asp Leu Tyr Val
        355                 360                 365
Tyr Ala Ser Asp Lys Ser Lys Ile Asn
    370                 375

<210> SEQ ID NO 39
<211> LENGTH: 1131
<212> TYPE: DNA
<213> ORGANISM: Brassica napus

<400> SEQUENCE: 39
atggttgtcg ctatggacca gcgtagcaat gcgaacggag acgaaaggtt tgatccgagc    60
gcacaaccac cgttcaagat cggagatata agggcggcca ttcctaagca ttgttgggta   120
aagagtcctt tgagatccat gagctatgtc gccagagaca ttttcgccgt cgtggctctt   180
gccgtcgccg ccgtgtattt tgatagctgg ttcttttggc ctctttattg ggccgcccaa   240
ggaaccctgt tctgggctat cttcgtactc ggccacgact gtggacatgg agcttctca   300 gacattcctc ttctgaatac tgcggttggt catattcttc attccttcat tctcgttcca   360
taccatggtt ggagaataag ccatcggaca caccaccaga accatggcca tgttgaaaac   420
gacgagtctt gggttccgtt gccagaaaaa ttatacaaga atttgtccca cagtacacgg   480
atgctcagat acactgtccc tctccccatg ctcgcttacc ctctctatct gtggtacaga   540
agtcctggta agaagggtc acattataac ccatacagta gttatttgc tccaagcgag   600 agaaagctta ttgcaacttc aactacttgc tggtcgatca tgttggccac tcttgtttat   660
```

-continued

```
ctatcattcc tcgttggtcc agtcacagtt ctcaaagtct atggagttcc ttacattatc     720
tttgtaatgt ggttggacgc tgtcacgtac ttgcatcatc atggtcacga tgataagttg     780
ccttggtaca gaggcaagga atggagttat ttacgtggag gattaacaac tattgataga     840
gattacggga tcttcaacaa cattcatcac gatattggaa ctcacgtgat ccatcatctt     900
ttcccacaaa tccctcacta tcacttggtc gatgccacga aagcagctaa acatgtgttg     960
ggaagatact acagagaacc aaagacgtca ggagcaatac cgatccactt ggtggaaagt    1020
ttggtggcaa gtattaagaa agatcattac gtcagtgaca ctggtgatat tgtcttctac    1080
gagacagatc cagatctcta cgtttatgct tctgacaaat ccaaaatcaa c             1131
```

```
<210> SEQ ID NO 40
<211> LENGTH: 4512
<212> TYPE: DNA
<213> ORGANISM: Brassica napus
<220> FEATURE:
<221> NAME/KEY: CDS
<222> LOCATION: (1)..(299)
<220> FEATURE:
<221> NAME/KEY: CDS
<222> LOCATION: (923)..(1012)
<220> FEATURE:
<221> NAME/KEY: CDS
<222> LOCATION: (1683)..(1749)
<220> FEATURE:
<221> NAME/KEY: CDS
<222> LOCATION: (3451)..(3543)
<220> FEATURE:
<221> NAME/KEY: CDS
<222> LOCATION: (3650)..(3835)
<220> FEATURE:
<221> NAME/KEY: CDS
<222> LOCATION: (3921)..(4001)
<220> FEATURE:
<221> NAME/KEY: CDS
<222> LOCATION: (4096)..(4233)
<220> FEATURE:
<221> NAME/KEY: CDS
<222> LOCATION: (4318)..(4512)

<400> SEQUENCE: 40
```

```
atg gtt gtt gct atg gac cag cgc agc aat gtt aac gga gat tcc ggt       48
Met Val Val Ala Met Asp Gln Arg Ser Asn Val Asn Gly Asp Ser Gly
1               5                   10                  15 gcc cgg aag gaa gaa ggg ttt gat cca agc gaa caa cca ccg ttt aag       96
Ala Arg Lys Glu Glu Gly Phe Asp Pro Ser Glu Gln Pro Pro Phe Lys
            20                  25                  30 atc gga gat atc agg gcg gcg att cct aag cat tgt tgg gtg aag agt      144
Ile Gly Asp Ile Arg Ala Ala Ile Pro Lys His Cys Trp Val Lys Ser
        35                  40                  45 cct ttg aga tct atg agc tac gtc gcc aga gac att ttc gcc gtc gcg      192
Pro Leu Arg Ser Met Ser Tyr Val Ala Arg Asp Ile Phe Ala Val Ala
    50                  55                  60 gct ctg gcc atg gcc gcc gtg tat ttt gat agc tgg ttc ctc tgg cca      240
Ala Leu Ala Met Ala Ala Val Tyr Phe Asp Ser Trp Phe Leu Trp Pro
65                  70                  75                  80 ctc tac tgg gtt gcc caa gga acc ctt ttc tgg gcc atc ttc gtt ctt      288
Leu Tyr Trp Val Ala Gln Gly Thr Leu Phe Trp Ala Ile Phe Val Leu
                85                  90                  95 ggc cac gac tg gtaaattaaa ttttctgttt taattatttt gactcttttt           339
Gly His Asp Cys
            100 gttcaattta ttaatttctt gaatgcacgt tcgatgagta tcgtcgtcac tgacttcaag    399 atttaattct tttgaggtta cctttt catg ttcaattatt aaaaaaataa aataaaatat   459
```

```
aggatctaag attttttttct tcatcagttc aagcatcatc actcatcagt cgtaagactc        519
gtaacaaaat atcttctttt ctataattaa tattatttcc gcatttaatg gatctacgtt        579
ttgatgttct caaattttgt ttctctttct ctagatcccc ggaactttta attataatta        639
tagtatagta taatatcaag aaaatatact gtttattttt tttggcaaca aatatattac        699
tcttgtttct ttgacaagaa aaaatatatt gttttttttct tcttttttgtg ttccaatcta      759 ttttcgagat ttagacaagt gacacgtcat ataccggatt tgttaccttg ttaaagagtt        819
tgggttaaaa caaatgtaga aaagttaaaa taaattgtgc aataaatgat aaatacgttt        879
ttatgttaaa caatgatgtg aaaataaaat tgaataatgg cag t gga cat ggg agt        935
                                             Gly His Gly Ser ttt tca gac att cct ctg ctg aac agt gtg gtt ggt cac att ctt cat          983
Phe Ser Asp Ile Pro Leu Leu Asn Ser Val Val Gly His Ile Leu His
105             110                 115                 120 tca ttc atc ctc gtt cct tac cat ggt tg  gtaagtcatt tattaactat           1032
Ser Phe Ile Leu Val Pro Tyr His Gly Trp
                125                 130 ttccatgtaa actattagta cttgttttcg tatttcttac attttcgttt gtcattcttc       1092
ttgggtgcat gctagcaaac tgtaatcagt attaactggg aactaccaac tgtttttttt       1152
tgctagagta gcaattttat aattaaataa gaatcctatt aaacaatgca tgtgacaata       1212
tgaggttgct tttctgttca aaacaaatct ttagaagcca atgaaaaaga atccaaaact       1272
ttttttaaat gatatgcgcc tatctattgg tcctgactcc tgagttttct tactttctta       1332
agtataatta gattttgatt ttttttatag gttttcacta ttgttatttg tttacatcag       1392
cttcagatat cttcgaaaaa gatttacatg catcaatttc atgaggattt atagttttttc      1452 ttttacttat ttccgacaca atgtttagta gtaaaaagca ttaaatgttt ttttgctcaa       1512
aaaaaaagaa tgggattgtt agagcactct attgttagtt gttcaataaa tataccaact       1572
aaaaaaacaa aataaatata aaatgagtga gattgttaaa tcattataga gacaatttca       1632
ttttcacaaa aataaataaa tacataactt tttataattg gggtttgcag g aga ata        1689
                                                          Arg Ile agc cat cgg aca cac cac cag aac cat ggc cat gtt gaa aac gac gag         1737
Ser His Arg Thr His His Gln Asn His Gly His Val Glu Asn Asp Glu
        135                 140                 145 tct tgg gtt ccg gtaatctttc ctactctcgt agtttctctt gtcttttatt             1789
Ser Trp Val Pro
    150 tatttgtttg ttttcggaa tttattctta tgtctatgtt cttaggattc tatatgttta        1849 ttttattagt ttatgttttc agtctgaggt cagaccgacc acttgtcaga tctgttttct       1909 agctgtagta aaaacaatt tgcaagtgta atagttcagc ataattgatc ttgttagagc        1969 atttccaaaa caaactttat aattttaaat atacagtttt tgttctctca aaaagaatt        2029 taaaaatttt aaagtttgag ggacgaaact tcaaatttga actttcacta ctcaacttca       2089 aatttgaaat ttcatctttt ttatttacat tttgatcatt ataattaatt atacattaca       2149 tttatgattc ttaagtattt tctcatttat tgttttaatt cttaaatttt ttatacatca       2209 taaatatttc caatttgttt ttataaattc aaattttaca caaaaagta ataaaaattt        2269 taaataagat ttataatatt ttaaaactat aattaggcaa aaaaaatatt acaaaaaaat       2329 gtaataaaaa cttaaaaata agatatatca agacataatt attagaaatt ttaaatatta      2389 taacaatatt aataatctgg taaatttgct ccaaaacctc aaaaatttct aaattattgt       2449
```

```
ccaaacaaat tgtttaacc gaatatggag cattacaaaa ataatttat ggaatagtgt    2509 ggtattttgc ttgtagttaa tatttaatta tgtatttcta tttataattt tatatattta    2569
atgtaagatt tttttaatta atattactgt aatattttta tatatgtact agttatttat    2629
aaaagtttta tagatttgta ttagttataa caaaaataag gatcattgtg taaaatacaa    2689
ataattttga aattacgttt aaagtttggg ttatgaaaaa aatactttga aactttaaat    2749
ttagagtttt gcaaacttta aaatgttaga tagatagttt ttttggagat gcatttagtg    2809
gttatggtag taactcagaa aatgaaaaat ctatactttt atactccctc cgttttttaa    2869
tataagtcgt tttacagtta tacacgtaga ttaagaaaac cattaatttc ttatattttc    2929
tagacaaaaa catcattaat tatttaccta accacaattc aaccaatata aaaatagaag    2989
atatattacc attggtcata caacattaat tattaataaa ttttacatag aaaaccgaaa    3049
acgacatata atttggaaca aaaaaatttc tctaaaacga cttatattaa aaaacggagg    3109
gagtagtacc taactttaac gatggaccac ttatattcga gtccttagca taaaatgatt    3169
ctcctcgaaa tccgtttact ttcttcatta ttttttcctt ttcagttttg gcgttttcgt    3229 aatactttg tcttcaatct tgaaagctat tagtataaaa acttataaac acatcacatg    3289
caatgaatta atacgaatac ataaccagaa tgacaaattt tcaatgaata tttaatacca    3349
gtaagtacta ctccgtaata gtaatagtaa tagtcatatt aattttttt tgtcatcaaa    3409 caaacagtaa tagtaatatt aattataatt atgtatttca g ttg cca gaa aag ttg    3465
                                              Leu Pro Glu Lys Leu
                                                                155 tac aag aac ttg ccc cat agt act cgg atg ctc aga tac act gtt cct        3513
Tyr Lys Asn Leu Pro His Ser Thr Arg Met Leu Arg Tyr Thr Val Pro
        160                 165                 170 ctg ccc atg ctc gct tac ccg atc tat ctg gtaaaaaaaa atacaatttc        3563
Leu Pro Met Leu Ala Tyr Pro Ile Tyr Leu
    175                 180 aatttttttc ttaaaattac aaatggtttt atatttgag ttttaagcca atatataaat    3623
taattttgat tggattttaa ctacag tgg tac aga agt cct gga aaa gaa ggg    3676
                      Trp Tyr Arg Ser Pro Gly Lys Glu Gly
                                185                 190 tca cat ttt aac cca tac agt agt tta ttt gct cca agc gag agg aag        3724
Ser His Phe Asn Pro Tyr Ser Ser Leu Phe Ala Pro Ser Glu Arg Lys
            195                 200                 205 ctt att gca act tca aca act tgc tgg tcc ata atg ttg gcc act ctt        3772
Leu Ile Ala Thr Ser Thr Thr Cys Trp Ser Ile Met Leu Ala Thr Leu
    210                 215                 220 gtt tat cta tcg ttc ctc gtt ggt cca gtc aca gtt ctc aaa gtc tat        3820
Val Tyr Leu Ser Phe Leu Val Gly Pro Val Thr Val Leu Lys Val Tyr
225                 230                 235                 240 ggt gtt cct tac att gtaagtttca catattatta caagagattt atatattatt        3875
Gly Val Pro Tyr Ile
                245 aataataaat ttgttttttg acataaagtt ttggaaaatt ttcag atc ttt gta atg    3932
                                                  Ile Phe Val Met tgg ttg gac gct gtc acg tac ttg cat cat cat ggt cac gat gag aag        3980
Trp Leu Asp Ala Val Thr Tyr Leu His His His Gly His Asp Glu Lys
250                 255                 260                 265 ttg cct tgg tac aga ggc aag gtaaataaat caatttttaa aaagaaatgt        4031
Leu Pro Trp Tyr Arg Gly Lys
                270 acagaaagca ataatggtta gtattgatta atcttaattt ttgatgtttt gcatacaata    4091
```

```
atag gaa tgg agt tat tta cgt gga gga tta aca act att gat aga gat      4140
     Glu Trp Ser Tyr Leu Arg Gly Gly Leu Thr Thr Ile Asp Arg Asp
             275                 280                 285 tac gga atc ttc aac aac atc cat cac gac att gga act cac gtg atc      4188
Tyr Gly Ile Phe Asn Asn Ile His His Asp Ile Gly Thr His Val Ile
        290                 295                 300 cat cat ctt ttc cca caa atc cct cac tat cac ttg gtc gat gcg          4233
His His Leu Phe Pro Gln Ile Pro His Tyr His Leu Val Asp Ala
305                 310                 315 gtgagtgatc tagctttctc tctctctagt ttcatttgat taaatggtga ttaattacta    4293
atttaattaa tgaattgtgg acag acg aga gca gct aaa cat gtg tta gga       4344
                          Thr Arg Ala Ala Lys His Val Leu Gly
                              320                 325 aga tac tac aga gag ccg aag acg tca gga gca ata ccg att cac ttg      4392
Arg Tyr Tyr Arg Glu Pro Lys Thr Ser Gly Ala Ile Pro Ile His Leu
        330                 335                 340 gtg gag agt ttg gtc gca agt att aaa aaa gat cat tac gtc agt gac      4440
Val Glu Ser Leu Val Ala Ser Ile Lys Lys Asp His Tyr Val Ser Asp
345                 350                 355 act ggt gat att gtc ttc tac gag aca gat cca gat ctc tac gtt tat      4488
Thr Gly Asp Ile Val Phe Tyr Glu Thr Asp Pro Asp Leu Tyr Val Tyr
360                 365                 370                 375 gct tcg gac aaa tct aaa atc aat                                      4512
Ala Ser Asp Lys Ser Lys Ile Asn
                380

<210> SEQ ID NO 41
<211> LENGTH: 383
<212> TYPE: PRT
<213> ORGANISM: Brassica napus

<400> SEQUENCE: 41

Met Val Val Ala Met Asp Gln Arg Ser Asn Val Asn Gly Asp Ser Gly
1               5                   10                  15

Ala Arg Lys Glu Glu Gly Phe Asp Pro Ser Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
```

```
                195                 200                 205
Leu Ile Ala Thr Ser Thr Thr Cys Trp Ser Ile Met Leu Ala Thr Leu
            210                 215                 220

Val Tyr Leu Ser Phe Leu Val Gly Pro Val Thr Val Leu Lys Val Tyr
225                 230                 235                 240

Gly Val Pro Tyr Ile Phe Val Met Trp Leu Asp Ala Val Thr Tyr
                245                 250                 255

Leu His His Gly His Asp Glu Lys Leu Pro Trp Tyr Arg Gly Lys
            260                 265                 270

Glu Trp Ser Tyr Leu Arg Gly Leu Thr Thr Ile Asp Arg Asp Tyr
            275                 280                 285

Gly Ile Phe Asn Asn Ile His His Asp Ile Gly Thr His Val Ile His
            290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Asp Lys Ser Lys Ile Asn
370                 375                 380

<210> SEQ ID NO 42
<211> LENGTH: 1149
<212> TYPE: DNA
<213> ORGANISM: Brassica napus

<400> SEQUENCE: 42
atggttgttg ctatggacca gcgcagcaat gttaacggag attccggtgc ccggaaggaa      60
gaagggtttg atccaagcga acaaccaccg tttaagatcg agatatcag ggcggcgatt     120
cctaagcatt gttgggtgaa gagtcctttg agatctatga gctacgtcgc cagagacatt     180
ttcgccgtcg cggctctggc catggccgcc gtgtattttg atagctggtt cctctggcca     240
ctctactggg ttgcccaagg aacccttttc tgggccatct tcgttcttgg ccacgactgt     300
ggacatggga gttttttcaga cattcctctg ctgaacagtg tggttggtca cattcttcat     360
tcattcatcc tcgttcctta ccatggttgg agaataagcc atcggacaca ccaccagaac     420
catggccatg ttgaaaacga cgagtcttgg gttccgttgc cagaaaagtt gtacaagaac     480
ttgcccata gtactcggat gctcagatac actgttcctc tgcccatgct cgcttacccg     540
atctatctgt ggtacagaag tcctggaaaa gaagggtcac attttaaccc atacagtagt     600
ttatttgctc caagcgagag gaagcttatt gcaacttcaa caacttgctg gtccataatg     660
ttggccactc ttgtttatct atcgttcctc gttggtccag tcacagttct caaagtctat     720
ggtgttcctt acattatctt tgtaatgtgg ttggacgctg tcacgtactt gcatcatcat     780
ggtcacgatg agaagttgcc ttggtacaga ggcaaggaat ggagttattt acgtggagga     840
ttaacaacta ttgatagaga ttacggaatc ttcaacaaca tccatcacga cattggaact     900
cacgtgatcc atcatctttt cccacaaatc cctcactatc acttggtcga tgcgacgaga     960
gcagctaaac atgtgttagg aagatactac agagagccga agacgtcagg agcaatacccg    1020
attcacttgg tggagagttt ggtcgcaagt attaaaaaag atcattacgt cagtgacact    1080
```

```
ggtgatattg tcttctacga gacagatcca gatctctacg tttatgcttc ggacaaatct    1140
aaaatcaat                                                            1149

<210> SEQ ID NO 43
<211> LENGTH: 3729
<212> TYPE: DNA
<213> ORGANISM: Brassica napus
<220> FEATURE:
<221> NAME/KEY: CDS
<222> LOCATION: (1)..(299)
<220> FEATURE:
<221> NAME/KEY: CDS
<222> LOCATION: (782)..(871)
<220> FEATURE:
<221> NAME/KEY: CDS
<222> LOCATION: (1687)..(1753)
<220> FEATURE:
<221> NAME/KEY: CDS
<222> LOCATION: (2665)..(2757)
<220> FEATURE:
<221> NAME/KEY: CDS
<222> LOCATION: (2845)..(3030)
<220> FEATURE:
<221> NAME/KEY: CDS
<222> LOCATION: (3125)..(3205)
<220> FEATURE:
<221> NAME/KEY: CDS
<222> LOCATION: (3300)..(3437)
<220> FEATURE:
<221> NAME/KEY: CDS
<222> LOCATION: (3535)..(3729)

<400> SEQUENCE: 43 atg gtt gtt gct atg gac caa cgc acc aat gtg aac gga gat gcc ggt     48
Met Val Val Ala Met Asp Gln Arg Thr Asn Val Asn Gly Asp Ala Gly
1               5                   10                  15 gcc cgg aag gaa gaa ggg ttt gat ccg agc gca caa ccg ccg ttt aag     96
Ala Arg Lys Glu Glu Gly Phe Asp Pro Ser Ala Gln Pro Pro Phe Lys
            20                  25                  30 atc ggg gac ata agg gct gcg att cct aag cat tgt tgg gtg aaa agt    144
Ile Gly Asp Ile Arg Ala Ala Ile Pro Lys His Cys Trp Val Lys Ser
        35                  40                  45 cct ttg aga tct atg agc tac gta gcc aga gac att tgt gcc gtc gcg    192
Pro Leu Arg Ser Met Ser Tyr Val Ala Arg Asp Ile Cys Ala Val Ala
    50                  55                  60 gct ttg gcc att gcc gcc gtg tat ttt gat agc tgg ttc ctc tgt cct    240
Ala Leu Ala Ile Ala Ala Val Tyr Phe Asp Ser Trp Phe Leu Cys Pro
65                  70                  75                  80 ctc tat tgg gtc gcc caa gga acc ctt ttc tgg gcc atc ttc gtc ctc    288
Leu Tyr Trp Val Ala Gln Gly Thr Leu Phe Trp Ala Ile Phe Val Leu
                85                  90                  95 ggc cac gac tg  gtaaagtttc ttccattttg cattgcatcg atttattgaa         339
Gly His Asp Cys
            100 tgcacgttct acgagtattg tttgtcagtt acttcgtaaa atgattcttt tgatgttcat    399 tttttgaaga tctaagattt ttttttttaga ttttcttttt aaatcattgt tccaccacca   459 cctttcatcg gtcgtacgac tcgttacaac accacatctt tatttctat aattactact    519 gcttccgcat tttatggatc tctcaactta taattaaagt ataatatcaa gaatatctat   579 tatttttctt aaacaagaaa gataatattg tttctttgtt attttggtgt atttccaatc   639 tatttcgaga tttagaaatg tgacacgtca ttaccttgtt gaagtgttta aaacaaacat   699 ggaaagttta ataaatagt gcaataaatg atatatatgt atatgatgaa taatgatgtg   759 aaatataatt gaataatggc ag t gga cat ggg agt ttc tca gac att cct      809
```

```
                      Gly His Gly Ser Phe Ser Asp Ile Pro
                                      105 ctg ctg aat agt gtg gtt ggc cat att ctt cat tcc ttc atc ctc gtt        857
Leu Leu Asn Ser Val Val Gly His Ile Leu His Ser Phe Ile Leu Val
110                 115                 120                 125 cct tac cat ggt tg  gtaagtcagc ttatcaaccc ttttttactat attattaatt       911
Pro Tyr His Gly Trp
                130 attaaacttg catttgtata cttggtgcaa gttggtaaat gtaatctgat aactgaaaat       971
ctattcattg ctcgttctat tttttttggg ctagagacaa ttttataatt aaataatgca      1031
tgtgagaata tgactattta tgtgaggtag cttttcttat tcctgtcgaa aagcatcaaa      1091
tctttagcaa cgaaggaaaa aggaatcaaa ttttttatta aatgcaatgg gtctatgtct      1151
tggtcattag ttttttgcat ataatttatt tatattttt  tcttaacagc agctaattta      1211
attataatta aatattcatt ttataaataa tattagacca attattaaag gttagatatt      1271
ttaagaatta ttcatgactt tgtttattgg aactcctttt atcttttaat cttttctatt      1331
tctccatttt taataatgag aaactgactt caaatctcca ataaagatgg tcttatgtag      1391
taacagtata atttttgtt  tggtaaatgt aacatcatct tcaaatatct ttgaaaatag      1451
acttacatgc attatttgc  tgcgacatta ttgtcactta ttcctggcaa taaattagtt      1511
tattactgaa cttttttgg  tcaatttatt actagtaact ttaaacttaa aagagtgaga      1571
ttgtttgatc aaaaaaaata aaaatagagt gagatagtta gaatctgcca tgaaagcaac      1631
actatataga caatttaatt tttatgaaaa cacatttaat aatttgaggc tgcag g         1687 aga ata agc cat cgg aca cac cac cag aac cat ggc cat gtt gaa aac       1735
Arg Ile Ser His Arg Thr His His Gln Asn His Gly His Val Glu Asn
            135                 140                 145 gac gag tct tgg gtt ccg gtaacatttc cctctttaat aatttctatt              1783
Asp Glu Ser Trp Val Pro
                150 tttctgtcaa aataattagt ttttcgaaat ttgaggccag aacgaccact tgtcaaattt      1843
gattttagc  tgtagtaaaa acagtttgct agtgtcacag ttaaccggta attgattctt      1903
tttaacgatt tatagaagta acattttgt  aaaataaaat atacattatg gtatgtgaca      1963
acggaccacg cttatttgta ttggtgaatc ttttaattac tccctccaat ttattttagt      2023
tgcagattta gatttatgca catagattaa taaaaatatt ttgcacattt tcaaaataaa      2083
aacaccatta cttatacaac taaccatatt tcaaccaata aaaataaatt agaaaatatt      2143
atttataaat tttgtattga aattataaaa taatacttat tttaaaacga aattaattta      2203
caacgacaat taaactgaaa cggaaagaaa ttattaatac ttaattaaag agttttaga       2263
aaaattgaaa gacatgttta tgcgaaactc atgtgaaagt ctttgaaata atagattttg      2323
gtataaatat ttcaattttt cttaaaataa aattatata  ttaatataat ttgtgataaa      2383
atctcgtcaa aaactcacta atgcaaatgc ttttatttg  aatttcttac tcctctaaat      2443
gcatttactt ttatactaat attatttct  ttctctaatt tggcgtttcg taatagtttg      2503
tctgtattt  gaaactaac  aaaaaataat aaaaacaaaa gcttataaac acatagcatg      2563
caatgaatat gtacgaatat atataccaat acatatctaa gtactattt  tccaagtact      2623 taatcttgat tactaaaatt cattttaatt gttcctttca g tta cca gaa agg tta     2679
                                              Leu Pro Glu Arg Leu
                                                              155 tac aag aat tta ccc cac agt act cgg atg ctc aga tac act gtc cct       2727
Tyr Lys Asn Leu Pro His Ser Thr Arg Met Leu Arg Tyr Thr Val Pro
```

```
                160                 165                 170
ctg ccc atg ctc gct tac ccg atc tat ctg gtatttttta attcctaaaa        2777
Leu Pro Met Leu Ala Tyr Pro Ile Tyr Leu
    175                 180 tttactacaa gtcattttag actgtgtttt aaaacaatat aattattttt gtttggtttt    2837 actgcag tgg tac aga agt cct gga aaa gaa ggg tca cat ttt aac cca      2886
        Trp Tyr Arg Ser Pro Gly Lys Glu Gly Ser His Phe Asn Pro
            185                 190                 195 tac agt ggt tta ttt gct cca agc gag aga aag ctt att gca act tcg      2934
Tyr Ser Gly Leu Phe Ala Pro Ser Glu Arg Lys Leu Ile Ala Thr Ser
        200                 205                 210 act act tgc tgg tcc ata atg ttg gca att ctt atc tgt ctt tcc ttc      2982
Thr Thr Cys Trp Ser Ile Met Leu Ala Ile Leu Ile Cys Leu Ser Phe
        215                 220                 225 ctc gtt ggt cca gtc aca gtt ctc aaa gta tac ggt gtt cct tac att      3030
Leu Val Gly Pro Val Thr Val Leu Lys Val Tyr Gly Val Pro Tyr Ile
230                 235                 240                 245 gtaagtttct tagtatatca taaagggtat atatttatta ttcaatatat atactatatg   3090
atttgttttt gtcatatatt tttgaaatat tcag atc ttt gtg atg tgg ttg gac   3145
                                    Ile Phe Val Met Trp Leu Asp
                                                            250 gct gtc act tac ttg cat cac cat ggt cat gat gag aag ttg cct tgg     3193
Ala Val Thr Tyr Leu His His His Gly His Asp Glu Lys Leu Pro Trp
            255                 260                 265 tac aga ggc aag gtaattaaat taactattac aagtatttta caaaaaacta         3245
Tyr Arg Gly Lys
    270 atgattagta tatttgatta atcttaattc ttgatgtttt gtgattaata atag gaa     3302
                                                             Glu tgg agt tac tta cgt gga gga tta aca act att gat aga gat tac gga    3350
Trp Ser Tyr Leu Arg Gly Gly Leu Thr Thr Ile Asp Arg Asp Tyr Gly
    275                 280                 285 att ttc aac aac att cat cac gac att gga act cac gtg atc cat cat    3398
Ile Phe Asn Asn Ile His His Asp Ile Gly Thr His Val Ile His His
290                 295                 300                 305 ctt ttc cca caa atc cct cac tat cac ttg gtc gat gct gtgagtcatc     3447
Leu Phe Pro Gln Ile Pro His Tyr His Leu Val Asp Ala
            310                 315 tcactctctg gctactttca tcaaaaccat ttgattaaag ggtgattaat tactaatgta   3507
gtgattttaa caaatggaat gtgacag aca aaa gca gct aaa cat gtg ttg gga   3561
                        Thr Lys Ala Ala Lys His Val Leu Gly
                            320                 325 aga tac tac aga gaa cca aag acg tca gga gca ata ccg atc cac ttg    3609
Arg Tyr Tyr Arg Glu Pro Lys Thr Ser Gly Ala Ile Pro Ile His Leu
        330                 335                 340 gtg gag agt ttg gta gca agt att aag aaa gat cat tac gtc agt gac    3657
Val Glu Ser Leu Val Ala Ser Ile Lys Lys Asp His Tyr Val Ser Asp
345                 350                 355 act ggt gac att gtc ttc tac gag act gat cca gat ctc tac gtt tat    3705
Thr Gly Asp Ile Val Phe Tyr Glu Thr Asp Pro Asp Leu Tyr Val Tyr
360                 365                 370                 375 gct tct gtc aaa tcg aaa atc aat                                     3729
Ala Ser Val Lys Ser Lys Ile Asn
            380

<210> SEQ ID NO 44
<211> LENGTH: 383
<212> TYPE: PRT
```

<213> ORGANISM: Brassica napus

<400> SEQUENCE: 44

```
Met Val Val Ala Met Asp Gln Arg Thr Asn Val Asn Gly Asp Ala Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Cys Ala Val Ala
    50                  55                  60

Ala Leu Ala Ile Ala Ala Val Tyr Phe Asp Ser Trp Phe Leu Cys Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
130                 135                 140

Glu Asn Asp Glu Ser Trp Val Pro Leu Pro Glu Arg Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Gly Leu Phe Ala Pro Ser Glu Arg Lys
        195                 200                 205

Leu Ile Ala Thr Ser Thr Thr Cys Trp Ser Ile Met Leu Ala Ile Leu
    210                 215                 220

Ile Cys Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Lys
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
        355                 360                 365

Asp Pro Asp Leu Tyr Val Tyr Ala Ser Val Lys Ser Lys Ile Asn
    370                 375                 380
```

<210> SEQ ID NO 45
<211> LENGTH: 1149

```
<212> TYPE: DNA
<213> ORGANISM: Brassica napus

<400> SEQUENCE: 45
atggttgttg ctatggacca acgcaccaat gtgaacggag atgccggtgc ccggaaggaa      60
gaagggtttg atccgagcgc acaaccgccg tttaagatcg gggacataag ggctgcgatt     120
cctaagcatt gttgggtgaa aagtcctttg agatctatga gctacgtagc cagagacatt     180
tgtgccgtcg cggctttggc cattgccgcc gtgtattttg atagctggtt cctctgtcct     240
ctctattggg tcgcccaagg aaccctttc tgggccatct tcgtcctcgg ccacgactgt     300
ggacatggga gtttctcaga cattcctctg ctgaatagtg tggttggcca tattcttcat     360
tccttcatcc tcgttcctta ccatggttgg agaataagcc atcggacaca ccaccagaac     420
catggccatg ttgaaaacga cgagtcttgg gttccgttac cagaaaggtt atacaagaat     480
ttaccccaca gtactcggat gctcagatac actgtccctc tgcccatgct cgcttacccg     540
atctatctgt ggtacagaag tcctggaaaa gaagggtcac attttaaccc atacagtggt     600
ttatttgctc caagcgagag aaagcttatt gcaacttcga ctacttgctg gtccataatg     660
ttggcaattc ttatctgtct ttccttcctc gttggtccag tcacagttct caaagtatac     720
ggtgttcctt acattatctt tgtgatgtgg ttggacgctg tcacttactt gcatcaccat     780
ggtcatgatg agaagttgcc ttggtacaga ggcaaggaat ggagttactt acgtggagga     840
ttaacaacta ttgatagaga ttacggaatt ttcaacaaca ttcatcacga cattggaact     900
cacgtgatcc atcatcttt cccacaaatc cctcactatc acttggtcga tgctacaaaa     960
gcagctaaac atgtgttggg aagatactac agagaaccaa agacgtcagg agcaataccg    1020
atccacttgg tggagagttt ggtagcaagt attaagaaag atcattacgt cagtgacact    1080
ggtgacattg tcttctacga gactgatcca gatctctacg tttatgcttc tgtcaaatcg    1140
aaaatcaat                                                             1149

<210> SEQ ID NO 46
<211> LENGTH: 3555
<212> TYPE: DNA
<213> ORGANISM: Brassica napus
<220> FEATURE:
<221> NAME/KEY: CDS
<222> LOCATION: (1)..(290)
<220> FEATURE:
<221> NAME/KEY: CDS
<222> LOCATION: (882)..(971)
<220> FEATURE:
<221> NAME/KEY: CDS
<222> LOCATION: (2032)..(2098)
<220> FEATURE:
<221> NAME/KEY: CDS
<222> LOCATION: (2499)..(2591)
<220> FEATURE:
<221> NAME/KEY: CDS
<222> LOCATION: (2700)..(2885)
<220> FEATURE:
<221> NAME/KEY: CDS
<222> LOCATION: (2964)..(3044)
<220> FEATURE:
<221> NAME/KEY: CDS
<222> LOCATION: (3130)..(3267)
<220> FEATURE:
<221> NAME/KEY: CDS
<222> LOCATION: (3361)..(3555)

<400> SEQUENCE: 46 atg gtt gtc gct atg gac cag cgt agc aat gtg aac gga gat tcc aag       48
Met Val Val Ala Met Asp Gln Arg Ser Asn Val Asn Gly Asp Ser Lys
```

| | | | | |
|---|---|---|---|---|
| 1 | 5 | | 10 | 15 |

```
gac gaa agg ttt gat ccg agc gca caa cca ccg ttt aag atc gga gat      96
Asp Glu Arg Phe Asp Pro Ser Ala Gln Pro Pro Phe Lys Ile Gly Asp
            20                  25                  30 ata agg gct gcg att cct aag cat tgt tgg gtc aag agt cct ttg aga     144
Ile Arg Ala Ala Ile Pro Lys His Cys Trp Val Lys Ser Pro Leu Arg
            35                  40                  45 tcc atg agc tac gtc gcg aga gac att ttc tcc gtc gtg gct ctg gcc    192
Ser Met Ser Tyr Val Ala Arg Asp Ile Phe Ser Val Val Ala Leu Ala
 50                  55                  60 gtc gcc gcc gtg tat ttt gat agc tgg ttc ttc tgg cct ctt tat tgg    240
Val Ala Ala Val Tyr Phe Asp Ser Trp Phe Phe Trp Pro Leu Tyr Trp
65                  70                  75                  80 gcc gcc caa gga acc ctt ttc tgg gcc atc ttc gta ctc ggc cac gac    288
Ala Ala Gln Gly Thr Leu Phe Trp Ala Ile Phe Val Leu Gly His Asp
                    85                  90                  95 tg  gtaatttaat tttcaattta ttttttcttc aacttcttaa ttttgatatg         340
Cys tttatatgtt ttttcgtttt tttgcatcgt ctttgatttc ttgaacgcac gttcgatatg   400
agattttcac tgacttcaag atttgattct cttcaggttt acttttaaaa aaaaaaatta   460
ttatgttcac ccaaattggc ctattttaaa agcaaagggg atctaagat ttttaattct    520 tctctttttc agtcgtaaca ctgctaactt ttttttttga tcaaatcgta acactcataa   580
gtcctaacta aacatctttt tctttcctat aattattgtt ggttccgcat tttatggatc   640
tacgtttgaa agtttcaata aaacacattt tattgtttga agtaacaat ataattactg    700 tatattgatt cttttaatta ttgtgtgttg ttccaatcta ctttcgaaat atagtcatgt   760
gacacgtcat attctatttt tgttaccttg ttggaacgtt tgaattgagt aaagtttaat   820
taacattgtg caataaatga taaacatgtt tatgatgtaa aattcaatttt gaataataca  880 g t  gga cat ggg agc ttc tca gac att cct ctt ctg aat act gcg gtt   927
     Gly His Gly Ser Phe Ser Asp Ile Pro Leu Leu Asn Thr Ala Val
                 100                 105                 110 ggt cat att ctt cat tcc ttc att ctc gtt cca tac cat ggt tg         971
Gly His Ile Leu His Ser Phe Ile Leu Val Pro Tyr His Gly Trp
            115                 120                 125 gtaagtcatt tatttaaaca tctttttcat gcaaatttat tcttgttttc gtatttctta 1031 cattttcctt gtcattcttg gtgcatgtta gcaaactgta atctgataac tgaaaatata 1091 ttaattttcc atagtaaaat aatgcatgtg actaaaagca tcaaaatctt tagcatcgaa 1151 gaaaaaagaa ccaaactttt atttaatgct atgggcctat ttatggtcca attagctatt 1211 atcatatgac atgtccttga ataaattaat gtagcttcat atgtgagttt aataatattt 1271 atatatttt gttttaatgg cttatttat tgttaaatgg atacatcagc ttgaaatgtc   1331
tacgaacatg catcattttc ctagatacac ttgtttgttg ctcaaaaatg ataacttag   1391 ttaaacgagt gagcatgttc tatggggttt cttagagcat gattattgag aagttcctag 1451 agtgaggttt ttaccggaat ataagaatct atctcttaac ttttaactaa aaaaattaag 1511 aaccggcttt taaaactcgt atttaagaac cgttttttag ttttttagtt aaaaatcaag 1571 agacgagttc ttatattccg ctaagaactc caccctgaga acttctcaat aatcatgctc 1631 ttagtgctct aagaagggtc cttaacaaaa tattaataat aagatatagt gtgggcccaa 1691 aaaaaaacaa aaaccggtt acaaaagtcg cgaaagaagg atcgattttg gtcttttact  1751
tgtactgttt gtggatccca ctggtggtgg tccgcgattg gtttctttt taatttaatt  1811
```

-continued

| | |
|---|---|
| tatttttta atcggagaaa aaaattaaga aaccaaaaac agttttaatc atggcctcat | 1871 |
| gttggggttg agttttatat tctgataaga atcccatctt aaaaacccg ttaaacatgc | 1931 |
| tcttaccatc tgcttcgaaa atgatatgtt attgacaatt ccaatttcat ttttatgaaa | 1991 | ataaaataat agtttatttt ataactgagg gtggttgcag g aga ata agc cat cgg  2047
                                                    Arg Ile Ser His Arg
                                                           130 aca cac cac cag aac cat ggc cat gtt gaa aac gac gag tct tgg gtt  2095
Thr His His Gln Asn His Gly His Val Glu Asn Asp Glu Ser Trp Val
    135                   140                   145 ccg gtaatctttc cctctctcat attttttttc ttttttttga aattctttca  2148
Pro

| | |
|---|---|
| ttttaatttt cttaggattc tatgtattta ttttaatcaa tccttttcc agtttgaggc | 2208 |
| taggacgacc acttgtcaga tttgtcgttt agctgtagta aacaactgat ttaaattgtt | 2268 |
| tatagtactg tagttaactt taacaacgga ccacttatat tcgagccatt ggcataaaat | 2328 |
| gattcttctc gaaattcgtt tacttttctt agtattttc aatttggag tttacgtaga | 2388 |
| actaataaaa agaaaaactt ataaacacac cacatgcaat gaataaattc gaatatataa | 2448 | ccatactgtt aaatattaat ttacatttta atcttaattt tgcattccag ttg cca  2504
                                                             Leu Pro
                                                             150 gaa aaa tta tac aag aat ttg tcc cac agt aca cgg atg ctc aga tac  2552
Glu Lys Leu Tyr Lys Asn Leu Ser His Ser Thr Arg Met Leu Arg Tyr
    155                   160                   165 act gtc cct ctc ccc atg ctc gct tac cct ctc tat ctg gtaaatccta  2601
Thr Val Pro Leu Pro Met Leu Ala Tyr Pro Leu Tyr Leu
       170               175               180 attcctaatt tttcttcctg attataatta caatttgaa ttttagatt ttgagtatta  2661 actaaatata aattaaattt gtttggggat gactacag tgg tac aga agt cct ggt  2717
                                           Trp Tyr Arg Ser Pro Gly
                                                              185 aaa gaa ggg tca cat tat aac cca tac agt agt tta ttt gcc cca agc  2765
Lys Glu Gly Ser His Tyr Asn Pro Tyr Ser Ser Leu Phe Ala Pro Ser
       190                 195                   200 gag aga aag ctt att gca act tca act act tgc tgg tcg atc gtg ttg  2813
Glu Arg Lys Leu Ile Ala Thr Ser Thr Thr Cys Trp Ser Ile Val Leu
        205               210                 215 gcc act ctt gtt tat cta tca ttc ctc gtt ggt cca gtc aca gtt cta  2861
Ala Thr Leu Val Tyr Leu Ser Phe Leu Val Gly Pro Val Thr Val Leu
       220                 225                 230 aaa gtc tat ggt gtt cct tac att gtaagtttca tatttctt tattatatca  2915
Lys Val Tyr Gly Val Pro Tyr Ile
235                240 ttgctaatat aatttgttt tgacataaaa gttttggaaa aatttcag atc ttt gta  2972
                                                              Ile Phe Val
                                                              245 atg tgg ttg gac gct gtc acg tac ttg cat cat cat ggt cac gat gat  3020
Met Trp Leu Asp Ala Val Thr Tyr Leu His His His Gly His Asp Asp
                 250                   255                 260 aag ctg cct tgg tac aga ggc aag gtaagtagat caacattatt tataagaagc  3074
Lys Leu Pro Trp Tyr Arg Gly Lys
       265 aataatgatt agtagttgaa taatctgaat ttttgatgtt tttgtacaat aatag gaa  3132
                                                                              Glu
                                                                              270 tgg agt tat tta cgt gga gga tta aca act gtt gat aga gat tac ggg  3180
Trp Ser Tyr Leu Arg Gly Gly Leu Thr Thr Val Asp Arg Asp Tyr Gly

```
                    275                 280                 285
atc ttc aac aac att cat cac gat att gga act cac gtg atc cat cat      3228
Ile Phe Asn Asn Ile His His Asp Ile Gly Thr His Val Ile His His
            290                 295                 300 ctt ttc cca caa atc cct cac tat cac ttg gtc gat gcc gtgagtgatc       3277
Leu Phe Pro Gln Ile Pro His Tyr His Leu Val Asp Ala
            305                 310                 315 tcgctctctc tctagtttca tttgattata ttaaagggtg attaattact aaattagtga    3337
tcttaattaa tgacatgcga cag acg aaa gca gct aaa cat gtg ttg gga aga    3390
                      Thr Lys Ala Ala Lys His Val Leu Gly Arg
                              320                 325 tac tac aga gaa cca aag acg tca gga gca ata ccg atc cac tta gtg      3438
Tyr Tyr Arg Glu Pro Lys Thr Ser Gly Ala Ile Pro Ile His Leu Val
                    330                 335                 340 gaa agt ttg gtg gca agt att aag aaa gat cat tac gtc agt gac act      3486
Glu Ser Leu Val Ala Ser Ile Lys Lys Asp His Tyr Val Ser Asp Thr
                345                 350                 355 ggt gat att gtc ttc tac gag aca gat cca gat ctc tac gtt tat gct      3534
Gly Asp Ile Val Phe Tyr Glu Thr Asp Pro Asp Leu Tyr Val Tyr Ala
            360                 365                 370 tct gac aaa tcc aaa atc aat                                          3555
Ser Asp Lys Ser Lys Ile Asn
        375                 380

<210> SEQ ID NO 47
<211> LENGTH: 380
<212> TYPE: PRT
<213> ORGANISM: Brassica napus

<400> SEQUENCE: 47

Met Val Val Ala Met Asp Gln Arg Ser Asn Val Asn Gly Asp Ser Lys
1               5                   10                  15

Asp Glu Arg Phe Asp Pro Ser Ala Gln Pro Pro Phe Lys Ile Gly Asp
            20                  25                  30

Ile Arg Ala Ala Ile Pro Lys His Cys Trp Val Lys Ser Pro Leu Arg
        35                  40                  45

Ser Met Ser Tyr Val Ala Arg Asp Ile Phe Ser Val Ala Leu Ala
    50                  55                  60

Val Ala Ala Val Tyr Phe Asp Ser Trp Phe Phe Trp Pro Leu Tyr Trp
65                  70                  75                  80

Ala Ala Gln Gly Thr Leu Phe Trp Ala Ile Phe Val Leu Gly His Asp
                85                  90                  95

Cys Gly His Gly Ser Phe Ser Asp Ile Pro Leu Leu Asn Thr Ala Val
            100                 105                 110

Gly His Ile Leu His Ser Phe Ile Leu Val Pro Tyr His Gly Trp Arg
        115                 120                 125

Ile Ser His Arg Thr His His Gln Asn His Gly His Val Glu Asn Asp
    130                 135                 140

Glu Ser Trp Val Pro Leu Pro Glu Lys Leu Tyr Lys Asn Leu Ser His
145                 150                 155                 160

Ser Thr Arg Met Leu Arg Tyr Thr Val Pro Leu Pro Met Leu Ala Tyr
                165                 170                 175

Pro Leu Tyr Leu Trp Tyr Arg Ser Pro Gly Lys Glu Gly Ser His Tyr
            180                 185                 190

Asn Pro Tyr Ser Ser Leu Phe Ala Pro Ser Glu Arg Lys Leu Ile Ala
        195                 200                 205
```

Thr Ser Thr Thr Cys Trp Ser Ile Val Leu Ala Thr Leu Val Tyr Leu
    210             215                 220

Ser Phe Leu Val Gly Pro Val Thr Val Leu Lys Val Tyr Gly Val Pro
225             230                 235                 240

Tyr Ile Ile Phe Val Met Trp Leu Asp Ala Val Thr Tyr Leu His His
                245                 250                 255

His Gly His Asp Asp Lys Leu Pro Trp Tyr Arg Gly Lys Glu Trp Ser
            260                 265                 270

Tyr Leu Arg Gly Gly Leu Thr Thr Val Asp Arg Asp Tyr Gly Ile Phe
            275                 280                 285

Asn Asn Ile His His Asp Ile Gly Thr His Val Ile His His Leu Phe
290                 295                 300

Pro Gln Ile Pro His Tyr His Leu Val Asp Ala Thr Lys Ala Ala Lys
305             310                 315                 320

His Val Leu Gly Arg Tyr Tyr Arg Glu Pro Lys Thr Ser Gly Ala Ile
                325                 330                 335

Pro Ile His Leu Val Glu Ser Leu Val Ala Ser Ile Lys Lys Asp His
            340                 345                 350

Tyr Val Ser Asp Thr Gly Asp Ile Val Phe Tyr Glu Thr Asp Pro Asp
            355                 360                 365

Leu Tyr Val Tyr Ala Ser Asp Lys Ser Lys Ile Asn
370                 375                 380

<210> SEQ ID NO 48
<211> LENGTH: 1140
<212> TYPE: DNA
<213> ORGANISM: Brassica napus

<400> SEQUENCE: 48
atggttgtcg ctatggacca gcgtagcaat gtgaacggag attccaagga cgaaaggttt    60
gatccgagcg cacaaccacc gtttaagatc ggagatataa gggctgcgat tcctaagcat   120
tgttgggtca agagtccttt gagatccatg agctacgtcg cgagagacat tttctccgtc   180
gtggctctgg ccgtcgccgc cgtgtatttt gatagctggt tcttctggcc tctttattgg   240
gccgcccaag gaacccttt ctgggccatc ttcgtactcg ccacgactg tggacatggg    300 agcttctcag acattcctct tctgaatact gcggttggtc atattcttca ttccttcatt   360
ctcgttccat accatggttg gagaataagc catcggacac accaccagaa ccatggccat   420
gttgaaaacg acgagtcttg ggttccgttg ccagaaaaat tatacaagaa tttgtcccac   480
agtacacgga tgctcagata cactgtccct ctccccatgc tcgcttaccc tctctatctg   540
tggtacagaa gtcctggtaa agaagggtca cattataacc catacagtag tttatttgcc   600
ccaagcgaga gaaagcttat tgcaacttca actacttgct ggtcgatcgt gttggccact   660
cttgtttatc tatcattcct cgttggtcca gtcacagttc taaaagtcta tggtgttcct   720
tacattatct ttgtaatgtg gttggacgct gtcacgtact gcatcatca tggtcacgat   780 gataagctgc cttggtacag aggcaaggaa tggagttatt acgtggagg attaacaact    840 gttgatagag attacgggat cttcaacaac attcatcacg atattggaac tcacgtgatc   900
catcatcttt tcccacaaat ccctcactat cacttggtcg atgccacgaa agcagctaaa   960
catgtgttgg gaagatacta cagagaacca aagacgtcag gagcaatacc gatccactta  1020
gtggaaagtt tggtggcaag tattaagaaa gatcattacg tcagtgacac tggtgatatt  1080
gtcttctacg agacagatcc agatctctac gtttatgctt ctgacaaatc caaaatcaat  1140

<210> SEQ ID NO 49
<211> LENGTH: 4770
<212> TYPE: DNA
<213> ORGANISM: Brassica napus
<220> FEATURE:
<221> NAME/KEY: CDS
<222> LOCATION: (1)..(299)
<220> FEATURE:
<221> NAME/KEY: CDS
<222> LOCATION: (913)..(1002)
<220> FEATURE:
<221> NAME/KEY: CDS
<222> LOCATION: (1665)..(1731)
<220> FEATURE:
<221> NAME/KEY: CDS
<222> LOCATION: (3709)..(3801)
<220> FEATURE:
<221> NAME/KEY: CDS
<222> LOCATION: (3908)..(4093)
<220> FEATURE:
<221> NAME/KEY: CDS
<222> LOCATION: (4179)..(4259)
<220> FEATURE:
<221> NAME/KEY: CDS
<222> LOCATION: (4354)..(4491)
<220> FEATURE:
<221> NAME/KEY: CDS
<222> LOCATION: (4576)..(4770)

<400> SEQUENCE: 49

| | | | | | | | | | | | | | | | | |
|---|---|---|---|---|---|---|---|---|---|---|---|---|---|---|---|---|
| atg | gtt | gtt | gct | atg | tac | cag | cgc | agc | aat | gtt | aac | gga | gat | tcc | ggt | 48 |
| Met | Val | Val | Ala | Met | Tyr | Gln | Arg | Ser | Asn | Val | Asn | Gly | Asp | Ser | Gly | |
| 1 | | | | 5 | | | | | 10 | | | | | 15 | | |
| gcc | cgg | aag | gaa | gaa | ggg | ttt | gat | cca | agc | gca | caa | cca | ccg | ttt | aag | 96 |
| Ala | Arg | Lys | Glu | Glu | Gly | Phe | Asp | Pro | Ser | Ala | Gln | Pro | Pro | Phe | Lys | |
| | | 20 | | | | | 25 | | | | | 30 | | | | |
| atc | gga | gat | ata | agg | gcg | gcg | att | cct | aag | cat | tgc | tgg | gtg | aag | agt | 144 |
| Ile | Gly | Asp | Ile | Arg | Ala | Ala | Ile | Pro | Lys | His | Cys | Trp | Val | Lys | Ser | |
| | 35 | | | | | 40 | | | | | 45 | | | | | |
| cct | ttg | aga | tct | atg | agc | tac | gtc | gcc | aga | gac | att | ttc | gcc | gtc | gcg | 192 |
| Pro | Leu | Arg | Ser | Met | Ser | Tyr | Val | Ala | Arg | Asp | Ile | Phe | Ala | Val | Ala | |
| 50 | | | | | 55 | | | | | 60 | | | | | | |
| gct | ctg | gcc | atg | gcc | gcc | gtg | tat | ttt | gat | agc | tgg | ttc | ctc | tgg | cca | 240 |
| Ala | Leu | Ala | Met | Ala | Ala | Val | Tyr | Phe | Asp | Ser | Trp | Phe | Leu | Trp | Pro | |
| 65 | | | | 70 | | | | | 75 | | | | | 80 | | |
| ctc | tac | tgg | gtt | gcc | caa | gga | acc | ctt | ttc | tgg | gcc | atc | ttc | gtt | ctt | 288 |
| Leu | Tyr | Trp | Val | Ala | Gln | Gly | Thr | Leu | Phe | Trp | Ala | Ile | Phe | Val | Leu | |
| | | | 85 | | | | | 90 | | | | | 95 | | | |
| ggc | cac | gac | tg | gtaaattaaa | | ttttcagttt | | taattatttt | | gtctcttttt | | | | | | 339 |
| Gly | His | Asp | Cys | | | | | | | | | | | | | |
| | | | 100 | | | | | | | | | | | | | | gttcaattta ttaatttctt gaatgcacgt tcgatgagta tcgtcactga cttcaagatt      399 taattctttt gaggttactt tttcatgttt aattattaaa aaaataaaag aaaatatagg      459 atctaagatt ttttttcttc atcaatgttc aagcatcatc actcatcagt cgtaagactc      519 gtaacaaaat atcttctttt ctataattaa tattatttcc gcattttatg gatctacgtt      579 ttgatgttct caattttgt ttctctttct ctagatcccc ggaacttttta attataatta      639 tagtatagta taatatcaag aaaatatact gtttatttt ttggcaacaa atatattgtt       699 ttttgacaag aaaaatatat atatttttc ttctttttgt gttccaatct attttgtgat       759 ttagacaagt gacacgtcat ataccggatt tgttaccttg ttaaagagct tgagttaaaa      819 caaatgtaga aaagttaaaa taattgtgc aataaatgat aaatacgttt ttatgttaaa      879 taatgatgtg aaaataaaat tgaataatgg cag t gga cat ggg agt ttc tca         931

```
                Gly His Gly Ser Phe Ser
                                105 gac att cct ctg ctg aac agt gtg gtt ggt cac att ctt cat tca ttc      979
Asp Ile Pro Leu Leu Asn Ser Val Val Gly His Ile Leu His Ser Phe
        110                 115                 120 atc ctc gtt cct tac cat ggt tg gtaagtcatt tattaactat ttccatgtaa     1032
Ile Leu Val Pro Tyr His Gly Trp
        125             130 attattagta cttgttttcg tatttcttac attttcgttt gttattcttg ggtgcaatgc   1092
taggaaactg taatcagtat taactggaaa ctaccgactg ttttttttgtt gctagagtag  1152 caattttata attaaataag aatcctatta aacaatgcat gtgactatat gaggttgctt   1212
tttctgttca aaagcatcaa atctttagca gccaatgaaa agaatccaa acctttttctt  1272 aaatgatatg cgcctatcta tggtcctgag ttttcttagt ttcttaagta tatttagatt  1332 ttgattttttt tttaggttttt cacttattgt tatttgttta catcagcttc aaatatcttc 1392 gaaaaagact tacatgcatc aatttcctga ggatttatag ttttttttttac ttatttctga 1452 cacaatgttt attagtaaaa agcatcaaat gttttttttgc tcaaaaaaaa gaatgggatt  1512
gttagagcac tctattgtta gttgttcaat aaatatatca actaaaaaaa caaaataaat   1572
ataaaatgag tgagattgtt aaatcattat agagacaatt tcattttcac aaaaataaat  1632
aaatacataa cttttgtaat tggggtttgc ag g aga ata agc cat cgg aca cac  1686
                                   Arg Ile Ser His Arg Thr His
                                                     135 cac cag aac cat ggc cat gtt gaa aac gac gag tct tgg gtt ccg         1731
His Gln Asn His Gly His Val Glu Asn Asp Glu Ser Trp Val Pro
        140                 145                 150 gtaatctttc ctactctcat agtttctctt gtctttttatt gatttgttct ttttggggaa  1791
ttcattctta tgtctaagtt cttatgatta ttggggttct aaggtagaaa ttctatctta  1851
gaatataaaa acatgtctct taattttttaa ctaaaaagtt aagaaccagc ttttaaataa  1911
gaattttaaa aactggtttt ttaaatttttt tagttaaaag ttaaaaaacg aattattata  1971
tttctctaaa aacctcgtca taagaacccct cattgatcat gctatgttta ttttattagt  2031
ttatgttttc agtctgaggt cagaccggcc acttgtcaga tctgttttct agctgtagta  2091
aaaaacaatt tgccagtgta atagttcagc ggtaattaat gttctggaat ctatctcaaa  2151 ttttttttttt ataacttcag atataaagtt ttttgttctt aaaaaataaa tttcaaaatt  2211
tcaaatttga agttttttttt atttgcattt tgatcgttat aattaattac acgttacatt  2271
tataattctg aagtattttt tcatttatcg ttttaattct taaattttttt atatattata  2331 aatatttcca gtttgttttt ataaattcaa attttacaca taaagtaat aaaaaaactt   2391 taaaataaga tacatgaaga cataactatt agaaaatttt aaatattata actatactaa  2451
taatctggta aatttgctct ggaacctcca aaattattgt ctaaacaaat tttatataac  2511
cgaagatgga acattacgaa aataatttta tgaataata tgttatttttg cttctaatttt  2571 aatatttaat tatatatttc tatttataat tttatatatt taatgtaatt ttttattaat  2631
taatattact gtaatatttt tatatatgtg ctagttattt ataattttttt ttatggattt  2691 atatttgtta taacaaataa agatcattgt gtaaaataca aataatttttg aaattacgtt  2751 tgaagtttgt ttttgaagaa aaccactttg aaactttaaa tttagagttt cgtgaactct  2811
aaaatagaga gttttttttta gaggttacgc agtaactcag aaaatgaaaa atctatactt  2871
ttatagtacc gaactttaac gatggaccac ttagagcatc attaacgggg gttcttagga  2931
```

-continued

```
cggggttctt agcggaatat aagaacctga ctcttaattt ttaactgaaa atgctaagag    2991
tcggctctta actttaatga tgctaagagt cggctcttaa ctttaaggac ggggttctta    3051
agagccgact cttaactttt tcagttaaaa taacttttc agttaaaagt taagagtcgg    3111
gttcttatat tctgttaaga accatgtact aagaaccctg tgttaatgat ggtgttatat    3171
tcgagtcctt agcgtaaaat gattctcctc gaaatccgtt tactttcttc gttattttt    3231 ccttttcagt tttggcgttt tcgtaatact tttctctgca atcttgaaag ctattagtat    3291
aaaacttata aacacatgaa ttaatacgaa tacataacca gaatgacaaa ttttcaatga    3351
atatttaata ctagtaagta ctactccgta atactccctc tgttttttaa agatgaatgt    3411
tctagagaaa tattttgttt ccaaatgatg tatttttcat gttttcaaag tatattttgt    3471
caactaataa tgaaaaattg tgtatttcaa aaatattaat tacatttctt ttaatccaat    3531
tggtttaaaa atataaaaaa tataaagtta caaaaaacta tgcattaata actaaatttt    3591
aatatgattt cttaataaat gtgaaaatcc tagaacattc atcttaaaaa aacagagga    3651 gtagtaatta gtaatagtaa tagtaatagt catattaatt ataattatgt atttcag      3708 ttg cca gaa aag ttg tac aag aac ttg ccc cat agt act cgg atg ctc      3756
Leu Pro Glu Lys Leu Tyr Lys Asn Leu Pro His Ser Thr Arg Met Leu
    155                 160                 165 aga tac act gtc cct ctg ccc atg ctc gct tac ccg atc tat ctg          3801
Arg Tyr Thr Val Pro Leu Pro Met Leu Ala Tyr Pro Ile Tyr Leu
    170                 175                 180 gtaaaaaaaa aatacaattt ctattttttc ttaaaattac aaatgatttt atattttgag    3861
ttttaagcca atatataaat taattttgat tggaccttaa ctacag tgg tac aga       3916
                                                    Trp Tyr Arg
                                                             185 agt cct gga aaa gaa ggg tca cat ttt aac cca tac agt agt tta ttt      3964
Ser Pro Gly Lys Glu Gly Ser His Phe Asn Pro Tyr Ser Ser Leu Phe
        190                 195                 200 gct cca agc gag agg aag ctt att gca act tca act act tgc tgg tcc      4012
Ala Pro Ser Glu Arg Lys Leu Ile Ala Thr Ser Thr Thr Cys Trp Ser
        205                 210                 215 ata atg ttg gcc act ctt gtt tat cta tcg ttc ctc gtt gat cca gtc      4060
Ile Met Leu Ala Thr Leu Val Tyr Leu Ser Phe Leu Val Asp Pro Val
        220                 225                 230 aca gtt ctc aaa gtc tat ggc gtt cct tac att gtaagtttca catattatta   4113
Thr Val Leu Lys Val Tyr Gly Val Pro Tyr Ile
235                 240                 245 caagaaattt atatattatt aataataaat ttgttttttg acataaagtt ttggaaaatt    4173 ttcag atc ttt gtg atg tgg ttg gac gct gtc acg tac ttg cat cat cat   4223
      Ile Phe Val Met Trp Leu Asp Ala Val Thr Tyr Leu His His His
                  250                 255                 260 ggt cac gat gag aag ttg cct tgg tac aga ggc aag gtaattaaat           4269
Gly His Asp Glu Lys Leu Pro Trp Tyr Arg Gly Lys
            265                 270 caatttttaa aagaaatgt acagaaagca ataatggtta gtattgatta atcttaattt     4329
ttgatgtttt gcatacaata atag gaa tgg agt tat tta cgt gga gga tta       4380
                              Glu Trp Ser Tyr Leu Arg Gly Gly Leu
                                  275                 280 aca act att gat aga gat tac gga atc ttc aac aac atc cat cac gac      4428
Thr Thr Ile Asp Arg Asp Tyr Gly Ile Phe Asn Asn Ile His His Asp
            285                 290                 295 att gga act cac gtg atc cat cat ctt ttc cca caa atc cct cac tat      4476
Ile Gly Thr His Val Ile His His Leu Phe Pro Gln Ile Pro His Tyr
        300                 305                 310
```

```
cac ttg gtc gat gcc gtgagtgatc tagcttcctc tctctctagt ttcatttgat    4531
His Leu Val Asp Ala
    315 taaatggtga ttaattacta atttaattaa tgaattgtgg acag acg aga gca gct    4587
                                                 Thr Arg Ala Ala
                                                     320 aaa cat gtg tta gga aga tac tac aga gag ccg aag acg tca gga gca    4635
Lys His Val Leu Gly Arg Tyr Tyr Arg Glu Pro Lys Thr Ser Gly Ala
        325                 330                 335 ata ccg att cac ttg gtg gag agt ttg gtc gca agt att aaa aaa gat    4683
Ile Pro Ile His Leu Val Glu Ser Leu Val Ala Ser Ile Lys Lys Asp
340                 345                 350 cat tac gtc agt gac act ggt gat att gtc ttc tac gag aca gat cca    4731
His Tyr Val Ser Asp Thr Gly Asp Ile Val Phe Tyr Glu Thr Asp Pro
355                 360                 365                 370 gat ctc tac gtt tat gct tct gac aaa tct aaa atc aat                4770
Asp Leu Tyr Val Tyr Ala Ser Asp Lys Ser Lys Ile Asn
                375                 380
```

<210> SEQ ID NO 50
<211> LENGTH: 383
<212> TYPE: PRT
<213> ORGANISM: Brassica napus

<400> SEQUENCE: 50

```
Met Val Val Ala Met Tyr Gln Arg Ser Asn Val Asn Gly Asp Ser Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                 240

Gly Val Pro Tyr Ile Ile Phe Val Met Trp Leu Asp Ala Val Thr Tyr
```

```
                      245                 250                 255
Leu His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
                275                 280                 285

Gly Ile Phe Asn Asn Ile His His Asp Ile Gly Thr His Val Ile His
            290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
355                 360                 365

Asp Pro Asp Leu Tyr Val Tyr Ala Ser Asp Lys Ser Lys Ile Asn
            370                 375                 380

<210> SEQ ID NO 51
<211> LENGTH: 1149
<212> TYPE: DNA
<213> ORGANISM: Brassica napus

<400> SEQUENCE: 51
atggttgttg ctatgtacca gcgcagcaat gttaacggag attccggtgc ccggaaggaa      60
gaagggtttg atccaagcgc acaaccaccg tttaagatcg agatataag ggcggcgatt     120 cctaagcatt gctgggtgaa gagtcctttg agatctatga gctacgtcgc cagagacatt     180
ttcgccgtcg cggctctggc catggccgcc gtgtattttg atagctggtt cctctggcca     240
ctctactggg ttgcccaagg aacccttttc tgggccatct tcgttcttgg ccacgactgt     300
ggacatggga gtttctcaga cattcctctg ctgaacagtg tggttggtca cattcttcat     360
tcattcatcc tcgttcctta ccatggttgg agaataagcc atcggacaca ccaccagaac     420
catggccatg ttgaaaacga cgagtcttgg gttccgttgc cagaaaagtt gtacaagaac     480 ttgcccata gtactcggat gctcagatac actgtccctc tgcccatgct cgcttacccg     540
atctatctgt ggtacagaag tcctggaaaa gaagggtcac attttaaccc atacagtagt     600
ttatttgctc caagcgagag gaagcttatt gcaacttcaa ctacttgctg gtccataatg     660
ttggccactc ttgtttatct atcgttcctc gttgatccag tcacagttct caaagtctat     720
ggcgttcctt acattatctt tgtgatgtgg ttggacgctg tcacgtactt gcatcatcat     780
ggtcacgatg agaagttgcc ttggtacaga ggcaaggaat ggagttattt acgtggagga     840
ttaacaacta ttgatagaga ttacggaatc ttcaacaaca tccatcacga cattggaact     900
cacgtgatcc atcatctttt cccacaaatc cctcactatc acttggtcga tgccacgaga     960
gcagctaaac atgtgttagg aagatactac agagagccga agacgtcagg agcaataccg    1020
attcacttgg tggagagttt ggtcgcaagt attaaaaaag atcattacgt cagtgacact    1080
ggtgatattg tcttctacga gacagatcca gatctctacg tttatgcttc tgacaaatct    1140
aaaatcaat                                                            1149
```

BRASSICA PLANTS WITH MODIFIED SEED OIL COMPOSITION

CROSS REFERENCE TO RELATED APPLICATIONS

This application is a 35 U.S.C. 371 National Phase of PCT Application No. PCT/EP2016/059460 filed Apr. 28, 2016, which claims benefit to EP Application No. 15165478.7 filed Apr. 28, 2015, the disclosure of which is hereby incorporated by reference in its entirety.

FIELD OF THE INVENTION

The invention relates to the field of agronomy. Methods and means are provided to modulate fatty acid composition in *Brassica napus* seeds, such as to increase levels of unsaturated fatty acids in *Brassica napus* seeds by modification of FAD2 genes, and to increase levels of oleic acid and decrease the levels of linolenic acid by modification of FAD2 and FAD3 genes.

BACKGROUND OF THE INVENTION

Many plant species store triacylglycerols (TAGs) in their seeds as a carbon reserve. These TAGs are the major source of energy and carbon material that supports seedling development during the early stages of plant life. Vegetable oils from soybean (*Glycine max*), *Brassica* (*Brassica napus* or *B. rapa*), sunflower (*Helianthus annuus*) and many other oilseed crops are also an important source of oil for the human diet or industrial applications including, but not limited to biofuels, biolubricants, nylon precursors, and detergent feedstocks. The degree and/or amount of polyunsaturated fatty acids of vegetable oils are characteristic and determinative properties with respect to oil uses in food or non-food industries. More specifically, the characteristic properties and utilities of vegetable oils are largely determined by their fatty acyl compositions in TAG.

Major vegetable oils are comprised primarily of palmitic (16:0), stearic (18:0), oleic (18:1cis $\Delta^9$), linoleic (18:2cis $\Delta^{9,12}$), and α-linolenic (18:3cis $\Delta^{9,12,15}$ or C18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a monounsaturated fatty acid, while linoleic and linolenic acids are referred to as polyunsaturated fatty acids. Modifications of the fatty acid compositions have been sought after for at least a century in order to provide optimal oil products for human nutrition and chemical (e.g., oleochemical) uses (Gunstone, 1998, Prog Lipid Res 37:277; Broun et al., 1999, Annu Rev Nutr 19:107; Jaworski et al, 2003, Curr Opin Plant Biol 6:178). In particular, the polyunsaturated fatty acids (18:2 and 18:3) have received considerable attention because they are major factors that affect nutritional value and oil stability. However, while these two fatty acids provide essential nutrients for humans and animals, they increase oil instability because they comprise multiple double bonds that may be easily oxidized during processing and storage.

The desaturation of 18:1 into 18:2 is a critical step for synthesizing polyunsaturated fatty acids. During storage lipid biosynthesis, this reaction is known to be catalyzed by the fatty acid desaturase, FAD2, a membrane-bound enzyme located on the endoplasmic reticulum (ER) (Browse and Somerville, 1991, Annu Rev Plant Physiol Plant Mol Biol 42:467), which has delta-12 fatty acid desaturase activity. The FAD2 substrate 18:1 must be esterified on the sn-2 position of phosphatidylcholine (PC) (Miguel and Browse, 1992, J Biol Chem 267:1502; Okuley et al., 1994, Plant Cell 6:147), which is the major membrane phospholipid of plant cells. Not surprisingly, therefore, down-regulation of FAD2 (and FAD3) genes has become a preferred strategy for avoiding the need to hydrogenate vegetable oils and the concomitant production of undesirable trans fatty acids. For example, soybean has both seed-specific and constitutive FAD2 desaturases, so that gene silencing of the seed-specific isoform has allowed the production of high-oleate cultivars (>88% 18:1 in the oil) in which membrane unsaturation and plant performance are largely unaffected.

There are several reports on silencing of FAD2 genes in order to increase the levels of oleic acid. Stoutjesdijk et al., 2000 (Biotech Soc Trans 28:938) discloses *B. napus* plants carrying a Δ12-desaturase (FAD2) co-suppression contstruct having oleic acid levels of up to 89%. Chen et al., 2006 (J Plant Physiol Mol Biol 32: 665) report seed-specific FAD2 gene silencing in *Brassica napus*, which results in oleic acid content in transgenic plant seeds of 83.9%. They further report that the transgenic plants with high oleic acid grow normally and without disadvantageous agronomic traits. Peng et al., 2010, Plant Cell Rep 29:317 disclose *Brassica napus* plants in which FAD2 and the fatty acid elongase 1 (FAE1) genes are simultaneously silenced, reaching oleic acid levels of up to 85%. WO1994/011516 report gene silencing of FAD2 genes in *Brassica napus* resulting in levels of oleic acid of up to 85%. WO2013/112523.

There are also several mutant *Brassica* plants described with increased levels of oleic acid: WO97/21340 and WO98/56239 disclose *Brassica* lines with increased levels of oleic acid, comprising amino acid substitutions in the FAD2 proteins; WO2006/079567 describes a high oleic *Brassica napus* line comprising a nucleotide deletion in a FAD2 gene, leading to a premature translation stop, whereas WO2013/049356 also describes a high oleic *Brassica napus* line comprising a premature translation stop codon in the FAD2 gene leading to a truncated protein; WO2007138444, WO2007/099459, WO2007/107590 and WO2008/084107 describe several mutations in FAD2 genes in *Brassica* lines with high levels of oleic acid.

Wells et al., 2014 (Mol Breeding 33: 349) and WO2012/117256 describe oilseed rape cultivars with a lower than usual polyunsaturated fatty acids content, which has non-functional alleles at three of the four orthologous FAD2 loci. Further mutations in the remaining functional FAD2 copy, leading to amino acid substitutions or premature stop codons, result in a polyunsaturated fatty acids content of about 6%, and an oleic acid content of about 84%.

Significantly, however, canola and other oilseed plants have only constitutive FAD2 enzymes. Therefore, in canola and other such constitutive FAD2 crops, silencing or down-regulation of FAD2 not only alters the fatty acid composition of the storage triacylglycerol (TAG) in seeds, but also of the cellular membranes. For example, the defective FAD2 in the *Arabidopsis* mutant fad2 alters fatty acid compositions of seeds as well as vegetable tissues, and severely compromises plant growth (Browse and Somerville, supra). FAD2 mutations and silencing that produce the highest 18:1 levels in the oil also reduce membrane unsaturation in vegetative and seed tissues, resulting in plants that germinate and grow poorly. As a result, only partial downregulation of FAD2 expression is possible, producing approximately 70-75% 18:1 in the oil of commercial cultivars such as Nexera/Natreon (Dow AgroSciences) and Clear Valley 75 (Cargill).

The object of the current invention is to provide Brassica FAD2 alleles for the production of plants with high levels of oleic acids while maintaining normal agronomic development and, optionally, to combine the FAD2 alleles with FAD5 alleles to produce plants with high levels of oleic acids and low levels of linolenic acids.

SUMMARY OF THE INVENTION

It is a first embodiment of the invention to provide a Brassica napus plant, or a cell, part, seed or progeny thereof, comprising a FAD2-A1, a FAD2-A2, a FAD2-C1 and a FAD2-C2 gene, wherein said plant comprises knock-out fad2 alleles of the FAD2-A1 and of the FAD2-C2 genes, and wherein the fad2 alleles of said FAD2-C1 gene encode a functional FAD2 protein. In a further embodiment, the fad2 alleles of the FAD2-C1 gene of said Brassica napus plant are wild-type alleles. In another embodiment, the fad2 alleles of the FAD2-A2 gene of said Brassica napus plant are knock-out fad2 alleles. In yet another embodiment, the knock-out fad2 allele of said FAD2-A1 gene is a fad2 allele encoding a protein in which the His at a position corresponding to position 109 of SEQ ID NO: 6 is substituted with another amino acid, and wherein said knock-out fad2 allele of said FAD2-C2 allele is a fad2 allele comprising a stop codon mutation in the codon encoding the Trp at a position corresponding to position 190 of SEQ ID NO: 15, whereas in yet another embodiment said knock-out fad2 allele of said FAD2-A1 gene comprises a sequence having at least 90% sequence identity to SEQ ID NO: 4 wherein the C at position 2371 is substituted with T; and said knock-out fad2 allele of said FAD2-C2 gene comprises a sequence having at least 90% sequence identity to SEQ ID NO: 13 wherein the G at position 2327 is substituted with A. In again another embodiment, the Brassica napus plant, or a cell, part, seed or progeny thereof according to the invention is derivable or obtainable from seeds selected from the group consisting of seed comprising HIOL101 having been deposited at NCIMB under accession number NCIMB 42376; and seed comprising HIOL109 having been deposited at NCIMB under accession number NCIMB 42375. In another aspect of the invention, said Brassica napus plant, or a cell, part, seed or progeny thereof, is homozygous for any one of the knock-out fad2 alleles.

In a further embodiment, the Brassica napus plant, or a cell, part, seed or progeny thereof, according to the invention, further comprises at least a knock-out fad3 allele of at least one FAD3 gene, such as knock-out fad3 alleles of five FAD3 genes. In another embodiment, said FAD3 genes are selected from the group consisting of: a) a FAD3-A1 gene comprising a sequence having at least 90% sequence identity to the sequence of SEQ ID NO: 37, or having a cDNA sequence having at least 90% sequence identity to the sequence of SEQ ID NO: 39, or encoding a protein having at least 90% sequence identity to the sequence of SEQ ID NO: 38; b) a FAD3-A2 gene comprising a sequence having at least 90% sequence identity to the sequence of SEQ ID NO: 40, or having a cDNA sequence having at least 90% sequence identity to the sequence of SEQ ID NO: 42, or encoding a protein having at least 90% sequence identity to the sequence of SEQ ID NO: 41; c) a FAD3-A3 gene comprising a sequence having at least 90% sequence identity to the sequence of SEQ ID NO: 43, or having a cDNA sequence having at least 90% sequence identity to the sequence of SEQ ID NO: 45, or encoding a protein having at least 90% sequence identity to the sequence of SEQ ID NO: 44; d) a FAD3-C1 gene comprising a sequence having at least 90% sequence identity to the sequence of SEQ ID NO: 46, or having a cDNA sequence having at least 90% sequence identity to the sequence of SEQ ID NO: 48, or encoding a protein having at least 90% sequence identity to the sequence of SEQ ID NO: 47; and e) a FAD3-C2 gene comprising a sequence having at least 90% sequence identity to the sequence of SEQ ID NO: 49, or having a cDNA sequence having at least 90% sequence identity to the sequence of SEQ ID NO: 51, or encoding a protein having at least 90% sequence identity to the sequence of SEQ ID NO: 50. In yet a further embodiment, said fad3 alleles are a) a mutant allele of said FAD3-A1 gene comprises a G to A substitution at a position corresponding to position 2405 of SEQ ID NO: 37; b) a mutant allele of said FAD3-A2 gene comprises a G to A substitution at a position corresponding to position 3934 of SEQ ID NO: 40; c) a mutant allele of said FAD3-A3 gene comprises a G to A substitution at a position corresponding to position 2847 of SEQ ID NO: 43; d) a mutant allele of said FAD3-C1 gene comprises a G to A substitution at a position corresponding to position 2702 of SEQ ID NO: 46; and e) a mutant allele of said FAD3-C2 gene comprises a G to A substitution at a position corresponding to position 3909 of SEQ ID NO: 49.

In a further aspect, the Brassica napus plant, or a cell, part, seed or progeny thereof according to the invention has increased levels of C18:1 in the seed oil, such as a level of C18:1 in the seed oil of between about 73% to about 75%, and which maintains normal agronomic development. In another aspect, the Brassica napus plant or a cell, part, seed or progeny thereof, according to the invention, which comprises mutant fad2 alleles and mutant fad3 alleles, has increased levels of C18:1 and decreased levels of C18:3 in the seed oil. Also provided is oil from the seeds according to the invention.

Another aspect of the invention provides a method for increasing the levels of C18:1 in seed oil while maintaining normal agronomic development, said method comprising introducing a knock-out fad2 allele of a FAD2-A1 gene and a knock-out fad2 allele of a FAD2-C2 gene into a Brassica napus plant, and selecting a Brassica napus plant comprising said knock-out fad2 allele of said FAD2-A1 gene, and said knock-out fad2 allele of said FAD2-C2 gene, which further contains a FAD2-C1 gene of which the fad2 alleles encode a functional FAD2 protein. In a further embodiment, the Brassica plant produced by said method comprises knock-out fad2 alleles of the FAD2-A2 gene.

Another aspect of the invention provides a method for increasing the levels of C18:1 and decreasing the levels of C18:3 in seed oil while maintaining normal agronomic development, said method comprising introducing a knock-out fad2 allele of a FAD2-A1 gene and a knock-out fad2 allele of a FAD2-C2 gene, and a knock-out fad3 allele of a FAD3-A1 gene, a knock-out fad3 allele of a FAD3-A2 gene, a knock-out fad3 allele of a FAD3-A3 gene, a knock-out fad3 allele of a FAD3-C1 gene, and a knock-out fad3 allele of a FAD3-C2 gene, into a Brassica napus plant, and selecting a Brassica napus plant comprising said knock-out fad2 allele of said FAD2-A1 gene, and said knock-out fad2 allele of said FAD2-C2 gene, said knock-out fad3 allele of said FAD3-A1 gene, said knock-out fad3 allele of said FAD3-A2 gene, said knock-out fad3 allele of said FAD3-A3 gene, said knock-out fad3 allele of said FAD3-C1 gene, and said knock-out fad3 allele of said FAD3-C2 gene, which further contains a FAD2-C1 gene of which the fad2 alleles encode a functional FAD2 protein, and a FAD2 A2 gene of which the fad2 alleles are knock-out fad2 alleles.

In yet another embodiment, the method according to the invention comprises the step of selecting said *Brassica napus* plant comprising said knock-out fad2 allele of said FAD2-A1 gene and said knock-out fad2 allele of said FAD2-C2 gene by analyzing genomic DNA from said plant for the presence of at least one molecular marker, wherein at least one molecular marker is linked to said knock-out fad2 allele of said FAD2-A1 gene and wherein at least one molecular marker is linked to said knock-out fad2 allele of said FAD2-C2 gene and, optionally, wherein at least one molecular marker is linked to one or more fad2 alleles of said FAD2 A2 gene or of said FAD2-C1 gene, or to one or more fad3 alleles of said FADS A1 gene, said FADS-A2 gene, said FADS A3 gene, said FAD3-C1 gene, or said FAD3-C2 gene.

In a further embodiment, a method is provided to determine the presence or absence of a knock-out fad2 allele in a biological sample, comprising providing genomic DNA from said biological sample, and analyzing said DNA for the presence of at least one molecular marker, wherein the at least one molecular marker is linked to said knock-out fad2 allele. Yet another embodiment provides a kit for the detection of a knock-out fad2 allele in *Brassica* DNA samples, wherein said kit comprises one or more PCR primer pairs, which are able to amplify a DNA marker linked to said knock-out fad2 allele. Another embodiment provides a method for determining the zygosity status of a knock-out fad2 allele in a plant, or a cell, part, seed or progeny thereof, comprising determining the presence of a knock-out and/or a corresponding wild type FAD2 specific region in the genomic DNA of said plant, or a cell, part, seed or progeny thereof.

In another embodiment, a method is provided for combining at least one knock-out fad2 allele of a FAD2-A1 gene, with at least one knock-out fad2 allele of a FAD2-C2 gene in a single *Brassica napus* plant, said method comprising a) generating and/or identifying two or more plants each comprising one or more selected knock-out fad2 alleles; b) crossing a first plant comprising one or more selected knockout fad2 alleles with a second plant comprising one or more other selected knockout fad2 alleles; c) collecting seeds from the cross, and, optionally, identifying a plant comprising at least one knock-out fad2 allele of a FAD2-A1 gene and at least one knock-out fad2 allele of a FAD2-C2 gene; and, optionally d) repeat steps b) and c) until a plant comprising at least one knock-out fad2 allele of a FAD2-A1 gene and at least one knock-out fad2 allele of a FAD2-C2 gene, is obtained. In another embodiment, said plant obtained in step d) comprises at least one knock-out fad2 allele of a FAD2-A1 gene and at least one knock-out fad2 allele of a FAD2-C2 gene, comprises a FAD2-C1 gene of which the fad2 alleles encode a functional FAD2 protein and comprises a FAD2 A2 gene of which the fad2 alleles are knock-out fad2 alleles.

In a further aspect of the invention, a knock-out fad2 allele of a FAD2 gene is provided, wherein the knock-out fad2 allele is a mutated version of the native FAD2 gene, wherein the native FAD2 gene is selected from the group consisting of: (a) a FAD2-A1 gene comprising a sequence having at least 90% sequence identity to the sequence of SEQ ID NO: 4, or having a cDNA sequence having at least 90% sequence identity to the sequence of SEQ ID NO: 5, or encoding a protein having at least 90% sequence identity to the sequence of SEQ ID NO: 6; and (b) a FAD2-C2 gene comprising a sequence having at least 90% sequence identity to the sequence of SEQ ID NO: 13, or having a cDNA sequence having at least 90% sequence identity to the sequence of SEQ ID NO: 14, or encoding a protein having at least 90% sequence identity to the sequence of SEQ ID NO: 15, such as a knock-out fad2 allele which is a mutant allele of said FAD2-A1 gene comprising a C to T substitution at a position corresponding to position 2371 of SEQ ID NO: 4; or which is a mutant allele of said FAD2-C2 gene comprising a G to A substitution at a position corresponding to position 2327 of SEQ ID NO: 52.

In a further embodiment, a method is provided for producing oil, comprising harvesting seeds from the plants according to the invention, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the plant or a part thereof according to the invention, and preparing the food, feed or industrial product from the plant or part thereof.

Another embodiment provides the use of the knock-out fad2 allele according to the invention to increase the level of C18:1 in the seed oil of a *Brassica napus* plant while maintaining normal agronomic development. Yet another embodiment provides a method to produce a *Brassica napus* plant comprising an increased level of C18:1 in the seed oil and which maintains normal agronomic development, said method comprising sowing seeds according to the invention and growing plants from said seeds.

BRIEF DESCRIPTION OF THE FIGURES

FIG. 1. Alignment of the *Arabidopsis* and *Brassica* FAD2 protein sequences. Boxes indicate the conserved domains: TM=transmembrane or membrane-associated domain; HIS=Histidine box; ER=ER retrieval motif. Amino acids of which the codons are mutated in the mutant fad2 alleles of the current invention are indicated bold, underlined capitals.

GENERAL DEFINITIONS

Figure 2:
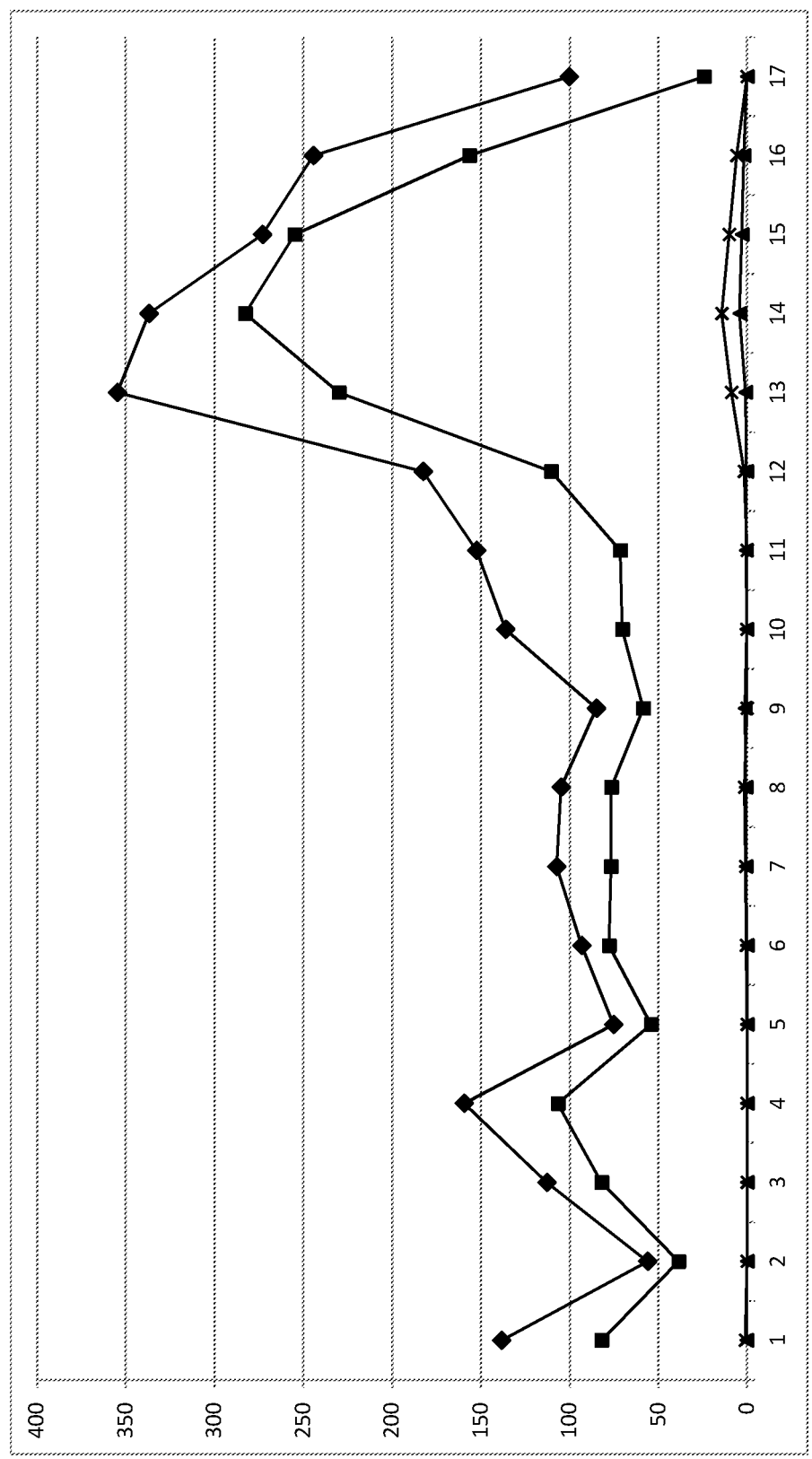
FIG. 2. Relative expression of *Brassica napus* FAD2 genes. Diamonds: BnFAD2-A1; squares: BnFAD2-C1; triangles: BnFAD2-A2; crosses: BnFAD2-C2. 1: root, 2 weeks old plant; 2: Cotyledons, 10 days after sowing (DAS); 3: stem 15 DAS; 4: stem, 33 DAS; 5: young leaf, 33 DAS; 6: apical meristem+smallest leaf, 33 DAS; 7: small flowerbud, 42 DAS; 8: big flower bud, 42 DAS>5 mm; 9: open flower, 52 DAS; 10: pod, 14-20 DAF; 11: pod, 21-25 DAF; 12: seeds, 14-20 DAF; 13: seeds, 21-25 DAF; 14: seeds, 26-30 DAF; 15: seeds, 31-35 DAF; 16: seeds, 42 DAF; 17: seeds, 49 DAF.

A "FAD2 gene" or "FAD2 allele", as used herein, is a gene or allele comprising a sequence having at least 60% sequence identity to the coding sequence of the FAD2 gene of *Arabidopsis thaliana*, accession number At3G12120, as depicted in SEQ ID NO: 2, nts 177-1328.

A FAD2 gene or FAD2 allele can, but does not need to encode a functional FAD2 protein. Functionality of the FAD2 protein can be tested, for example, by complementation of the *Arabidopsis* fad2-1 mutant as described by Okuley et al., 1994, Plant Cell 6: 147, or by expression and activity analysis in yeast as described by Peyou-Ndi et al., Arch Biochem Biophys 376:399. "FAD2 genes" or "FAD2 alleles" encompass, but are not limited to, BnFAD2-A1, BnFAD2-A2, BnFAD2-C1, BnFAD2-C2, BrFAD1-1, BrFAD2-2, BoFAD2-1 and BoFAD2-2 genes or alleles.

A "knock-out fad2 gene" or "knock-out fad2 allele" as used herein is a fad2 gene or a fad2 allele which encodes no functional FAD2 protein, or which encodes a FAD2 protein with reduced activity. Said "knock-out fad2 gene" can encode a FAD2 protein with reduced functionality, or be a full knock-out fad2 gene, encoding no functional FAD2 protein. Said "knock-out fad2 gene" or "knock-out fad2 allele" can be a mutant fad2 allele or a mutant fad2 gene, which may encode no functional FAD2 protein, or which may encode a mutant FAD2 protein with reduced activity. The gene or allele may also be referred to as an inactivated gene or allele. A knock-out fad2 gene or allele can be a wild-type FAD2 gene, i.e. a wild-type FAD2 gene which encodes no functional FAD2 protein, or which encodes a FAD2 protein with reduced activity, or can be a mutant fad2 gene or allele.

A "full knock-out" or "null" fad2 allele, as used herein, refers to a fad2 allele, which encodes a FAD2 protein having no biological activity as compared to a functional FAD2 protein (such as, for example, the wild-type BnFAD2-A1 protein of SEQ ID NO: 6, or the wild-type BnFAD2-C1 protein of SEQ ID NO: 9), or no detectable biological activity in a yeast assay as described by Peyou-Ndi et al., Arch Biochem Biophys 376:399, or which encodes no protein at all. Such a "full knock-out fad2 allele" is, for example, a wild-type fad2 allele, which comprises one or more mutations in its nucleic acid sequence, for example, one or more non-sense or mis-sense mutations. In particular, such a full knock-out fad2 allele is a wild-type fad2 allele, which comprises a mutation that preferably result in the production of a FAD2 protein lacking at least one functional domain, such as at least one of the three Histidine boxes, or at least one of the five transmembrane or membrane-associated domains (TM domains), or the ER retrieval motif, such that the biological activity of the FAD2 protein is completely abolished, or whereby the mutation(s) preferably result in no production of a FAD2 protein.

A "functional FAD2 gene" or "functional FAD2 allele" as used herein is a FAD2 gene or a FAD2 allele which encodes a functional FAD2 protein.

A "mutant fad2 gene" or "mutant fad2 allele" as used herein refers to any fad2 gene or fad2 allele which is not found in plants in the natural population or breeding population, but which is produced by human intervention such as mutagenesis or gene targeting. A mutant fad2 allele comprises knock-out fad2 alleles, and functional FAD2 alleles. A mutant fad2 allele can also be referred to as an "induced mutant fad2 allele".

Functional FAD2 protein is a FAD2 protein which has at least 10%, or at least 15%, or at least 20%, or at least 25%, or at least 30%, or at least 50%, or at least 80% of the activity of the protein encoded by a reference *Brassica napus* FAD2-A1 or FAD2-C1 gene, as tested, for example, in yeast as described by by Peyou-Ndi et al., Arch Biochem Biophys 376:399, wherein the reference *Brassica napus* FAD2-A1 and FAD2-C1 gene encodes the protein with the amino acid sequence as depicted in SEQ ID No. 6 and SEQ ID No. 9, respectively. A functional FAD2 protein may be a FAD2 protein with "full functionality", which can be 100% functionality of the reference *Brassica napus* FAD2-A1 and FAD2-C1 proteins. A functional FAD2 protein may also be a FAD2 protein with reduced functionality. The activity of a functional FAD2 protein should however not be completely abolished. For example, a functional FAD2 protein has detectable FAD2 activity in a yeast assay as described by Peyou-Ndi et al., Arch Biochem Biophys 376:399.

"Biological activity" of a FAD2 protein as used herein is delta-12 desaturation of oleic acid (C18:1) to form linoleic acid (C18:2). The biological activity of a FAD2 protein can, for example, be determined in a yeast assay as described by Peyou-Ndi et al., Arch Biochem Biophys 376:399.

A mutant FAD2 protein with reduced functionality is a FAD2 protein encoded by a mutant fad2 gene which has reduced activity or a reduction in the biological activity, or a significant reduction in the biological activity, as compared to the corresponding wild-type FAD2 protein encoded by the wild-type FAD2 gene, but not completely abolished. Said activity may be a reduced with at least 10%, or at least 20%, or at least 30%, or at least 40%, or at least 50%, or at least 60%, or at least 70%, or at least 80%, or at least 90%, or at least 93%, or at least 95%, but wherein the activity is not completely abolished. For example, a mutant FAD2 protein with reduced functionality has detectable FAD2 activity in a yeast assay as described by Peyou-Ndi et al., Arch Biochem Biophys 376:399. A significant reduction in the biological activity of the FAD2 protein refers herein to a reduction in the delta-12 fatty acid desaturase activity, such that the levels of C18:1 in a plant are increased as compared to a plant expressing the corresponding wild type FAD2 protein.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an FAD2 gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of a FAD2 protein may thus still be referred to as a "protein". An "isolated protein" is used to refer to a protein that is no longer in its natural environment, for example in vitro or in a recombinant bacterial or plant host cell. "Amino acids" are the principal building blocks of proteins and enzymes. They are incorporated into proteins by transfer RNA according to the genetic code while messenger RNA is being decoded by ribosomes. During and after the final assembly of a protein, the amino acid content dictates the spatial and biochemical properties of the protein or enzyme. The amino acid backbone determines the primary sequence of a protein, but the nature of the side chains determines the protein's properties. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbors ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found. For example, the "FAD2-A1 locus" and the "FAD2-A2 locus" refers to the position on a chromosome of the A genome where the FAD2-A1 gene (and two FAD2-A1 alleles) or the FAD2-A2 gene (and two FAD2-A2 alleles) may be found, such as the position on the chromosome of the A genome of the BnFAD2-A1 locus, the BnFAD2-A2 locus, the BrFAD2-1 locus, and the BnFAD2-2 locus, while the"FAD2-C1 locus" and the "FAD2-C2 locus" refers to the position on a chromosome of the C genome where the FAD2-C1 gene (and two FAD2-C1 alleles) or the BnFAD2-C2 gene (and two FAD2-C2 alleles) may be found, such as the position on the chromosome of the C genome of the BnFAD2-C1 locus, the BnFAD2-C2 locus, the BoFAD2-1 locus, and the BoFAD2-2 locus.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants.

"Mutant" as used herein refers to a form of a plant or a gene which is different from such plant or gene in the natural population, and which is produced by human intervention, e.g. by mutagenesis, and a "mutant allele" refers to an allele which is not found in plants in the natural population or breeding population, but which is produced by human intervention such as mutagenesis or gene targeting.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the increased levels of C18:1), such as seed obtained by selfing or crossing, e.g. hybrid seed (obtained by crossing two inbred parental lines), hybrid plants and plant parts derived there from are encompassed herein, unless otherwise indicated.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

A "molecular assay" (or test) refers herein to an assay that indicates (directly or indirectly) the presence or absence of one or more particular FAD2 alleles at one or more FAD2 loci (e.g. at one or both of the FAD2-A1, FAD2-A2, FAD2-C1 or FAD2-C2 loci). In one embodiment it allows one to determine whether a particular (wild type or mutant) FAD2 allele is homozygous or heterozygous at the locus in any individual plant.

"Mutagenesis", as used herein, refers to the process in which plant cells (e.g., a plurality of Brassica seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet 13:152-156), transposon mutagenesis (McKenzie et al. (2002) Theor Appl Genet 105:23-33), or tissue culture mutagenesis (induction of somaclonal variations), or a combination of two or more of these. Thus, the desired mutagenesis of one or more FAD2 alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, *Brassica* plants are regenerated from the treated cells using known techniques. For instance, the resulting *Brassica* seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant fad2 alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant fad2 alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150. Gene targeting can be used to create mutant fad2 alleles, such as knock-out fad2 alleles.

As used herein, the term "non-naturally occurring" or "cultivated" when used in reference to a plant, means a plant with a genome that has been modified by man. A transgenic plant, for example, is a non-naturally occurring plant that contains an exogenous nucleic acid molecule, e.g., a chimeric gene comprising a transcribed region which when transcribed yields a biologically active RNA molecule capable of reducing the expression of an endogenous gene, such as a FAD2 gene, and, therefore, has been genetically modified by man. In addition, a plant that contains a mutation in an endogenous gene, for example, a mutation in an endogenous FAD2 gene, (e.g. in a regulatory element or in the coding sequence) as a result of an exposure to a mutagenic agent is also considered a non-naturally plant, since it has been genetically modified by man. Furthermore, a plant of a particular species, such as *Brassica napus*, that contains a mutation in an endogenous gene, for example, in an endogenous FAD2 gene, that in nature does not occur in that particular plant species, as a result of, for example, directed breeding processes, such as marker-assisted breeding and selection or introgression, with a plant of the same or another species, such as *Brassica juncea* or *rapa*, of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the *Brassica napus* FAD2 genes may thus be identified in other plant species (e.g. *Brassica juncea*, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

The current invention is based on the identification of two FAD2 genes in *Brassica rapa* and in *Brassica oleracea*, and of 4 FAD2 genes in *Brassica napus*, and of the role of the *Brassica* FAD2 gene products in fatty acid desaturation.

It is a first embodiment of the invention to provide a *Brassica napus* plant, or a cell, part, seed or progeny thereof, comprising a FAD2-A1, a FAD2-A2, a FAD2-C1 and a FAD2-C2 gene, wherein said plant comprises knock-out fad2 alleles of the FAD2-A1 and of the FAD2-C2 genes, and wherein the fad2 alleles of said FAD2-C1 gene encode a functional FAD2 protein. In a further embodiment, the fad2 alleles of the FAD2-C1 gene of said *Brassica napus* plant are wild-type alleles. In another embodiment, the fad2 alleles of the FAD2-A2 gene of said *Brassica napus* plant are knock-out fad2 alleles. In yet another embodiment, the knock-out fad2 allele of said FAD2-A1 gene is a fad2 allele encoding a protein in which the His at a position corresponding to position 109 of SEQ ID NO: 6 is substituted with another amino acid, and wherein said knock-out fad2 allele of said FAD2-C2 allele is a fad2 allele comprising a stop codon mutation in the codon encoding the Trp at a position corresponding to position 190 of SEQ ID NO: 15, whereas in yet another embodiment said knock-out fad2 allele of said FAD2-A1 gene comprises a sequence having at least 90% sequence identity to SEQ ID NO: 4 wherein the C at position 2371 is substituted with T; and said knock-out fad2 allele of said FAD2-C2 gene comprises a sequence having at least 90% sequence identity to SEQ ID NO: 13 wherein the G at position 2327 is substituted with A. In again another embodiment, the *Brassica napus* plant, or a cell, part, seed or progeny thereof according to the invention is derivable or obtainable from seeds selected from the group consisting of seed comprising HIOL101 having been deposited at NCIMB under accession number NCIMB 42376; and seed comprising HIOL109 having been deposited at NCIMB under accession number NCIMB 42375. In another aspect of the invention, said *Brassica napus* plant, or a cell, part, seed or progeny thereof, is homozygous for any one of the knockout fad2 alleles.

In a further embodiment, the *Brassica napus* plant, or a cell, part, seed or progeny thereof, according to the invention, further comprises at least a knock-out fad3 allele of at least one FAD3 gene, such as knock-out fad3 alleles of five FAD3 genes. In another embodiment, said FAD3 genes are selected from the group consisting of: a) a FAD3-A1 gene comprising a sequence having at least 90% sequence identity to the sequence of SEQ ID NO: 37, or having a cDNA sequence having at least 90% sequence identity to the sequence of SEQ ID NO: 39, or encoding a protein having at least 90% sequence identity to the sequence of SEQ ID NO: 38; b) a FAD3-A2 gene comprising a sequence having at least 90% sequence identity to the sequence of SEQ ID NO: 40, or having a cDNA sequence having at least 90% sequence identity to the sequence of SEQ ID NO: 42, or encoding a protein having at least 90% sequence identity to the sequence of SEQ ID NO: 41; c) a FAD3-A3 gene comprising a sequence having at least 90% sequence identity to the sequence of SEQ ID NO: 43, or having a cDNA sequence having at least 90% sequence identity to the sequence of SEQ ID NO: 45, or encoding a protein having at least 90% sequence identity to the sequence of SEQ ID NO: 44; d) a FAD3-C1 gene comprising a sequence having at least 90% sequence identity to the sequence of SEQ ID NO: 46, or having a cDNA sequence having at least 90% sequence identity to the sequence of SEQ ID NO: 48, or encoding a protein having at least 90% sequence identity to the sequence of SEQ ID NO: 47; and e) a FAD3-C2 gene comprising a sequence having at least 90% sequence identity to the sequence of SEQ ID NO: 49, or having a cDNA sequence having at least 90% sequence identity to the sequence of SEQ ID NO: 51, or encoding a protein having at least 90% sequence identity to the sequence of SEQ ID NO: 50. In yet a further embodiment, said fad3 alleles are a) a mutant allele of said FAD3-A1 gene comprises a G to A substitution at a position corresponding to position 2405 of SEQ ID NO: 37; b) a mutant allele of said FAD3-A2 gene comprises a G to A substitution at a position corresponding to position 3934 of SEQ ID NO: 40; c) a mutant allele of said FAD3-A3 gene comprises a G to A substitution at a position corresponding to position 2847 of SEQ ID NO: 43; d) a mutant allele of said FAD3-C1 gene comprises a G to A substitution at a position corresponding to position 2702 of SEQ ID NO: 46; and e) a mutant allele of said FAD3-C2 gene comprises a G to A substitution at a position corresponding to position 3909 of SEQ ID NO: 49.

A *Brassica* plant, as used herein, can be *Brassica napus* (AACC, 2n=38), *Brassica juncea* (AABB, 2n=36), *Brassica*

*carinata* (BBCC, 2n=34), *Brassica rapa* (syn. *B. campestris*) (AA, 2n=20), *Brassica oleracea* (CC, 2n=18) or *Brassica nigra* (BB, 2n=16). Said *Brassica* plant can be a crop plant species cultivated as a crop.

Nucleic Acid Sequences According to the Invention

Provided are both wild type FAD2 nucleic acid sequences encoding functional FAD2 proteins and mutant fad2 nucleic acid sequences (comprising one or more mutations, preferably mutations which result in no or a significantly reduced biological activity of the encoded FAD2 protein or in no FAD2 protein being produced) of FAD2 genes from *Brassica*, especially from *Brassica napus, Brassica rapa*, and *Brassica oleracea*.

However, isolated FAD2 and fad2 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of FAD2-A1, FAD2-C1, FAD2-A2, and FAD2-C2 have been isolated from *Brassica napus*, nucleic acid sequences of FAD2-1, and FAD2-2 have been isolated from *Brassica oleracea* and from *Brassica rapa* as depicted in the sequence listing. The wild type FAD2 sequences are depicted, while the mutant fad2 sequences of these sequences, and of sequences essentially similar to these, are described herein below and in the Examples, with reference to the wild type FAD2 sequences. The genomic FAD2 protein-encoding DNA from *Brassica napus, Brassica oleracea*, and *Brassica rapa* do comprise any introns. The coding sequences or cDNA sequences, of the *Brassica* FAD2 genes, not comprising the introns, are also depicted in the sequence listing.

A "*Brassica napus* FAD2-A1 gene", "BnFAD2-A1 gene", *Brassica napus* FAD2-A1 allele", "BnFAD2-A1 allele" or "FAD2-A1 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 4.

A "*Brassica napus* FAD2-C1 gene", "BnFAD2-C1 gene", *Brassica napus* FAD2-C1 allele", "BnFAD2-C1 allele" or "FAD2-C1 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 7.

A "*Brassica napus* FAD2-A2 gene", "BnFAD2-A2 gene", *Brassica napus* FAD2-A2 allele", "BnFAD2-A2 allele" or "FAD2-A2 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 10.

A "*Brassica napus* FAD2-C2 gene", "BnFAD2-C2 gene", *Brassica napus* FAD2-C2 allele", "BnFAD2-C2 allele" or "FAD2-C2 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 13.

A "*Brassica rapa* FAD2-1 gene", "BrFAD2-1 gene", *Brassica rapa* FAD2-1 allele", "BrFAD2-1 allele" or "FAD2-1 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 16.

A "*Brassica rapa* FAD2-2 gene", "BrFAD2-2 gene", *Brassica rapa* FAD2-2 allele", "BrFAD2-2 allele" or "FAD2-2 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 19.

A "*Brassica oleracea* FAD2-1 gene", "BoFAD2-1 gene", *Brassica oleracea* FAD2-1 allele", "BoFAD2-1 allele" or "FAD2-1 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 22.

A "*Brassica oleracea* FAD2-2 gene", "BoFAD2-2 gene", *Brassica oleracea* FAD2-2 allele", "BoFAD2-2 allele" or "FAD2-2 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 25.

A "FAD2-A1 gene" or a "FAD2-A1 allele" can be a BnFAD2-A1 gene or allele, or can be a BrFAD2-1 gene or allele.

A "FAD2-C1 gene" or a "FAD2-C1 allele" can be a BnFAD2-C1 gene or allele, or can be a BoFAD2-1 gene or allele.

A "FAD2-A2 gene" or a "FAD2-A2 allele" can be a BnFAD2-A2 gene or allele, or can be a BrFAD2-2 gene or allele.

A "FAD2-C2 gene" or a "FAD2-C2 allele" can be a BnFAD2-C2 gene or allele, or can be a BoFAD2-2 gene or allele.

Thus the invention provides both nucleic acid sequences encoding wild type, functional FAD2 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type FAD2 protein. Preferably the mutation(s) in the nucleic acid sequence result in one or more amino acid changes (i.e. in relation to the wild type amino acid sequence one or more amino acids are inserted, deleted and/or substituted) whereby the biological activity of the FAD2 protein is significantly reduced or completely abolished.

Functionality of the FAD2 protein can be tested, for example, by expression and activity analysis in yeast as described by Peyou-Ndi et al., Arch Biochem Biophys 376:399.

Both endogenous and isolated nucleic acid sequences are provided herein. Also provided are fragments of the FAD2 sequences and FAD2 variant nucleic acid sequences defined above, for use as primers or probes and as components of kits according to another aspect of the invention (see further below). A "fragment" of a FAD2 or fad2 nucleic acid sequence or variant thereof (as defined) may be of various lengths, such as at least 10, 12, 15, 18, 20, 50, 100, 200, 500, 600 contiguous nucleotides of the FAD2 or fad2 sequence (or of the variant sequence).

Wild-Type Nucleic Acid Sequences Encoding Wild-Type FAD2 Proteins

The nucleic acid sequences depicted in the sequence listing encode wild type FAD2 proteins from *Brassica napus*, from *Brassica rapa*, and from *Brassica oleracea*. Thus, these sequences are endogenous to the *Brassica* plants from which they were isolated.

Other *Brassica* crop species, varieties, breeding lines or wild accessions may be screened for other FAD2 alleles, encoding the same FAD2 proteins or variants thereof. For example, nucleic acid hybridization techniques (e.g. Southern blot analysis, using for example stringent hybridization conditions) or nucleic acid amplification-based techniques such as PCR techniques may be used to identify FAD2 alleles endogenous to other *Brassica* plants, such as various *Brassica napus*, *Brassica rapa*, or *Brasssica oleracea* varieties, lines or accessions. To screen such plants, plant organs or tissues for the presence of FAD2 alleles, the FAD2 nucleic acid sequences provided in the sequence listing, or variants or fragments of any of these, may be used. For example whole sequences or fragments may be used as probes or primers. For example specific or degenerate primers may be used to amplify nucleic acid sequences encoding FAD2 proteins from the genomic DNA of the plant, plant organ or tissue. These FAD2 nucleic acid sequences may be isolated and sequenced using standard molecular biology techniques. Bioinformatics analysis may then be used to characterize the allele(s), for example in order to determine which FAD2 allele the sequence corresponds to and which FAD2 protein or protein variant is encoded by the sequence.

In addition, it is understood that FAD2 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below.

Wild-type FAD2 nucleic acid sequences may encompass knock-out FAD2 nucleic acid sequences, such as the full knock-out BnFAD2-A2 and BrFAD2-2 nucleic acid sequence of SEQ ID NO: 10 and 19, respectively, as described herein, which contain a deletion in the coding sequence leading to a truncated protein of 136 amino acids (SEQ ID NO: 12 and 21, respectively) which lack the five TM domains, the three Histidine boxes, and the ER retrieval motif (see FIG. 1), and such as the knock-out BoFAD2-2 nucleic acid sequence of SEQ ID NO: 25 as described herein, which contains a 1 nt deletion deletion at a position corresponding to position 2608 of the BnFAD2-C2 gene (SEQ ID NO: 13) (i.e. the position after position 2726 of the BoFAD2-2 gene, resulting in a frameshift mutation, leading to a truncated protein of 290 amino acids (SEQ ID NO: 27) which lacks third Histidine box and the ER retrieval motif (see FIG. 1). Thus, knock-out fad2 alleles of the FAD2-A2 gene can be wild-type FAD2 alleles of the FAD2-A2 gene.

Nucleic Acid Sequences Encoding Mutant FAD2 Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as fad2 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded FAD2 protein (i.e. it is not a "silent mutation"). In another embodiment, the mutation(s) in the nucleic acid sequence result in a significantly reduced or completely abolished biological activity of the encoded FAD2 protein relative to the wild type protein.

Basically, any mutation in the wild type FAD2 nucleic acid sequences which results in a FAD2 protein comprising at least one amino acid insertion, deletion and/or substitution relative to the wild type FAD2 protein can lead to significantly reduced or no biological activity. It is, however, understood that certain mutations in the FAD2 protein are more likely to result in a complete abolishment of the biological activity of the FAD2 protein, such as mutations whereby significant portions of conserved domains, such as one or more of the Histidine boxes are lacking, or whereby certain critical amino acid residues within these domains are lacking or substituted, preferably substituted by non-similar or non-conservative amino acids, while other mutations such as for example amino acid substitutions outside of the Histidine boxes or within the TM domain, are more likely to result in a reduction of the biological activity of the FAD2 protein without completely abolishing the biological activity of the encoded FAD2 protein.

The conserved first, second and third Histidine boxes are at a position corresponding to position 105-109, 141-145, and 314-319, respectively, of the *Arabidopsis* FAD2 protein of SEQ ID NO: 3. The conserved first, second, third, fourth and fifth TM domains are at a position corresponding to position 56-76, 117-137, 179-199, 225-245, and 252-272, respectively, of the *Arabidopsis* FAD2 protein of SEQ ID NO: 3. The conserved ER retrieval motif is at a position corresponding to position 379-383 of the *Arabidopsis* FAD2 protein of SEQ ID NO: 3.

Optimal alignment of the *Arabidopsis* FAD2 nucleic acids (SEQ ID NO: 1 and 2) and amino acid (SEQ ID NO: 3) sequences with *Brassica* FAD2 sequences of the present invention, allows to determine the positions of the corresponding conserved domains and amino acids in these *Brassica* sequences.

Thus, the conserved first Histidine box is at a position corresponding to position 105-109 of SEQ ID NO: 6, 9, 15, 18, 24 and 27; the conserved second Histidine box is at a position corresponding to position 141-145 of SEQ ID NO: 6, 9, 15, 18, 24 and 27; the conserved third Histidine box is at a position corresponding to position 316-320 of SEQ ID NO: 6, 9, 15, 18, and 24; the conserved first TM domain is at a position corresponding to position 56-76 of SEQ ID NO: 6, 9, 15, 18, 24 and 27; the conserved second TM domain is at a position corresponding to position 117-137 of SEQ ID NO: 6, 9, 15, 18, 24 and 27; the conserved third TM domain is at a position corresponding to position 179-199 of SEQ ID NO: 6, 9, 15, 18, 24 and 27; the conserved fourth TM domain is at a position corresponding to position 226-246 of SEQ ID NO: 6, 9, 15, 18, 24 and 27; the conserved fifth TM domain is at a position corresponding to position 253-273 of SEQ ID NO: 6, 9, 15, 18, 24 and 27; and the ER retrieval motif is at a position corresponding to position 380-384 of SEQ ID NO: 6, 9, 15, 18, and 24.

The present invention describes knockout fad2 alleles, which can be full knock-out alleles, in particular e.g. the HIOL101 allele, encoding a FAD2 protein in which the conserved Histidine (His, H) at position 5 of the first Histidine box (i.e. at a position corresponding to position 109 of SEQ ID NO: 3) is substituted with a Tyrosine; the HIOL103 allele, encoding a FAD2 protein which is truncated after the amino acid at a position corresponding to position 100 of SEQ ID NO: 3, and lacks the three Histidine boxes, the second, the third, the fourth and the fifth TM domain, and the ER retrieval motif; the HIOL111 allele, comprising a stop codon mutation at a position corresponding to position 2057 of SEQ ID NO: 10, and the HIOL109 allele, encoding a FAD2 protein which is truncated after the amino acid at a position corresponding to position 189 of SEQ ID NO: 3, and lacks the third Histidine box, part of the third, and the complete fourth and fifth TM domain, and the ER retrieval motif.

Knockout fad2 alleles can thus be full knock-out fad2 alleles which encode a FAD2 protein of which at least one of the conserved Histidine boxes is completely or partially deleted, such as a fad2 allele encoding a truncated FAD2 protein of which at least the third Histidine box is deleted. Examples of such a fad2 allele is a fad2 allele containing a stop codon mutation upstream of the codon encoding the first amino acid of the third Histidine box (i.e. the amino acid corresponding to amino acid 315 of SEQ ID NO: 3, or to amino acid 316 of SEQ ID NO: 6, 9 or 15), such as a fad2 allele containing a stop codon mutation upstream of the codon at a position corresponding to position 2992 of SEQ ID NO: 4, or to position 3866 of SEQ ID NO: 7, or to position 2704 of SEQ ID NO: 13. Full knockout fad2 alleles can also be fad2 alleles which encode a FAD2 protein in which at least one amino acid in at least one of the conserved Histidine boxes is substituted with another amino acid, such as fad2 alleles encoding FAD2 proteins of which one or more of the amino acids at a position corresponding to position 105, 106, 107, 108, 109, 141, 142, 143, 144, 145, 315, 316, 317, 318 or 319 of SEQ ID NO: 3, or corresponding to position 105, 106, 107, 108, 109, 141, 142, 143, 144, 145, 316, 317, 318, 319 or 320 of SEQ ID NO: 6, 9, 15, 18 or 24, is substituted, preferably substituted with a non-conservative amino acid.

Full knockout fad2 alleles can also be alleles which do not produce FAD2 protein, such as fad2 alleles with deletions or mutations in the promoter region produce no FAD2 mRNA and no FAD2 protein, or alleles of which (part of) the FAD2 coding sequence is deleted.

The knock-out FAD2 genes may, thus, comprise one or more mutations, such as:

(a) a "missense mutation", which is a change in the nucleic acid sequence that results in the substitution of an amino acid for another amino acid;
(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;
(c) an "insertion mutation" of one or more amino acids, due to one or more codons having been added in the coding sequence of the nucleic acid;
(d) a "deletion mutation" of one or more amino acids, due to one or more codons having been deleted in the coding sequence of the nucleic acid;
(e) a "frameshift mutation", resulting in the nucleic acid sequence being translated in a different frame downstream of the mutation. A frameshift mutation can have various causes, such as the insertion, deletion or duplication of one or more nucleotides;
(f) a splice site mutation, resulting in altered splicing, which results in an altered mRNA processing and may, consequently, in an altered encoded protein or the production of no protein.

Thus in one embodiment, nucleic acid sequences comprising one or more of any of the types of mutations described above are provided. In another embodiment, fad2 sequences comprising one or more stop codon (nonsense) mutations, one or more missense mutations, one or more frameshift mutations, and/or one or more splice site mutations are provided. Any of the above mutant nucleic acid sequences are provided per se (in isolated form), as are plants and plant parts comprising such sequences endogenously. In the tables herein below fad2 alleles are described comprising one or more mutations.

A nonsense mutation in a FAD2 allele, as used herein, is a mutation in a FAD2 allele whereby one or more translation stop codons are introduced into the coding DNA and the corresponding mRNA sequence of the corresponding wild type FAD2 allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a knockout FAD2 allele is provided comprising a nonsense mutation wherein an in-frame stop codon is introduced in the FAD2 codon sequence by a single nucleotide substitution, such as the mutation of CAG to TAG, TGG to TAG, TGG to TGA, or CAA to TAA. In another embodiment, a knockout FAD2 allele is provided comprising a nonsense mutation wherein an in-frame stop codon is introduced in the FAD2 codon sequence by double nucleotide substitutions, such as the mutation of CAG to TAA, TGG to TAA, or CGG to TAG or TGA. In yet another embodiment, a knockout FAD2 allele is provided comprising a nonsense mutation wherein an in-frame stop codon is introduced in the FAD2 codon sequence by triple nucleotide substitutions, such as the mutation of CGG to TAA. The truncated protein lacks the amino acids encoded by the coding DNA downstream of the mutation (i.e. the C-terminal part of the FAD2 protein) and maintains the amino acids encoded by the coding DNA upstream of the mutation (i.e. the N-terminal part of the FAD2 protein).

A range of possible EMS stop codon mutations in the BnFAD2-A1, BnFAD2-C1, BnFAD2-C2, BoFAD2-1, and BrFAD2-genes are shown in Tables 1a-e, respectively.

TABLE 1a possible stop codon mutations in BnFAD2-A1

| position relative to genomic sequence (SEQ ID NO: 4) | WT codon | AA | position releative to protein sequence (SEQ ID NO: 3) | stop codon |
|---|---|---|---|---|
| 2068-2070 | CAA | Gln | 8 | TAA |
| 2218-2220 | TGG | Trp | 58 | TAG, TGA, TAA |
| 2302-2304 | TGG | Trp | 86 | TAG, TGA, TAA |

TABLE 1a-continued possible stop codon mutations in BnFAD2-A1

| position relative to genomic sequence (SEQ ID NO: 4) | WT codon | AA | position relative to protein sequence (SEQ ID NO: 3) | stop codon |
|---|---|---|---|---|
| 2314-2316 | TGG | Trp | 90 | TAG, TGA, TAA |
| 2323-2325 | CAG | Gln | 93 | TAG, TAA |
| 2347-2349 | TGG | Trp | 101 | TAG, TGA, TAA |
| 2392-2394 | CAG | Gln | 116 | TAG, TAA |
| 2395-2397 | TGG | Trp | 117 | TAG, TGA, TAA |
| 2455-2457 | TGG | Trp | 137 | TAG, TGA, TAA |
| 2470-2472 | CGA | Arg | 142 | TGA, TAA |
| 2545-2547 | TGG | Trp | 167 | TAG, TGA, TAA |
| 2599-2601 | CAG | Gln | 185 | TAG, TAA |
| 2614-2616 | TGG | Trp | 190 | TAG, TGA, TAA |
| 2719-2721 | CAG | Gln | 225 | TAG, TAA |
| 2785-2787 | CAA | Gln | 247 | TAA |
| 2866-2868 | CAG | Gln | 274 | TAG, TAA |
| 2908-2910 | TGG | Trp | 288 | TAG, TGA, TAA |
| 2914-2916 | TGG | Trp | 290 | TAG, TGA, TAA |
| 3082-3084 | CAG | Gln | 346 | TAG, TAA |
| 3115-3117 | TGG | Trp | 357 | TAG, TGA, TAA |
| 3157-3159 | CAA | Gln | 371 | TAA |
| 3181-3183 | TGG | Trp | 379 | TAG, TGA, TAA |

40

TABLE 1b possible stop codon mutations in BnFAD2-C1

| position relative to genomic sequence (SEQ ID NO: 7) | WT codon | AA | position relative to protein sequence (SEQ ID NO: 9) | stop codon |
|---|---|---|---|---|
| 2942-2944 | CAA | Gln | 8 | TAA |
| 3092-3094 | TGG | Trp | 58 | TAG, TGA, TAA |
| 3176-3178 | TGG | Trp | 86 | TAG, TGA, TAA |
| 3188-3190 | TGG | Trp | 90 | TAG, TGA, TAA |
| 3197-3199 | CAA | Gln | 93 | TAA |
| 3221-3223 | TGG | Trp | 101 | TAG, TGA, TAA |
| 3266-3268 | CAG | Gln | 116 | TAG, TAA |
| 3269-3271 | TGG | Trp | 117 | TAG, TGA, TAA |
| 3329-3331 | TGG | Trp | 137 | TAG, TGA, TAA |
| 3344-3346 | CGA | Arg | 142 | TGA, TAA |
| 3419-3421 | TGG | Trp | 167 | TAG, TGA, TAA |

TABLE 1b-continued possible stop codon mutations in BnFAD2-C1

| position relative to genomic sequence (SEQ ID NO: 7) | WT codon | AA | position relative to protein sequence (SEQ ID NO: 9) | stop codon |
|---|---|---|---|---|
| 3473-3475 | CAG | Gln | 185 | TAG, TAA |
| 3488-3490 | TGG | Trp | 190 | TAG, TGA, TAA |
| 3593-3595 | CAG | Gln | 225 | TAG, TAA |
| 3659-3661 | CAG | Gln | 247 | TAG, TAA |
| 3740-3742 | CAG | Gln | 274 | TAG, TAA |
| 3782-3784 | TGG | Trp | 288 | TAG, TGA, TAA |
| 3788-3790 | TGG | Trp | 290 | TAG, TGA, TAA |
| 3956-3958 | CAG | Gln | 346 | TAG, TAA |
| 3989-3991 | TGG | Trp | 357 | TAG, TGA, TAA |
| 4031-4033 | CAA | Gln | 371 | TAA |
| 4055-4057 | TGG | Trp | 379 | TAG, TGA, TAA |

TABLE 1c possible stop codon mutations in BnFAD2-C2

| position relative to genomic sequence (SEQ ID NO: 13) | WT codon | AA | position relative to protein sequence (SEQ ID NO: 15) | stop codon |
|---|---|---|---|---|
| 1780-1782 | CAA | Gln | 8 | TAA |
| 2014-2016 | TGG | Trp | 86 | TAG, TGA, TAA |
| 2026-2028 | TGG | Trp | 90 | TAG, TGA, TAA |
| 2035-2037 | CAA | Gln | 93 | TAA |
| 2059-2061 | TGG | Trp | 101 | TAG, TGA, TAA |
| 2104-2106 | CAG | Gln | 116 | TAG, TAA |
| 2107-2109 | TGG | Trp | 117 | TAG, TGA, TAA |
| 2167-2169 | TGG | Trp | 137 | TAG, TGA, TAA |
| 2182-2184 | CGA | Arg | 142 | TGA, TAA |
| 2257-2259 | TGG | Trp | 167 | TAG, TGA, TAA |
| 2311-2313 | CAG | Gln | 185 | TAG, TAA |
| 2326-2328 | TGG | Trp | 190 | TAG, TGA, TAA |
| 2431-2433 | CAG | Gln | 225 | TAG, TAA |
| 2497-2499 | CGA | Arg | 247 | TGA, TAA |
| 2578-2580 | CAG | Gln | 274 | TAG, TAA |
| 2620-2622 | TGG | Trp | 288 | TAG, TGA, TAA |
| 2626-2628 | TGG | Trp | 290 | TAG, TGA, TAA |
| 2794-2796 | CAG | Gln | 346 | TAG, TAA |
| 2827-2829 | TGG | Trp | 357 | TAG, TGA, TAA |

TABLE 1c-continued possible stop codon mutations in BnFAD2-C2

| position relative to genomic sequence (SEQ ID NO: 13) | WT codon | AA | position relative to protein sequence (SEQ ID NO: 15) | stop codon |
|---|---|---|---|---|
| 2869-2871 | CAA | Gln | 371 | TAA |
| 2893-2895 | TGG | Trp | 379 | TAG, TGA, TAA |

TABLE 1d possible stop codon mutations in BrFAD2-1

| position relative to genomic sequence (SEQ ID NO: 16) | WT codon | AA | position relative to protein sequence (SEQ ID NO: 18) | stop codon |
|---|---|---|---|---|
| 2029-2031 | CAA | Gln | 8 | TAA |
| 2179-2181 | TGG | Trp | 58 | TAG, TGA, TAA |
| 2263-2265 | TGG | Trp | 86 | TAG, TGA, TAA |
| 2275-2277 | TGG | Trp | 90 | TAG, TGA, TAA |
| 2284-2286 | CAG | Gln | 93 | TAG, TAA |
| 2308-2310 | TGG | Trp | 101 | TAG, TGA, TAA |
| 2353-2355 | CAG | Gln | 116 | TAG, TAA |
| 2356-2358 | TGG | Trp | 117 | TAG, TGA, TAA |
| 2416-2418 | TGG | Trp | 137 | TAG, TGA, TAA |
| 2431-2433 | CGA | Arg | 142 | TGA, TAA |
| 2506-2508 | TGG | Trp | 167 | TAG, TGA, TAA |
| 2560-2562 | CAG | Gln | 185 | TAG, TAA |
| 2575-2577 | TGG | Trp | 190 | TAG, TGA, TAA |
| 2680-2682 | CAG | Gln | 225 | TAG, TAA |
| 2746-2748 | CAA | Gln | 247 | TAA |
| 2827-2829 | CAG | Gln | 274 | TAG, TAA |
| 2869-2871 | TGG | Trp | 288 | TAG, TGA, TAA |
| 2875-2877 | TGG | Trp | 290 | TAG, TGA, TAA |
| 3043-3045 | CAG | Gln | 346 | TAG, TAA |
| 3076-3078 | TGG | Trp | 357 | TAG, TGA, TAA |
| 3118-3120 | CAA | Gln | 371 | TAA |
| 3142-3144 | TGG | Trp | 379 | TAG, TGA, TAA |

TABLE 1e possible stop codon mutations in BoFAD2-1

| position relative to genomic sequence (SEQ ID NO: 22) | WT codon | AA | position relative to protein sequence (SEQ ID NO: 24) | stop codon |
|---|---|---|---|---|
| 2913-2915 | CAA | Gln | 8 | TAA |
| 3063-3065 | TGG | Trp | 58 | TAG, TGA, TAA |
| 3147-3149 | TGG | Trp | 86 | TAG, TGA, TAA |
| 3159-3161 | TGG | Trp | 90 | TAG, TGA, TAA |
| 3168-3170 | CAA | Gln | 93 | TAA |
| 3192-3194 | TGG | Trp | 101 | TAG, TGA, TAA |
| 3237-3239 | CAG | Gln | 116 | TAG, TAA |
| 3240-3242 | TGG | Trp | 117 | TAG, TGA, TAA |
| 3300-3302 | TGG | Trp | 137 | TAG, TGA, TAA |
| 3315-3317 | CGA | Arg | 142 | TGA, TAA |
| 3390-3392 | TGG | Trp | 167 | TAG, TGA, TAA |
| 3444-3446 | CAG | Gln | 185 | TAG, TAA |
| 3459-3461 | TGG | Trp | 190 | TAG, TGA, TAA |
| 3564-3566 | CAG | Gln | 225 | TAG, TAA |
| 3630-3632 | CAG | Gln | 247 | TAG, TAA |
| 3711-3713 | CAG | Gln | 274 | TAG, TAA |
| 3753-3755 | TGG | Trp | 288 | TAG, TGA, TAA |
| 3759-3761 | TGG | Trp | 290 | TAG, TGA, TAA |
| 3927-3929 | CAG | Gln | 346 | TAG, TAA |
| 3960-3962 | TGG | Trp | 357 | TAG, TGA, TAA |
| 4002-4004 | CAA | Gln | 371 | TAA |
| 4026-4028 | TGG | Trp | 379 | TAG, TGA, TAA |

Obviously, mutations are not limited to the ones shown in the above tables and it is understood that analogous STOP mutations may be present in fad2 alleles other than those depicted in the sequence listing and referred to in the tables above.

Not only stop codon mutations, but also mutations resulting in an amino acid substitution may lead to proteins with reduced functionality or with no detectable activity.

A missense mutation in an FAD2 allele, as used herein, is any mutation (deletion, insertion or substitution) in a FAD2 allele whereby one or more codons are changed into the coding DNA and the corresponding mRNA sequence of the corresponding wild type FAD2 allele, resulting in the substitution of one or more amino acids in the wild type FAD2 protein for one or more other amino acids in the mutant FAD2 protein. In one embodiment, a full knockout mutant FAD2 allele is provided comprising a missense mutation resulting in a substitution of a Histidine (His) residue at position 109 of the FAD2 protein in SEQ ID NO: 6, or a sequence essentially similar thereto, in particular by a tyrosine (Tyr) residue, such as the HIOL101 allele (Table 2a).

In another embodiment, said knock-out fad2 gene in Brassica napus is selected from the group consisting of nucleic acids comprising:
a C to T mutation at position 2371 of SEQ ID No. 4;
a G to A mutation at position 3223 of SEQ ID No. 7;
a C to T mutation at position 2057 of SEQ ID No. 10;
a G to A mutation at position 2327 of SEQ ID No. 13

Wild-type and mutant FAD2 nucleic acid sequences from the A-genome as described herein, such as BnFAD2-A1, BnFAD2-A2, BrFAD2-1, and BrFAD2-2 are also suitable to use in other Brassica species comprising an A genome, such as Brassica juncea.

Wild-type and mutant FAD2 nucleic acid sequences from the C-genome as described herein, such as BnFAD2-C1, BnFAD2-C2, BoFAD2-1, and BoFAD2-2 are also suitable to use in other Brassica species comprising a C genome, such as Brassica carinata.

Amino Acid Sequences According to the Invention

Provided are both wild type FAD2 amino acid sequences and mutant FAD2 amino acid sequences (comprising one or more mutations, preferably mutations which result in a significantly reduced or no biological activity of the FAD2 protein) from Brassicaceae, particularly from *Brassica* species, especially from *Brassica napus, Brassica rapa*, and *Brassica oleracea*. In addition, mutagenesis methods can be used to generate mutations in wild type FAD2 alleles, thereby generating mutant alleles which can encode further mutant FAD2 proteins. In one embodiment the wild type and/or mutant FAD2 amino acid sequences are provided within a *Brassica* plant (i.e. endogenously). However, isolated FAD2 amino acid sequences (e.g. isolated from the plant or made synthetically), as well as variants thereof and fragments of any of these are also provided herein.

Amino acid sequences of FAD2-A1, FAD2-C1, FAD2-A1 and FAD2-C2 proteins from *Brassica napus*, FAD2-1 and FAD2-2 proteins from *Brassica rapa*, and FAD2-1 and FAD2-2 proteins from *Brassica oleracea*, have been isolated as depicted in the sequence listing. The wild type FAD2 sequences are depicted, while the mutant FAD2 sequences of these sequences, and of sequences essentially similar to these, are described herein below, with reference to the wild type FAD2 sequences.

"*Brassica napus* FAD-A1 amino acid sequences" or "BnFAD2-A1 amino acid sequences" or variant amino acid sequences thereof according to the invention are amino acid sequences having at least 95%, 98%, 99% or 100% sequence identity with SEQ ID NO: 6. These amino acid sequences may also be referred to as being "essentially similar" or "essentially identical" to the FAD2 sequences provided in the sequence listing.

"*Brassica napus* FAD2-C1 amino acid sequences" or "BnFAD2-C1 amino acid sequences" or variant amino acid sequences thereof according to the invention are amino acid sequences having at least 95%, 98%, 99% or 100% sequence identity with SEQ ID NO: 9. These amino acid sequences may also be referred to as being "essentially similar" or "essentially identical" to the FAD2 sequences provided in the sequence listing.

"*Brassica napus* FAD2-A2 amino acid sequences" or "BnFAD2-A2 amino acid sequences" or variant amino acid sequences thereof according to the invention are amino acid sequences having at least 95%, 98%, 99% or 100% sequence identity with SEQ ID NO: 12. These amino acid sequences may also be referred to as being "essentially similar" or "essentially identical" to the FAD2 sequences provided in the sequence listing.

"*Brassica napus* FAD2-C2 amino acid sequences" or "BnFAD2-C2 amino acid sequences" or variant amino acid sequences thereof according to the invention are amino acid sequences having at least 95%, 98%, 99% or 100% sequence identity with SEQ ID NO: 15. These amino acid sequences may also be referred to as being "essentially similar" or "essentially identical" to the FAD2 sequences provided in the sequence listing.

"*Brassica rapa* FAD2-1 amino acid sequences" or "BrFAD2-1 amino acid sequences" or variant amino acid sequences thereof according to the invention are amino acid sequences having at least 95%, 98%, 99% or 100% sequence identity with SEQ ID NO: 18. These amino acid sequences may also be referred to as being "essentially similar" or "essentially identical" to the FAD2 sequences provided in the sequence listing.

"*Brassica rapa* FAD2-2 amino acid sequences" or "BrFAD2-2 amino acid sequences" or variant amino acid sequences thereof according to the invention are amino acid sequences having at least 95%, 98%, 99% or 100% sequence identity with SEQ ID NO: 21. These amino acid sequences may also be referred to as being "essentially similar" or "essentially identical" to the FAD2 sequences provided in the sequence listing.

"*Brassica oleracea* FAD2-1 amino acid sequences" or "BoFAD2-1 amino acid sequences" or variant amino acid sequences thereof according to the invention are amino acid sequences having at least 95%, 98%, 99% or 100% sequence identity with SEQ ID NO: 24. These amino acid sequences may also be referred to as being "essentially similar" or "essentially identical" to the FAD2 sequences provided in the sequence listing.

"*Brassica oleracea* FAD2-2 amino acid sequences" or "BoFAD2-2 amino acid sequences" or variant amino acid sequences thereof according to the invention are amino acid sequences having at least 95%, 98%, 99% or 100% sequence identity with SEQ ID NO: 27. These amino acid sequences may also be referred to as being "essentially similar" or "essentially identical" to the FAD2 sequences provided in the sequence listing.

A "FAD2-A1 protein" can be a BnFAD2-A1 protein, or can be a BrFAD2-1 protein.

A "FAD2-C1 protein" can be a BnFAD2-C1 protein, or can be a BoFAD2-1 protein.

A "FAD2-A2 protein" can be a BnFAD2-A2 protein, or can be a BrFAD2-2 protein.

A "FAD2-C2 protein" can be a BnFAD2-C2 protein, or can be a BoFAD2-2 protein.

Thus, the invention provides both amino acid sequences of wild type proteins, including variants and fragments thereof (as defined further below), as well as mutant amino acid sequences of any of these, whereby the mutation in the amino acid sequence preferably results in a significant reduction in or a complete abolishment of the biological activity of the FAD2 protein as compared to the biological activity of the corresponding wild type FAD2 protein.

Both endogenous and isolated amino acid sequences are provided herein. Also provided are fragments of the FAD2 amino acid sequences and FAD2 variant amino acid sequences defined above. A "fragment" of a FAD2 amino acid sequence or variant thereof (as defined) may be of various lengths, such as at least 10, 12, 15, 18, 20, 50, 100, 150, 175, 180 contiguous amino acids of the FAD2 sequence (or of the variant sequence).

Amino Acid Sequences of Wild-Type FAD2 Proteins

The amino acid sequences depicted in the sequence listing are wild type FAD2 proteins from *Brassica napus*. Thus, these sequences are endogenous to the *Brassica napus* plants from which they were isolated. Other *Brassica*, varieties, breeding lines or wild accessions may be screened for other functional FAD2 proteins with the same amino acid sequences or variants thereof, as described above.

In addition, it is understood that FAD2 amino acid sequences and variants thereof (or fragments of any of these) may be identified in silico, by screening amino acid databases for essentially similar sequences. Fragments of amino acid molecules according to the invention are also provided.

Wild-type FAD2 amino acid sequences may encompass amino acid sequences of non-functional FAD2 proteins, such as BnFAD2-A2 and BrFAD2-2 amino acid sequence of SEQ ID NO: 12 and 21, respectively, as described herein, are truncated proteins of 136 amino acids which lack the five TM domains, the three Histidine boxes, and the ER retrieval motif (see FIG. 1), and such as the BoFAD2-2 amino acid sequence of SEQ ID NO: 27 as described herein, which is a truncated protein of 290 amino acids which lacks third Histidine box and the ER retrieval motif (see FIG. 1).

Amino Acid Sequences of Mutant FAD2 Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the FAD2 protein relative to the wild type protein. As described above, basically, any mutation which results in a protein comprising at least one amino acid insertion, deletion and/or substitution relative to the wild type protein can lead to significantly reduced or no biological activity.

Thus in one embodiment, mutant FAD2 proteins are provided comprising one or more deletion or insertion mutations, whereby the deletion(s) or insertion(s) result(s) in a mutant protein which has significantly reduced or no activity. Such mutant FAD2 proteins are FAD2 proteins wherein at least 1, at least 2, at least 3, at least 4, at least 5, at least 10, at least 20, at least 30, at least 50, at least 100, at least 150, at least 200, at least 250, or more amino acids are deleted, inserted or substituted as compared to the wild type FAD2 protein, whereby the deletion(s) or insertion(s) result(s) in a mutant protein which has significantly reduced or no activity.

In another embodiment, mutant FAD2 proteins are provided which are truncated whereby the truncation results in a mutant protein that has significantly reduced or no activity. Truncated FAD2 proteins with significantly reduced or no activity may be truncated FAD2 proteins lacking at least the third Histidine box, such as FAD2 proteins truncated at a position corresponding to position 315 of SEQ ID NO: 3, or at a position corresponding to position 316 of SEQ ID NO: 6, 9, 15, 18, or 24, or at any position upstream of a position corresponding to position 315 of SEQ ID NO: 3, or at a position corresponding to position 316 of SEQ ID NO: 6, 9, 15, 18, or 24.

In yet another embodiment, mutant FAD2 proteins are provided comprising one or more substitution mutations, whereby the substitution(s) result(s) in a mutant protein that has significantly reduced or no activity. FAD2 proteins with one or more substitution mutations with significantly reduced or no activity may be FAD2 proteins in which at least one amino acid in at least one of the conserved Histidine boxes is substituted with another amino acid, such as fad2 alleles encoding FAD2 proteins of which one or more of the amino acids at a position corresponding to position 105, 106, 107, 108, 109, 141, 142, 143, 144, 145, 315, 316, 317, 318 or 319 of SEQ ID NO: 3, or corresponding to position 105, 106, 107, 108, 109, 141, 142, 143, 144, 145, 316, 317, 318, 319 or 320 of SEQ ID NO: 6, 9, 15, 18 or 24, is substituted, preferably substituted with a non-conservative amino acid.

Examples of conservative amino acid substitutions are:

| Residue | Conservative Substitutions | Residue | Conservative Substitutions |
|---|---|---|---|
| Ala | Ser | Leu | Ile, Val |
| Arg | Lys | Lys | Arg, Gln |
| Asn | Gln, His | Met | Leu, Ile |
| Asp | Glu | Phe | Met, Leu, Tyr |
| Gln | Asn | Ser | Thr, Gly |

-continued

| Residue | Conservative Substitutions | Residue | Conservative Substitutions |
|---|---|---|---|
| Cys | Ser | Thr | Ser, Val |
| Glu | Asp | Trp | Tyr |
| Gly | Pro | Tyr | Trp, Phe |
| His | Asn, Gln | Val | Ile, Leu |
| Ile | Leu, Val | | |

Non-conservative amino acids are thus amino acids other than the conservative amino acids.

In a further embodiment, said mutant FAD2 proteins from *Brassica napus* are selected from the group consisting of proteins comprising:
- a H to Y substitution at position 109 of SEQ ID No. 6;
- SEQ ID No. 9 truncated after the amino acid at position 100;
- SEQ ID No. 15 truncated after the amino acid at position 189.

FAD3 Sequences

Nucleic acid and amino acid sequences of FAD3-A1, FAD3-A2, FAD3-A3, FAD3-C1, and FAD3-C2 have been described in WO2011/060946 (incorporated herein by reference).

"FAD3-A1 nucleic acid sequences" or "FAD3-A1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 38 or nucleic acid sequences having at least 80%, at least 85%, at least 90%, at least 95%, 96%, 97%, 98%, 99% or 100% sequence identity with SEQ ID NO: 37 or SEQ ID NO: 39. These nucleic acid sequences may also be referred to as being "essentially similar" or "essentially identical" to the FAD3 sequences provided in the sequence listing.

"FAD3-A2 nucleic acid sequences" or "FAD3-A2 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 41 or nucleic acid sequences having at least 80%, at least 85%, at least 90%, at least 95%, 96%, 97%, 98%, 99% or 100% sequence identity with SEQ ID NO: 40 or SEQ ID NO: 42. These nucleic acid sequences may also be referred to as being "essentially similar" or "essentially identical" to the FAD3 sequences provided in the sequence listing.

"FAD3-A3 nucleic acid sequences" or "FAD3-A3 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 44 or nucleic acid sequences having at least 80%, at least 85%, at least 90%, at least 95%, 96%, 97%, 98%, 99% or 100% sequence identity with SEQ ID NO: 43 or SEQ ID NO: 45. These nucleic acid sequences may also be referred to as being "essentially similar" or "essentially identical" to the FAD3 sequences provided in the sequence listing.

"FAD3-C1 nucleic acid sequences" or "FAD3-C1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 47 or nucleic acid sequences having at least 80%, at least 85%, at least 90%, at least 95%, 96%, 97%, 98%, 99% or 100% sequence identity with SEQ ID NO: 46 or SEQ ID NO: 48 These nucleic acid sequences may also be referred to as being "essentially similar" or "essentially identical" to the FAD3 sequences provided in the sequence listing.

"FAD3-C2 nucleic acid sequences" or "FAD3-C2 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 50 or nucleic acid sequences having at least 80%, at least 85%, at least 90%, at least 95%, 96%, 97%, 98%, 99% or 100% sequence identity with SEQ ID NO: 49 or SEQ ID NO: 51. These nucleic acid sequences may also be referred to as being "essentially similar" or "essentially identical" to the FAD3 sequences provided in the sequence listing.

"FAD3-A1 amino acid sequences" or "FAD3-A1 variant amino acid sequences" according to the invention are amino acid sequences having at least 75%, at least 80%, at least 85%, at least 90%, at least 95%, 98%, 99% or 100% sequence identity with SEQ ID NO: 38. These amino acid sequences may also be referred to as being "essentially similar" or "essentially identical" to the FAD3 sequences provided in the sequence listing.

"FAD3-A2 amino acid sequences" or "FAD3-A2 variant amino acid sequences" according to the invention are amino acid sequences having at least 75%, at least 80%, at least 85%, at least 90%, at least 95%, 98%, 99% or 100% sequence identity with SEQ ID NO: 41. These amino acid sequences may also be referred to as being "essentially similar" or "essentially identical" to the FAD3 sequences provided in the sequence listing.

"FAD3-A3 amino acid sequences" or "FAD3-A3 variant amino acid sequences" according to the invention are amino acid sequences having at least 75%, at least 80%, at least 85%, at least 90%, at least 95%, 98%, 99% or 100% sequence identity with SEQ ID NO: 44. These amino acid sequences may also be referred to as being "essentially similar" or "essentially identical" to the FAD3 sequences provided in the sequence listing.

"FAD3-C1 amino acid sequences" or "FAD3-C1 variant amino acid sequences" according to the invention are amino acid sequences having at least 75%, at least 80%, at least 85%, at least 90%, at least 95%, 98%, 99% or 100% sequence identity with SEQ ID NO: 47. These amino acid sequences may also be referred to as being "essentially similar" or "essentially identical" to the FAD3 sequences provided in the sequence listing.

"FAD3-C2 amino acid sequences" or "FAD3-C2 variant amino acid sequences" according to the invention are amino acid sequences having at least 75%, at least 80%, at least 85%, at least 90%, at least 95%, 98%, 99% or 100% sequence identity with SEQ ID NO: 50. These amino acid sequences may also be referred to as being "essentially similar" or "essentially identical" to the FAD3 sequences provided in the sequence listing.

As used herein, a "knock-out fad3 allele" is a mutant allele directing a significantly reduced or no functional FAD3 expression, i.e. a significantly reduced amount of functional FAD3 protein or no functional FAD3 protein, in the cell in vivo.

Examples of knock-out fad3 alleles are described in WO2011/060946 (incorporated herein by reference), and encompass, for example, a knock-out fad2 allele comprising a G to A substitution at a position corresponding to position 2405 of SEQ ID NO: 37; a G to A substitution at a position corresponding to position 3934 of SEQ ID NO: 40; a G to A substitution at a position corresponding to position 2847 of SEQ ID NO: 43; a G to A substitution at a position corresponding to position 2702 of SEQ ID NO: 46; or a G to A substitution at a position corresponding to position 3909 of SEQ ID NO: 49.

In a further aspect, the *Brassica napus* plant, or a cell, part, seed or progeny thereof according to the invention has increased levels of C18:1 in the seed oil, such as a level of C18:1 in the seed oil of between about 73% to about 75%, and which maintains normal agronomic development. In another aspect, the *Brassica napus* plant or a cell, part, seed or progeny thereof, according to the invention, which comprises mutant fad2 alleles and mutant fad3 alleles, has increased levels of C18:1 and decreased levels of C18:3 in the seed oil. Also provided is oil from the seeds according to the invention.

Another aspect of the invention provides a method for increasing the levels of C18:1 in seed oil while maintaining normal agronomic development, said method comprising introducing a knock-out fad2 allele of a FAD2-A1 gene and a knock-out fad2 allele of a FAD2-C2 gene into a *Brassica napus* plant, and selecting a *Brassica napus* plant comprising said knock-out fad2 allele of said FAD2-A1 gene, and said knock-out fad2 allele of said FAD2-C2 gene, which further contains a FAD2-C1 gene of which the fad2 alleles encode a functional FAD2 protein. In a further embodiment, the *Brassica* plant produced by said method comprises knock-out fad2 alleles of the FAD2-A2 gene.

Another aspect of the invention provides a method for increasing the levels of C18:1 and decreasing the levels of C18:3 in seed oil while maintaining normal agronomic development, said method comprising introducing a knock-out fad2 allele of a FAD2-A1 gene and a knock-out fad2 allele of a FAD2-C2 gene, and a knock-out fad3 allele of a FAD3-A1 gene, a knock-out fad3 allele of a FAD3-A2 gene, a knock-out fad3 allele of a FAD3-A3 gene, a knock-out fad3 allele of a FAD3-C1 gene, and a knock-out fad3 allele of a FAD3-C2 gene, into a *Brassica napus* plant, and selecting a *Brassica napus* plant comprising said knock-out fad2 allele of said FAD2-A1 gene, and said knock-out fad2 allele of said FAD2-C2 gene, said knock-out fad3 allele of said FAD3-A1 gene, said knock-out fad3 allele of said FAD3-A2 gene, said knock-out fad3 allele of said FAD3-A3 gene, said knock-out fad3 allele of said FAD3-C1 gene, and said knock-out fad3 allele of said FAD3-C2 gene, which further contains a FAD2-C1 gene of which the fad2 alleles encode a functional FAD2 protein, and a FAD2 A2 gene of which the fad2 alleles are knock-out fad2 alleles.

In yet another embodiment, the method according to the invention comprises the step of selecting said *Brassica napus* plant comprising said knock-out fad2 allele of said FAD2-A1 gene and said knock-out fad2 allele of said FAD2-C2 gene by analyzing genomic DNA from said plant for the presence of at least one molecular marker, wherein at least one molecular marker is linked to said knock-out fad2 allele of said FAD2-A1 gene and wherein at least one molecular marker is linked to said knock-out fad2 allele of said FAD2-C2 gene and, optionally, wherein at least one molecular marker is linked to one or more fad2 alleles of said FAD2 A2 gene or of said FAD2-C1 gene, or to one or more fad3 alleles of said FAD3-A1 gene, said FAD5 A2 gene, said FAD3-A3 gene, said FAD3-C1 gene, or said FAD3-C2 gene.

"C18:1", also referred to as "oleic acid", "cis-9-octadecenoic", "18:1", "18:1 (n-9)", "9c-18:1" or "18:1cis $\Delta^9$" as used herein, refers to a monounsaturated omega-9 fatty acid, with the IUPAC name (9Z)-Octadec-9-enoic acid.

Increasing the C18:1 levels or increased C18:1 levels in seed oil can be an increase of C18:1 levels with at least 2%, or at least 5%, or at least 8%, or at least 10%, or at least 12%. Said increase is an increase with respect to C18:1 levels as obtained in control plants.

C18:1 levels of of between about 73% to about 75% can, for example, be C18:1 levels of between 70 and 78%, or between 71 and 77%, or between 72 and 76%, or between 73 and 75%.

"C18:3", also referred to as "lonilenic acid" or alpha-linolenic acid".

As used herein, "a decreased level of C18:3" refers to a significant reduction in the amount of total alpha-linolenic acid (C18:3) present in the seed oil of a plant as compared to a control plant. The C18:3 seed oil content of said plants comprising decreased level of C18:3 is reduced to below 11% wt, 10% wt, 9% wt, 8% wt, 7.0 wt %, 6.0 wt %, 5.0 wt %, 4.0 wt %, 3.0 wt %, 2.5 wt %, 2.0 wt %, 1.5% wt, 1.0 wt %, 0.5 wt of the total seed oil content.

C18:1 and C18:3 levels in the seed oil can be measured as described herein, such as, for example, using the methods as described in Examples 4 and 5.

The "control plant" as used herein is generally a plant of the same species which has wild-type levels of FAD2 and/or FAD3. "Wild-type levels of FAD2" as used herein refers to the typical levels of FAD2 protein in a plant as it most commonly occurs in nature, of which the FAD2 genes are wild-type FAD2 genes. "Wild-type levels of FAD3" as used herein refers to the typical levels of FAD3 protein in a plant as it most commonly occurs in nature, of which the FAD3 genes are wild-type FAD3 genes.

"Maintaining normal agronomic development" as used herein refers to having agronomic parameters which are not significantly different from a control plant. "Maintaining normal agronomic development" can, for example, be maintaining yield, or having a yield which is not significantly different from a control plant. Maintaining normal agronomic development can also be having a vigor score which is not significantly different from a control plant. "Maintaining normal agronomic development" can also be having a score for establishment, vigor, flowering start, flowering end, plant height, maturity, or protein content, or any combination thereof, which is not significantly different from a control plant. Agronomic parameters can be determined, for example, as described herein in Examples 5 and 6.

A method to introduce a knock-out fad2 allele, may comprise the steps of treating seeds or plant material with a mutagenic chemical substance or with ionizing radiation; identifying plants with a mutated fad2 gene, wherein the FAD2 gene, prior to being mutated, encodes a polypeptide having at least 90% sequence identity to SEQ ID No. 6, to SEQ ID No. 9, to SEQ ID No. 15, SEQ ID NO: 18 or to SEQ ID No. 24; and selecting a plant with an increased level of C18:1 in the seeds compared to a plant in which the FAD2 gene is not mutated.

Said FAD2 gene, prior to being mutated, can be, for example, a FAD2 gene having at least 90% sequence identity, or at least 95% sequence identity, or at least 98% sequence identity or having 100% sequence identity to SEQ ID No. 4, to SEQ ID No. 7, to SEQ ID No. 13, SEQ ID NO: 16 or to SEQ ID No. 22, or can be a FAD2 gene of which the cDNA has at least 90% sequence identity, or at least 95% sequence identity, or at least 98% sequence identity or has 100% sequence identity to SEQ ID No. 5, to SEQ ID No. 8, to SEQ ID No. 14, SEQ ID NO: 17 or to SEQ ID No. 23.

Introducing said knock-out allele of FAD2 can also occur through introduction of a knock-out FAD2 allele from one plant into another, for example by crossing a plant comprising said knock-out FAD2 allele with a plant not comprising said knock-out FAD2 allele and identifying progeny plants comprising said knock-out FAD2 allele, optionally using one or more molecular markers.

Said knock-out fad2 alleles can be introduced into a Brassica napus plant comprising a FAD2-C1 gene of which the FAD2 alleles encode a functional FAD2 protein. Alternatively, both said knock-out fad2 alleles and said FAD2 alleles of said FAD2-C1 gene which encode a functional FAD2 protein can be introduced into a Brassica napus plant.

In a further embodiment, a method is provided to determine the presence or absence of a knock-out fad2 allele in a biological sample, comprising providing genomic DNA from said biological sample, and analyzing said DNA for the presence of at least one molecular marker, wherein the at least one molecular marker is linked to said knock-out fad2 allele.

Said genomic DNA can be provided by isolating genomic DNA from said biological sample. Isolating genomic DNA refers to isolating a biological sample comprising genomic DNA from, such as isolating part of a tissue, such as, for example part of a leaf. Isolating genomic DNA from said biological sample can, but does not need to comprise, purification of genomic DNA from said sample.

Yet another embodiment provides a kit for the detection of a knock-out fad2 allele in Brassica DNA samples, wherein said kit comprises one or more PCR primer pairs, which are able to amplify a DNA marker linked to said knock-out fad2 allele.

Another embodiment provides a method for determining the zygosity status of a knock-out fad2 allele in a plant, or a cell, part, seed or progeny thereof, comprising determining the presence of a knock-out and/or a corresponding wild type FAD2 specific region in the genomic DNA of said plant, or a cell, part, seed or progeny thereof.

Said knock-out FAD2 allele can be transferred from one plant to another plant comprising the steps of: (a) identifying a first plant comprising at least one knock-out fad2 allele, (b) crossing the first plant with a second plant not comprising the at least one knock-out fad2 allele and collecting F1 hybrid seeds from the cross, (c) optionally, identifying F1 plants comprising the at least one knock-out fad2 allele, (d) backcrossing F1 plants comprising the at least one knock-out fad2 allele with the second plant not comprising the at least one knock-out fad2 allele for at least one generation (x) and collecting BCx seeds from the crosses, and (e) identifying in every generation BCx plants comprising the at least one knock-out fad2 allele by analyzing genomic DNA of said BCx plants for the presence of at least one molecular marker, wherein the at least one molecular marker is linked to said knock-out fad2 allele.

A molecular marker which is linked to said knock-out allele of a FAD2 gene or said mutant FAD2 allele can comprise on or more primers or probes that specifically detect said knock-out allele of said FAD2 gene as described herein below.

Methods According to the Invention

Methods are provided for generating and selecting Brassica napus seed plants comprising a FAD2-A1, a FAD2-A2, a FAD2-C1 and a FAD2-C2 gene, and cells, parts, seeds and progeny thereof, having increased levels of C18:1 in the seeds, knock-out fad2 alleles of the FAD2-A1 and of the FAD2-C2 genes, and wherein the fad2 alleles of said FAD2-C1 gene encode a functional FAD2 protein, and to distinguish between the presence of knockout mutant fad2 alleles, and wild type FAD2 alleles in a plant or plant part having increased C18:1 levels in the seeds. Thus methods are provided (such as mutagenesis and/or marker assisted selection) for generating and/or identifying knockout fad2 alleles or seed plants or plant parts comprising such fad2 alleles and for combining a suitable number of knockout fad2 alleles and/or different types of knockout fad2 alleles in a single seed plant to alter the levels of C18:1 in the seeds of the plants while maintaining normal agronomic development.

Mutant fad2 alleles may be generated (for example induced by mutagenesis) and/or identified using a range of methods, which are conventional in the art, for example using nucleic acid amplification based methods to amplify part or all of the fad2 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant FAD2 alleles, using techniques which are conventional in the art, for example nucleic acid amplification based techniques, such as polymerase chain reaction (PCR) based techniques (amplification of the fad2 alleles) or hybridization based techniques, e.g. Southern blot analysis, BAC library screening, and the like, and/or direct sequencing of fad2 alleles. To screen for the presence of point mutations (so called Single Nucleotide Polymorphisms or SNPs) in mutant FAD2 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type FAD2 allele results in the presence of one or more deleted, inserted, or substituted nucleotides (hereinafter called "mutation region") in the resulting mutant FAD2 allele. The mutant FAD2 allele can thus be characterized by the location and the configuration of the one or more deleted, inserted, or substituted nucleotides in the wild type FAD2 allele. The site in the wild type FAD2 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) FAD2 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) FAD2 allele which is located either immediately upstream of and contiguous with (5' flanking region or sequence") or immediately downstream of and contiguous with (3' flanking region or sequence") the mutation region in the mutant FAD2 allele (or in the corresponding wild type FAD2 allele). A "joining region" as used herein refers to a DNA region in the mutant (or the corresponding wild type) FAD2 allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant FAD2 allele or the plant or plant material comprising a specific mutant FAD2 allele, or products which comprise plant material comprising a specific mutant FAD2 allele are based on the specific genomic characteristics of the specific mutant FAD2 allele as compared to the genomic characteristics of the corresponding wild type FAD2 allele, such as, a specific restriction map of the genomic region comprising the mutation region, molecular markers comprising primers and/or probes as described below, or the sequence of the flanking and/or mutation regions.

Once a specific mutant FAD2 allele has been sequenced, molecular markers, such as primers and probes can be developed which specifically recognize a sequence within the 5' flanking, 3' flanking and/or mutation regions of the mutant FAD2 allele in the nucleic acid (DNA or RNA) of a sample by way of a molecular biological technique. For instance an amplification method can be developed to identify the mutant FAD2 allele in biological samples (such as samples of plants, plant material or products comprising plant material). Such an amplification is based on at least two specific "primers": one recognizing a sequence within the 5' or 3' flanking region of the mutant FAD2 allele and the other recognizing a sequence within the 3' or 5' flanking region of the mutant FAD2 allele, respectively; or one recognizing a sequence within the 5' or 3' flanking region of the mutant FAD2 allele and the other recognizing a sequence within the mutation region of the mutant FAD2 allele; or one recognizing a sequence within the 5' or 3' flanking region of the mutant FAD2 allele and the other recognizing a sequence spanning the joining region between the 3' or 5' flanking region and the mutation region of the specific mutant FAD2 allele (as described further below), respectively.

The primers preferably have a sequence of between 15 and 35 nucleotides which under optimized amplification conditions "specifically recognize" a sequence within the 5' or 3' flanking region, a sequence within the mutation region, or a sequence spanning the joining region between the 3' or 5' flanking and mutation regions of the specific mutant FAD2 allele, so that a specific fragment ("mutant FAD2 specific fragment" or discriminating amplicon) is amplified from a nucleic acid sample comprising the specific mutant FAD2 allele. This means that only the targeted mutant FAD2 allele, and no other sequence in the plant genome, is amplified under optimized amplification conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant FAD2 allele or the complement thereof (i.e., for example, the sequence 5' or 3' flanking the one or more nucleotides deleted, inserted or substituted in the mutant FAD2 alleles of the invention, such as the sequence 5' or 3' flanking the non-sense, mis-sense, frameshift or splice site mutations described above or the sequence 5' or 3' flanking the STOP codon mutations indicated in the above Tables or the substitution mutations indicated above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant FAD2 allele or the complement thereof (i.e., for example, the sequence of nucleotides inserted or substituted in the FAD2 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be no longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant FAD2 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense, frameshift or splice site mutations in the FAD2 genes of the invention described above and the sequence of the non-sense, missense, frameshift or splice site mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A↔T; G↔C) and reading the sequence in the 5' to 3' direction, i.e. in opposite direction of the represented nucleotide sequence.

Examples of primers suitable to identify specific mutant FAD2 alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant FAD2 allele, provided the mismatches still allow specific identification of the specific mutant FAD2 allele with these primers under optimized amplification conditions. The range of allowable mismatches however, can easily be determined experimentally and are known to a person skilled in the art.

Detection and/or identification of a "mutant FAD2 specific fragment" can occur in various ways, e.g., via size estimation after gel or capillary electrophoresis or via fluorescence-based detection methods. The mutant FAD2 specific fragments may also be directly sequenced. Other sequence specific methods for detection of amplified DNA fragments are also known in the art.

Standard nucleic acid amplification protocols, such as PCR protocols are described in the art, such as in 'PCR Applications Manual" (Roche Molecular Biochemicals, 2nd Edition, 1999) and other references. The optimal conditions for the amplification, including the sequence of the specific primers, is specified in a "PCR identification protocol" for each specific mutant FAD2 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify a mutant FAD2 specific fragment that can be used as a "specific probe" for identifying a specific mutant FAD2 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant FAD2 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant FAD2 allele (hereinafter referred to as "mutant FAD2 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant FAD2 allele.

Specific probes suitable for the invention may be the following:
  oligonucleotides ranging in length from 13 nt to about 1000 nt, comprising a nucleotide sequence of at least 13 consecutive nucleotides selected from the 5' or 3' flanking sequence of a specific mutant FAD2 allele or the complement thereof (i.e., for example, the sequence 5' or 3' flanking the one or more nucleotides deleted, inserted or substituted in the mutant FAD2 alleles of the invention, such as the sequence 5' or 3' flanking the non-sense, mis-sense, frameshift or splice site mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or oligonucleotides ranging in length from 13 nt to about 1000 nt, comprising a nucleotide sequence of at least 13 consecutive nucleotides selected from the mutation sequence of a specific mutant FAD2 allele or the complement thereof (i.e., for example, the sequence of nucleotides inserted or substituted in the FAD2 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be no longer than 50, more preferably not longer than 25 or even no longer than 20 or 15 nucleotides. Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant FAD2 alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense, frameshift or splice site mutations in the FAD2 genes of the invention described above and the sequence of the non-sense, mis-sense, frameshift or splice site mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Examples of specific probes suitable to identify specific mutant fad2 alleles are described in the Examples.

Detection and/or identification of a "mutant FAD2 specific region" hybridizing to a specific probe can occur in various ways, e.g., via size estimation after gel electrophoresis or via fluorescence-based detection methods. Other sequence specific methods for detection of a "mutant FAD2 specific region" hybridizing to a specific probe are also known in the art.

Alternatively, plants or plant parts comprising one or more mutant fad2 alleles can be generated and identified using other methods, such as the "Delete-a-Gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant fad2 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in FAD2 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant fad2 alleles. As for the mutagenesis techniques above, preferably *Brassica* species are screened which comprise an A and/or a C genome, so that the identified fad2 allele can subsequently be introduced into other *Brassica* species, such as *Brassica napus*, by crossing (inter- or intraspecific crosses) and selection. In ECOTILLING natural polymorphisms in breeding lines or related species are screened for by the TILLING methodology described above, in which individual or pools of plants are used for PCR amplification of the fad2 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant fad2 alleles (and *Brassica* plants comprising one or more of these) can be identified. The desired mutant alleles can then be combined with the desired wild type alleles by crossing and selection methods as described further below. Finally a single plant comprising the desired number of mutant fad2 and the desired number of wild type FAD2 alleles is generated.

Oligonucleotides suitable as PCR primers or specific probes for detection of a specific mutant FAD2 allele can also be used to develop methods to determine the zygosity status of the specific mutant FAD2 allele.

To determine the zygosity status of a specific mutant FAD2 allele, a nucleic acid amplification-based assay can be developed to determine the presence of a mutant and/or corresponding wild type FAD2 specific allele:

To determine the zygosity status of a specific mutant FAD2 allele, two primers specifically recognizing the wild-type FAD2 allele can be designed in such a way that they are directed towards each other and have the mutation region located in between the primers. These primers may be primers specifically recognizing the 5' and 3' flanking sequences, respectively. This set of primers allows simultaneous diagnostic amplification of the mutant, as well as of the corresponding wild type FAD2 allele.

Alternatively, to determine the zygosity status of a specific mutant FAD2 allele, two primers specifically recognizing the wild-type FAD2 allele can be designed in such a way that they are directed towards each other and that one of them specifically recognizes the mutation region. These primers may be primers specifically recognizing the sequence of the 5' or 3' flanking region and the mutation region of the wild type FAD2 allele, respectively. This set of primers, together with a third primer which specifically recognizes the sequence of the mutation region in the mutant FAD2 allele, allow simultaneous diagnostic amplification of the mutant FAD2 gene, as well as of the wild type FAD2 gene.

Alternatively, to determine the zygosity status of a specific mutant FAD2 allele, two primers specifically recognizing the wild-type FAD2 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type FAD2 allele, respectively. This set of primers, together with a third primer which specifically recognizes the joining region between the mutation region and the 3' or 5' flanking region of the mutant FAD2 allele, respectively, allow simultaneous diagnostic amplification of the mutant FAD2 gene, as well as of the wild type FAD2 gene.

Alternatively, the zygosity status of a specific mutant FAD2 allele can be determined by using alternative primer sets that specifically recognize mutant and wild type FAD2 alleles.

If the plant is homozygous for the mutant FAD2 gene or the corresponding wild type FAD2 gene, the diagnostic amplification assays described above will give rise to a single amplification product typical, preferably typical in length, for either the mutant or wild type FAD2 allele. If the plant is heterozygous for the mutant FAD2 allele, two specific amplification products will appear, reflecting both the amplification of the mutant and the wild type FAD2 allele.

Identification of the wild type and mutant FAD2 specific amplification products can occur e.g. by size estimation after gel or capillary electrophoresis (e.g. for mutant FAD2 alleles comprising a number of inserted or deleted nucleotides which results in a size difference between the fragments amplified from the wild type and the mutant FAD2 allele, such that said fragments can be visibly separated on a gel); by evaluating the presence or absence of the two different fragments after gel or capillary electrophoresis, whereby the diagnostic amplification of the mutant FAD2 allele can, optionally, be performed separately from the diagnostic amplification of the wild type FAD2 allele; by direct sequencing of the amplified fragments; or by fluorescence-based detection methods.

Examples of primers suitable to determine the zygosity of specific mutant FAD2 alleles are described in the Examples.

Alternatively, to determine the zygosity status of a specific mutant FAD2 allele, a hybridization-based assay can be developed to determine the presence of a mutant and/or corresponding wild type FAD2 specific allele:

To determine the zygosity status of a specific mutant FAD2 allele, two specific probes recognizing the wild-type FAD2 allele can be designed in such a way that each probe specifically recognizes a sequence within the FAD2 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type FAD2 allele.

Alternatively, to determine the zygosity status of a specific mutant FAD2 allele, two specific probes recognizing the wild-type FAD2 allele can be designed in such a way that one of them specifically recognizes a sequence within the FAD2 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type FAD2 allele, respectively. The use of one or, preferably, both of these probes, optionally, together with a third probe which specifically recognizes the sequence of the mutation region in the mutant FAD2 allele, allow diagnostic hybridization of the mutant and of the wild type FAD2 gene.

Alternatively, to determine the zygosity status of a specific mutant FAD2 allele, a specific probe recognizing the wild-type FAD2 allele can be designed in such a way that the probe specifically recognizes the joining region between the 5' or 3' flanking region, preferably the 5' flanking region, and the mutation region of the wild type FAD2 allele. This probe, optionally, together with a second probe that specifically recognizes the joining region between the 5' or 3' flanking region, preferably the 5' flanking region, and the mutation region of the mutant FAD2 allele, allows diagnostic hybridization of the mutant and of the wild type FAD2 gene.

Alternatively, the zygosity status of a specific mutant FAD2 allele can be determined by using alternative sets of probes that specifically recognize mutant and wild type FAD2 alleles.

If the plant is homozygous for the mutant FAD2 gene or the corresponding wild type FAD2 gene, the diagnostic hybridization assays described above will give rise to a single specific hybridization product, such as one or more hybridizing DNA (restriction) fragments, typical, preferably typical in length, for either the mutant or wild type FAD2 allele. If the plant is heterozygous for the mutant FAD2 allele, two specific hybridization products will appear, reflecting both the hybridization of the mutant and the wild type FAD2 allele.

Identification of the wild type and mutant FAD2 specific hybridization products can occur e.g. by size estimation after gel or capillary electrophoresis (e.g. for mutant FAD2 alleles comprising a number of inserted or deleted nucleotides which results in a size difference between the hybridizing DNA (restriction) fragments from the wild type and the mutant FAD2 allele, such that said fragments can be visibly separated on a gel); by evaluating the presence or absence of the two different specific hybridization products after gel or capillary electrophoresis, whereby the diagnostic hybridization of the mutant FAD2 allele can, optionally, be performed separately from the diagnostic hybridization of the wild type FAD2 allele; by direct sequencing of the hybridizing DNA (restriction) fragments; or by fluorescence-based detection methods.

Furthermore, detection methods specific for a specific mutant FAD2 allele that differ from PCR- or hybridization-based amplification methods can also be developed using the specific mutant FAD2 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant FAD2 allele in biological samples or the determination of the zygosity status of plant material comprising a specific mutant FAD2 allele. More particularly, a preferred embodiment of the kit of the invention comprises at least two specific primers, as described above, for identification of a specific mutant FAD2 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant FAD2 allele therein, as described above, for identification of a specific mutant FAD2 allele, or at least two or three specific probes for the determination of the zygosity status. Optionally, the kit can further comprise any other reagent (such as but not limited to hybridizing buffer, label) for identification of a specific mutant FAD2 allele in biological samples, using the specific probe.

The kit of the invention can be used, and its components can be specifically adjusted, for purposes of quality control (e.g., purity of seed lots), detection of the presence or absence of a specific mutant FAD2 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant FAD2 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant FAD2 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant FAD2 allele, implying the presence of nucleic acids in the samples. Thus the methods referred to herein for identifying a specific mutant FAD2 allele in biological samples, relate to the identification in biological samples of nucleic acids that comprise the specific mutant FAD2 allele.

In another embodiment, a method is provided for combining at least one knock-out fad2 allele of a FAD2-A1 gene, with at least one knock-out fad2 allele of a FAD2-C2 gene in a single *Brassica napus* plant, said method comprising a) generating and/or identifying two or more plants each comprising one or more selected knock-out fad2 alleles; b) crossing a first plant comprising one or more selected knockout fad2 alleles with a second plant comprising one or more other selected knockout fad2 alleles; c) collecting seeds from the cross, and, optionally, identifying a plant comprising at least one knock-out fad2 allele of a FAD2-A1 gene and at least one knock-out fad2 allele of a FAD2-C2 gene; and, optionally d) repeat steps b) and c) until a plant comprising at least one knock-out fad2 allele of a FAD2-A1 gene and at least one knock-out fad2 allele of a FAD2-C2 gene, is obtained. In another embodiment, said plant obtained in step d) comprising at least one knock-out fad2 allele of a FAD2-A1 gene and at least one knock-out fad2 allele of a FAD2-C2 gene, comprises a FAD2-C1 gene of which the fad2 alleles encode a functional FAD2 protein and comprises a FAD2-A2 gene of which the fad2 alleles are knock-out fad2 alleles.

Levels of C18:1 in seed of a *Brassica* plant can be increased by generating and/or selecting a *Brassica napus* plant comprising a FAD2-A1, a FAD2-A2, a FAD2-C1 and a FAD2-C2 gene, wherein said plant comprises knock-out fad2 alleles of the FAD2-A1 and of the FAD2-C2 genes, and wherein the fad2 alleles of said FAD2-C1 gene encode a functional FAD2 protein, as described above, and selecting a plant with increased levels of C18:1 in the seeds, while maintaining normal agronomic development.

A hybrid *Brassica napus* plant or seed comprising four FAD2 genes having increased levels of C18:1 while maintaining normal agronomic development, can be made by generating and/or identifying a first plant comprising a knockout fad2 allele of a FAD2-A1 gene, a knock-out allele of a FAD2-C2 gene, and a FAD2 allele of a FAD2-C1 gene which encodes a functional protein, in homozygous state and a second plant comprising a knockout fad2 allele of a FAD2-A1 gene, a knock-out allele of a FAD2-C2 gene, and a FAD2 allele of a FAD2-C1 gene which encodes a functional protein in homozygous state, as described above, crossing the first and the second plant and collecting F1 hybrid seeds from the cross comprising said fad2 alleles.

Knockout fad2 alleles according to the invention can be combined according to standard breeding techniques.

Knockout fad2 alleles can, for example, be transferred from one *Brassica* plant to another by a) generating and/or identifying a first plant comprising one or more selected knockout fad2 alleles, as described above, or generating the first plant by combining the one or more selected knockout fad2 alleles in one plant, as described above (wherein the first plant is homozygous or heterozygous for the one or more knockout fad2 alleles), b) crossing the first plant comprising the one or more knockout fad2 alleles with a second plant not comprising the one or more knockout fad2 alleles, collecting F1 seeds from the cross (wherein the seeds are heterozygous for a knockout fad2 allele if the first plant was homozygous for that knockout fad2 allele, and wherein half of the seeds are heterozygous and half of the seeds are azygous for, i.e. do not comprise, a knockout fad2 allele if the first plant was heterozygous for that knockout fad2 allele), and, optionally, identifying F1 plants comprising one or more selected knockout fad2 alleles, as described above, c) backcrossing F1 plants comprising one or more selected knockout fad2 alleles with the second plant not comprising the one or more selected knockout fad2 alleles for one or more generations (x), collecting BCx seeds from the crosses, and identifying in every generation BCx plants comprising the one or more selected knockout fad2 alleles, as described above, d) optionally, generating BCx plants which are homozygous for the one or more selected knockout fad2 alleles by performing one of the following steps:

- extracting doubled haploid plants from treated microspore or pollen cells of BCx plants comprising the one or more desired knockout fad2 allele(s), as described above,
- selfing the BCx plants comprising the one or more desired knockout fad2 allele(s) for one or more generations (y), collecting BCx Sy seeds from the selfings, and identifying BCx Sy plants, which are homozygous for the one or more desired knockout fad2 allele, as described above.

The first and the second *Brassica* plant can be *Brassica napus* plants. Alternatively, the first plant can be a *Brassica napus* plant, and the second plant can be a *Brassica napus* breeding line. "Breeding line", as used herein, is a preferably homozygous plant line distinguishable from other plant lines by a preferred genotype and/or phenotype that is used to produce hybrid offspring.

In a further aspect of the invention, a knock-out fad2 allele of a FAD2 gene is provided, wherein the knock-out fad2 allele is a mutated version of the native FAD2 gene, wherein the native FAD2 gene is selected from the group consisting of: (a) a FAD2-A1 gene comprising a sequence having at least 90% sequence identity to the sequence of SEQ ID NO: 4, or having a cDNA sequence having at least 90% sequence identity to the sequence of SEQ ID NO: 5, or encoding a protein having at least 90% sequence identity to the sequence of SEQ ID NO: 6; and (b) a FAD2-C2 gene comprising a sequence having at least 90% sequence identity to the sequence of SEQ ID NO: 13, or having a cDNA sequence having at least 90% sequence identity to the sequence of SEQ ID NO: 14, or encoding a protein having at least 90% sequence identity to the sequence of SEQ ID NO: 15, such as a knock-out fad2 allele which is a mutant allele of said FAD2-A1 gene comprising a C to T substitution at a position corresponding to position 2371 of SEQ ID NO: 4; or which is a mutant allele of said FAD2-C2 gene comprising a G to A substitution at a position corresponding to position 2327 of SEQ ID NO: 52.

In a further embodiment, a method is provided for producing oil, comprising harvesting seeds from the plants according to the invention, i.e. plants comprising a the knock-out FAD2 genes of the invention, and extracting the oil from said seeds.

In yet a further embodiment, a method is provided of producing food or feed, such as oil, meal, gain, starch, flour or protein, or an industrial product, such as biofuel, fiber, industrial chemicals, a pharmaceutical or a neutraceutical, comprising obtaining the plant or a part thereof according to the invention, and preparing the food, feed or industrial product from the plant or part thereof.

Another embodiment provides the use of the knock-out fad2 allele according to the invention to increase the level of C18:1 in the seed oil of a *Brassica napus* plant while maintaining normal agronomic development. Yet another embodiment provides a method to produce a *Brassica napus* plant comprising an increased level of C18:1 in the seed oil and which maintains normal agronomic development, said method comprising sowing seeds according to the invention and growing plants from said seeds.

Plants according to the invention, such as plants comprising the knock-out FAD2 genes according to the invention can further be used to produce seeds, such as seeds with increased levels of C18:1, or to produce seed oil with increased levels of C18:1.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EP0 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonyl aminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesterase increase to obtain high laureate, which confers pollination control, such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists:

Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin.

Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Trifloxystrobin, *Bacillus firmus, Bacillus firmus* strain 1-1582, *Bacillus subtilis, Bacillus subtilis* strain GB03, *Bacillus subtilis* strain QST 713, *Bacillus pumulis, Bacillus. pumulis* strain GB34.

Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N % cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

In some embodiments, the plant cells of the invention, i.e. a plant cell comprising a knock-out fad2 gene, as well as plant cells generated according to the methods of the invention, may be non-propagating cells.

The obtained plants according to the invention can be used in a conventional breeding scheme to produce more plants with the same characteristics or to introduce the characteristic according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny, or to produce food or feed, such as oil, meal, grain, starch, flour or protein, or an industrial product, such as biofuel, fiber, industrial chemicals, a pharmaceutical or a neutraceutical, or to produce hybrids of plants obtained by methods of the invention.

All patents, patent applications, and publications or public disclosures (including publications on internet) referred to or cited herein are incorporated by reference in their entirety.

The sequence listing contained in the file named "BCS15-2004-WO1_ST25.txt", which is 198 kilobytes (size as measured in Microsoft Windows®), contains 51 sequences SEQ ID NO: 1 through SEQ ID NO: 51 and is filed herewith by electronic submission and is incorporated by reference herein.

In the description and examples, reference is made to the following sequences:

Sequences

SEQ ID No. 1: Genomic DNA sequence of FAD2 from *Arabidopsis thaliana*.

SEQ ID No. 2: cDNA sequence of FAD2 from *Arabidopsis thaliana*.

SEQ ID No. 3: protein sequence of FAD2 from *Arabidopsis thaliana*.

SEQ ID No. 4: Genomic DNA sequence of FAD2-A1 from *Brassica napus*.

SEQ ID No. 5: cDNA sequence of FAD2-A1 from *Brassica napus*.

SEQ ID No. 6: protein sequence of FAD2-A1 from *Brassica napus*.

SEQ ID No. 7: Genomic DNA sequence of FAD2-C1 from *Brassica napus*.

SEQ ID No. 8: cDNA sequence of FAD2-C1 from *Brassica napus*.

SEQ ID No. 9: protein sequence of FAD2-C1 from *Brassica napus*.

SEQ ID No. 10: Genomic DNA sequence of FAD2-A2 from *Brassica napus*.

SEQ ID No. 11: cDNA sequence of FAD2-A2 from *Brassica napus*.

SEQ ID No. 12: protein sequence of FAD2-A2 from *Brassica napus*.

SEQ ID No. 13: Genomic DNA sequence of FAD2-C2 from *Brassica napus*.

SEQ ID No. 14: cDNA sequence of FAD2-C2 from *Brassica napus*.

SEQ ID No. 15: protein sequence of FAD2-C2 from *Brassica napus*.

SEQ ID No. 16: Genomic DNA sequence of FAD2-1 from *Brassica rapa*.

SEQ ID No. 17: cDNA sequence of FAD2-1 from *Brassica rapa*.

SEQ ID No. 18: protein sequence of FAD2-1 from *Brassica rapa*.

SEQ ID No. 19: Genomic DNA sequence of FAD2-2 from *Brassica rapa*.

SEQ ID No. 20: cDNA sequence of FAD2-2 from *Brassica rapa*.

SEQ ID No. 21: protein sequence of FAD2-2 from *Brassica rapa*.

SEQ ID No. 22: Genomic DNA sequence of FAD2-1 from *Brassica oleracea*.

SEQ ID No. 23: cDNA sequence of FAD2-1 from *Brassica oleracea*.

SEQ ID No. 24: protein sequence of FAD2-1 from *Brassica oleracea*.

SEQ ID No. 25: Genomic DNA sequence of FAD2-2 from *Brassica oleracea*.

SEQ ID No. 26: cDNA sequence of FAD2-2 from *Brassica oleracea*.

SEQ ID No. 27: protein sequence of FAD2-2 from *Brassica oleracea*.

SEQ ID No. 28: FAM primer HIOL101.

SEQ ID No. 29: VIC primer HIOL101.

SEQ ID No. 30: Reverse primer HIOL101.

SEQ ID No. 31: FAM primer HIOL103.

SEQ ID No. 32: VIC primer HIOL103.
SEQ ID No. 33: Reverse primer HIOL103.
SEQ ID No. 34: FAM primer HIOL109.
SEQ ID No. 35: VIC primer HIOL109.
SEQ ID No. 36: Reverse primer HIOL109.
SEQ ID No. 37: Genomic DNA sequence of FAD3-A1 from *Brassica napus*.
SEQ ID No. 38: protein sequence of FAD3-A1 from *Brassica napus*.
SEQ ID No. 39: cDNA sequence of FAD3-A1 from *Brassica napus*.
SEQ ID No. 40: Genomic DNA sequence of FAD3-A2 from *Brassica napus*.
SEQ ID No. 41: protein sequence of FAD3-A2 from *Brassica napus*.
SEQ ID No. 42: cDNA sequence of FAD3-A2 from *Brassica napus*.
SEQ ID No. 43: Genomic DNA sequence of FAD3-A3 from *Brassica napus*.
SEQ ID No. 44: protein sequence of FAD3-A3 from *Brassica napus*.
SEQ ID No. 45: cDNA sequence of FAD3-A3 from *Brassica napus*.
SEQ ID No. 46: Genomic DNA sequence of FAD3-C1 from *Brassica napus*.
SEQ ID No. 47: protein sequence of FAD3-C1 from *Brassica napus*.
SEQ ID No. 48: cDNA sequence of FAD3-C1 from *Brassica napus*.
SEQ ID No. 49: Genomic DNA sequence of FAD3-C2 from *Brassica napus*.
SEQ ID No. 50: protein sequence of FAD3-C2 from *Brassica napus*.
SEQ ID No. 51: cDNA sequence of FAD3-C2 from *Brassica napus*.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany. Standard procedures for AFLP analysis are described in Vos et al. (1995, NAR 23:4407-4414) and in published EP patent application EP 534858.

Example 1—Isolation of the DNA Sequences of *Brassica* FAD2 Genes

A TBLASTN homology search using the *A. thaliana* FAD2 gene sequence (At3G12120) was used as the query in a BLAST homology search of in-house databases of *Brassica rapa* sequences and of *Brassica oleracea* sequences. The BLAST analyses resulted in the identification of 2 FAD2 gene homologs for *B. rapa* (BrFAD2-1 (SEQ ID No. 16), BrFAD2-2 (SEQ ID No. 19), and 2 FAD2 gene homologs for *B. oleracea* (BoFAD2-1 (SEQ ID No. 22), BoFAD2-2 (SEQ ID No. 25). cDNAs corresponding to these sequences were predicted using FgeneSH software, and are depicted in SEQ ID No. 17, SEQ ID No. 20, SEQ ID No. 23, and SEQ ID No. 26, respectively. A BLAST homology search of an in-house database containing *Brassica napus* mRNA sequences using the *B. rapa* BrFAD2 gene sequences resulted in the identification of the cDNA sequences of *B. napus* BnFAD2-A1 (SEQ ID No. 5), and BnFAD2-A2 (SEQ ID No. 11). Based on gene structure predictions using the Fgenesh software or mRNA derived sequencing read abundance the corresponding coding sequences were identified. Similarly, a BLAST homology search of the in-house database containing *Brassica napus* mRNA sequences using the *B. oleracea* BoFAD2 gene sequences as a query resulted in the identification of the cDNA sequences of BnFAD2-C1 (SEQ ID No. 8), and BnFAD2-C2 (SEQ ID No. 14). The corresponding coding sequences were obtained following the above-mentioned gene structure prediction methods.

In order to retrieve the *B. napus* FAD2 gene sequences a BAC library was screened. Following standard GS-FLX sequencing of the positive library clones and de novo contig assembly using the 454 assembly software Newbler the gene sequences for BnFAD2-A1 (SEQ ID No. 4), BnFAD2-A2 (SEQ ID No. 10), BnFAD2-C1 (SEQ ID No. 7) and BnFAD2-C2 (SEQ ID No. 13) were identified.

The *B. napus* BnFAD2-A1, BnFAD2-C1, and BnFAD2-C2 genes, *B. rapa* BrFAD2-1 gene, and the *B. oleracea* BoFAD2-1 gene, encode FAD2 proteins of 384 amino acids (SEQ ID NOs: 6, 9, 15, 18, and 24, respectively).

The *B. oleracea* BoFAD2-2 gene contains a 1 nt deletion at a position corresponding to position 2608 of the BnFAD2-C2 gene (SEQ ID NO: 13) (i.e. the position after position 2726 of the BoFAD2-2 gene (SEQ ID NO: 25), resulting in a frameshift mutation, leading to a truncated protein of 290 amino acids (SEQ ID NO: 27).

The *B. napus* BnFAD2-A2 and *B. rapa* BrFAD2-2 genes contain missing nucleotides at a position corresponding to positions 2036-2042 of BnFAD2-C2 gene (SEQ ID NO: 13), leading to a frameshift and premature stop codon in the coding sequence, resulting in truncated proteins of 136 amino acids (SEQ ID NO: 12 (BnFAD2-A2 protein and SEQ ID NO: 21 (BrFAD2-2 protein). The BnFAD2-A2 and BrFAD2-2 genes therefore represent nonfunctional pseudogenes.

Alignment of the proteins encoded by the *Brassica* FAD2 genes as described herein are shown in FIG. 1.

Example 2—Expression Analysis of *Brassica napus* FAD2 Genes

The relative gene expression levels of *Brassica napus* FAD2 genes were determined through analysis of Illumina mRNAseq derived transcriptome databases obtained for multiple tissues and developmental stages. Gene expression levels were calculated taking into account a normalization step for the sequencing depth per database (target reads per million reads in the database) and for the target gene length (reads per kilobase per million reads in the database) [RPKM; Mortazavi A, Williams B A, McCue K, Schaeffer L, Wold B: Mapping and quantifying mammalian transcriptomes by RNA-Seq. Nature Methods (2008), 5(7):621-628].

The result of the expression analysis is shown in FIG. 2. From this figure it can be seen that BnFAD2-A1 and BnFAD2-C1 have the highest levels of expression, and that the expression is highest in seeds.

Example 3—Generation and Isolation of Mutant Brassica napus Fad2 Alleles

Mutations in the FAD2 genes from *Brassica napus* identified in Example 1 were generated and identified as follows: 30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.

The mutagenized seeds (M1 seeds) were rinsed 3 times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the FAD2 genes causing the introduction of STOP codons in the protein-encoding regions of the FAD2 genes, or amino acid substitutions, by direct sequencing by standard sequencing techniques and analyzing the sequences for the presence of the point mutations using the NovoSNP software.

The following mutant fad2 alleles were thus identified:

TABLE 2a
mutations in Bn FAD2-A1

| Plant name | Nt pos Genomic SEQ ID 4 | Nt pos cDNA SEQ ID 5 | AA pos. SEQ ID 6 | WT → mut codon | WT → mut AA |
|---|---|---|---|---|---|
| HIOL101* | 2371 | 615 | 109 | CAC→ TAC | H→Y |

TABLE 2b
mutations in BnFAD2-C1

| Plant name | Nt pos Genomic SEQ ID 7 | Nt pos cDNA SEQ ID 8 | AA pos. SEQ ID 9 | WT → mut codon | WT → mut AA |
|---|---|---|---|---|---|
| HIOL103 | 3223 | 620 | 101 | TGG→ TGA | W→ STOP |

TABLE 2c
mutations in BnFAD-A2

| Plant name | Nt pos Genomic SEQ ID 10 | Nt pos cDNA SEQ ID 11 | AA pos. SEQ ID 12 | WT → mut codon | Wt → mut AA |
|---|---|---|---|---|---|
| HIOL111 | 2057 | 798 | | CGA→ TGA | STOP |

TABLE 2d
mutations in BnFAD-C2

| Plant name | Nt pos Genomic SEQ ID 13 | Nt pos cDNA SEQ ID 14 | AA pos. SEQ ID 15 | WT → mut codon | WT → mut AA |
|---|---|---|---|---|---|
| HIOL109* | 2327 | 721 | 109 | TGG→ TAG | W→ STOP |

Footnotes*: Seeds comprising a mutant BnFAD1-A1 allele comprising the HIOL101 mutation, or a mutant BnFAD1-C2 allele comprising the HIOL109 mutation have been deposited at the NCIMB (NCIMB Ltd, Ferguson Building, Craibstone Estate, Bucksburn, Aberdeen AB21 9YA, Scotland, UK) on 26 Feb. 2015, under accession number NCIMB 42376, and NCIMB 42375, respectively.

Example 4—Oil Composition in Seeds from Brassica napus Comprising BnFAD2-A1, BnFAD2-C1, BnFAD2-A2, and BnFAD2-C2 Knock-Out Alleles Grown in the Greenhouse

*Brassica* plants comprising mutant BnFAD2-A1, BnFAD2-C1, BnFAD2-A2, and BnFAD2-C2 alleles were crossed. Following selfing seeds from plants homozygous for BnFAD2-A1, Bn FAD2-C1, BnFAD2-A2 or BnFAD2-C2 mutations and combinations thereof, or wild type segregants (i.e. not comprising any mutant FAD2 allele that would impact the normal function of a FAD2 protein) were obtained based on molecular marker based selection of plants (see below).

The fatty acid composition of the seed oil of the above *Brassica* plants grown in the greenhouse was determined by extracting the fatty acyls from the seeds and analyzing their relative levels in the seed oil by capillary gas-liquid chromatography as described in WO09/007091.

Fatty acid composition was determined from plants grown in the greenhouse in seeds of the *Brassica* lines with mutant BnFAD2-A1, BnFAD2-C1, BnFAD2-A1, or BnFAD2-C2 alleles, and combinations thereof, and in wild-type segregants. Wild type check refers to a reference *B. napus* genotype that was not subject to EMS treatment.

TABLE 3

Average C18:0, C18:1, C18:2 and C18:3 levels (% of oil weight in seed) and standard deviation (SD) in seeds of Brassica napus plants with different combinations of mutations in the BnFAD2-A1, BnFAD2-C1, BnFAD2-A2 and BnFAD2-C2 genes, grown in the greenhouse. A1, C1, C2 refers to presence of mutant alleles; — refers to presence of wild-type alleles.

| Genotype | C18:0 (AV) | C18:0 (SD) | C18:1 (AV) | C18:1 (SD) | C18:2 (AV) | C18:2 (SD) | C18:3 (AV) | C18:3 (SD) |
|---|---|---|---|---|---|---|---|---|
| HIOL101/HIOL111/HIOL103/HIOL109 (A1/A2/C1/C2) | 2.0 | 0.5 | 84.5 | 0.8 | 1.8 | 0.3 | 3.1 | 0.3 |
| HIOL101/HIOL111/HIOL103/HIOL109 (A1/—/C1/C2) | 1.4 | 0.1 | 85.4 | 0.8 | 1.4 | 0.3 | 2.9 | 0.1 |
| HIOL101/HIOL111/HIOL103/HIOL109 (A1/A2/—/C2) | 1.8 | 0.4 | 71.0 | 1.5 | 9.0 | 0.9 | 8.1 | 0.6 |

TABLE 3-continued

Average C18:0, C18:1, C18:2 and C18:3 levels (% of oil weight in seed) and standard deviation (SD) in seeds of Brassica napus plants with different combinations of mutations in the BnFAD2-A1, BnFAD2-C1, BnFAD2-A2 and BnFAD2-C2 genes, grown in the greenhouse. A1, C1, C2 refers to presence of mutant alleles; — refers to presence of wild-type alleles.

| Genotype | C18:0 (AV) | C18:0 (SD) | C18:1 (AV) | C18:1 (SD) | C18:2 (AV) | C18:2 (SD) | C18:3 (AV) | C18:3 (SD) |
|---|---|---|---|---|---|---|---|---|
| HIOL101/HIOL111/HIOL103/HIOL109 (A1/A2/C1/—) | 1.8 | 0.4 | 83.2 | 0.6 | 2.0 | 0.1 | 4.3 | 0.3 |
| HIOL101/HIOL111/HIOL103/HIOL109 (A1/—/—/C2) | 1.6 | 0.2 | 70.2 | 3.2 | 10.0 | 1.6 | 8.7 | 1.5 |
| HIOL101/HIOL111/HIOL103/HIOL109 (A1/—/C1/—) | 1.8 | 0.2 | 82.4 | 0.5 | 2.4 | 0.3 | 4.5 | 0.4 |
| HIOL101/HIOL111/HIOL103/HIOL109 (A1/A2/—/—) | 1.5 | 0.3 | 68.0 | 3.8 | 10.5 | 1.1 | 9.4 | 0.2 |
| HIOL101/HIOL111/HIOL103/HIOL109 (A1/—/—/13) | 2.0 | 0.3 | 71.5 | 1.8 | 10.0 | 0.9 | 8.1 | 0.8 |

Table 3 shows that the FAD2-A1 and the FAD2-C1 mutants have the highest effect on C18:1 levels in the seeds, and that addition of the FAD2-C2 mutant increases the levels of C18:1 even further. The FAD2-A2 mutant does not further contribute to the increase the levels of C18:1 in the seeds.

Example 5—Oil Composition in Seeds from Brassica napus Comprising BnFAD2-A1, BnFAD2-C1, BnFAD2-A2, and BnFAD2-C2 Knock-Out Alleles Grown in the Field Fatty acid composition and plant performance parameters were determined from plants grown in the field as described above in seeds of the Brassica lines with mutant BnFAD2-A1, BnFAD2-C1, BnFAD2 A2 or BnFAD2-C2 alleles, and combinations thereof, and in wild type segregants not comprising any of the mutant BnFAD2 alleles. The mutant genotypes were tested at three locations for two different geographic areas.

Fatty acid composition in the seed oil was determined as described above. In three locations of one of the geographic areas, the following plant performance parameters were determined: Vigor (VIG) at the 4-5 leaf stage on a scale 1-9, wherein 1=poor, 5=average, 9=vigorous; Flowering—Start (DTF): the stage (in days after seeding) at which 10% is in flower; total level of saturated fatty acids (FASAT); Oil content (OIL) in the seed in % of whole seed; protein content (PROT) in the seed in % of whole seed; Glucosinolate content (GLU) in the seed in moles/gram seeds. Seed quality parameters were obtained through GC analysis. For the statistical analysis an ANOVA test was run. Contrasts between the mutant lines versus the corresponding null-segregants were subject to significance testing. Wild type check refers to a reference B. napus genotype that was not subject to EMS treatment.

Table 4 shows the plant performance parameters of the plants with the different combinations of the BnFAD2 mutant alleles for the three locations in geographical area A, and Table 5 shows the fatty acid composition in the seed oil of plants with the different combinations of the BnFAD2 mutant alleles in the field for the two different geographical areas A and B.

TABLE 4

Agronomic performance of FAD2 mutants at geographical area A, average of three locations with standard deviation (SD). A1, A2, C1, C2 refers to presence of mutant alleles; — refers to presence of wild-type alleles. *: mutant significantly different from wild-type segregant.

| NAME | VIG AV | VIG SD | DTF AV | DTF SD | FASAT AV | FASAT SD | OIL AV | OIL SD | PROT AV | PROT SD | GLU AV | GLU STDEV |
|---|---|---|---|---|---|---|---|---|---|---|---|---|
| HIOL101/HIOL111/HIOL103/HIOL109 (A1/A2/C1/C2) | 1.5* | 0.8 | 53* | 0.9 | 6.6 | 0.7 | 38.8* | 2.5 | 33.9* | 2.1 | 21.7* | 4.0 |
| HIOL101/HIOL111/HIOL103/HIOL109 (A1/—/C1/C2) | 1.3* | 0.5 | 53* | 0.9 | 6.3 | 0.7 | 38.1* | 3.1 | 34.9* | 2.0 | 19.2* | 1.2 |
| HIOL101/HIOL111/HIOL103/HIOL109 (A1/A2/—/C2) | 7.0 | 0.0 | 48.7 | 0.8 | 7.9* | 0.4 | 46.4 | 1.8 | 26.7 | 1.5 | 15.4 | 2.6 |
| HIOL101/HIOL111/HIOL103/HIOL109 (A1/A2/C1/—) | 2.3* | 0.5 | 52.3* | 1.9 | 6.7 | 0.6 | 37.3* | 2.0 | 34.8* | 2.1 | 26.5* | 5.0 |
| HIOL101/HIOL111/HIOL103/HIOL109 (A1/—/—/C2) | 7.2 | 0.4 | 48.3 | 0.5 | 7.1 | 0.3 | 47.5 | 1.7 | 26.1 | 2.0 | 15.0 | 1.5 |
| HIOL101/HIOL111/HIOL103/HIOL109 (A1/—/C1/—) | 2.3* | 0.5 | 52.3* | 1.9 | 6.5 | 0.3 | 41.3* | 2.1 | 32.3* | 1.4 | 22.8* | 2.9 |
| HIOL101/HIOL111/HIOL103/HIOL109 (A1/A2/—/—) | 6.8 | 0.4 | 48.7 | 1.2 | 8.6* | 1.5 | 46.0 | 3.1 | 27.0 | 3.1 | 14.6 | 3.8 |
| HIOL101/HIOL111/HIOL103/HIOL109 (A1/—/—/—) | 7.2 | 0.4 | 48.3 | 0.5 | 7.0 | 0.2 | 47.1 | 1.2 | 25.7 | 1.1 | 17.3 | 2.3 |
| HIOL101/HIOL103/HIOL109 (A1/C1/C2) | 1.3* | 0.5 | 53* | 0.9 | 7.2 | 0.8 | 37* | 2.7 | 34* | 0.8 | 22.3* | 4.1 |
| HIOL101/HIOL103/HIOL109 (A1/C1/—) | 2.2* | 0.4 | 52.3* | 1.9 | 6.7 | 1.1 | 38* | 2.1 | 33.6* | 2.0 | 23.9* | 3.6 |
| HIOL101/HIOL103/HIOL109 (A1/—/C2) | 6.8 | 0.4 | 48.3 | 0.5 | 6.8 | 0.2 | 45.6 | 2.1 | 26.4 | 2.2 | 14.9 | 2.2 |

TABLE 4-continued

Agronomic performance of FAD2 mutants at geographical area A, average of three locations with standard deviation (SD). A1, A2, C1, C2 refers to presence of mutant alleles; — refers to presence of wild-type alleles. *: mutant significantly different from wild-type segregant.

| NAME | VIG AV | VIG SD | DTF AV | DTF SD | FASAT AV | FASAT SD | OIL AV | OIL SD | PROT AV | PROT SD | GLU AV | GLU STDEV |
|---|---|---|---|---|---|---|---|---|---|---|---|---|
| HIOL101/HIOL103/HIOL109 (—/C1/C2) | 6.3 | 0.5 | 48.0 | 0.6 | 6.7 | 0.2 | 43.7 | 1.5 | 27.9 | 2.2 | 15.6 | 2.6 |
| HIOL101/HIOL103/HIOL109 (A1/—/—) | 6.3 | 0.8 | 49.0 | 1.3 | 7.1 | 0.2 | 41.1* | 2.4 | 29.5 | 2.5 | 19.9* | 2.2 |
| HIOL101/HIOL103/HIOL109 (—/C1/—) | 6.7 | 0.5 | 48.7 | 0.8 | 7.1 | 0.1 | 41.9* | 1.0 | 28.7 | 1.1 | 19.7* | 2.5 |
| HIOL101/HIOL103/HIOL109 (—/—/C2) | 6.3 | 0.8 | 47.3 | 1.2 | 6.8 | 0.1 | 43.7 | 1.9 | 27.5 | 2.3 | 17.4 | 1.7 |
| HIOL101/HIOL103/HIOL109 (—/—/—) | 6.5 | 0.5 | 49.0 | 0.9 | 7.3 | 0.2 | 44.1 | 1.3 | 26.6 | 1.4 | 15.6 | 1.9 |
| Wild-type check | 8.2 | 1.0 | 45.8 | 2.1 | 6.6 | 0.2 | 48.7 | 3.0 | 24.5 | 3.4 | 15.1 | 1.6 |

TABLE 5a

Average C18:1 levels (% of oil weight in seed) and standard deviation (SD) in seeds of *Brassica napus* plants with different combinations of mutations in the BnFAD2-A1, BnFAD2-C1, BnFAD2-A2 and BnFAD2-C2 genes, grown in the field, bagselfed (BS) and open-pollinated (OP) in geographical area A.

| | Bagselfed (BS) | | | | Open pollinated (OP) | | | |
|---|---|---|---|---|---|---|---|---|
| GENOTYPE | C18:1 | SE | CI. lower | CI. upper | C18:1 | SE | CI. lower | CI. upper |
| HIOL101/HIOL103/HIOL109 (—/—/—) | 57.85 | 0.48 | 56.90 | 58.80 | 58.61 | 0.50 | 57.63 | 59.60 |
| HIOL101/HIOL103/HIOL109 (—/—/C2) | 59.57 | 0.48 | 58.62 | 60.52 | 61.10 | 0.48 | 60.17 | 62.03 |
| HIOL101/HIOL103/HIOL109 (—/C1/—) | 68.57 | 0.48 | 67.62 | 69.52 | 67.91 | 0.48 | 66.98 | 68.85 |
| HIOL101/HIOL103/HIOL109 (—/C1/C2) | 65.60 | 0.48 | 64.65 | 66.55 | 66.82 | 0.48 | 65.89 | 67.75 |
| HIOL101/HIOL103/HIOL109 (A1/—/—) | 68.78 | 0.48 | 67.84 | 69.73 | 67.99 | 0.48 | 67.06 | 68.92 |
| HIOL101/HIOL103/HIOL109 (A1/—/C2) | 71.78 | 0.48 | 70.83 | 72.73 | 71.83 | 0.48 | 70.90 | 72.76 |
| HIOL101/HIOL103/HIOL109 (A1/C1/—) | 82.30 | 0.48 | 81.35 | 83.25 | 81.53 | 0.48 | 80.59 | 82.46 |
| HIOL101/HIOL103/HIOL109 (A1/C1/C2) | 84.59 | 0.48 | 83.64 | 85.54 | 83.07 | 0.48 | 82.13 | 84.00 |
| HIOL101/HIOL111/HIOL103/HIOL109 (A1/—/C1/C2) | 86.31 | 0.48 | 85.36 | 87.26 | 80.95 | 0.48 | 80.02 | 81.89 |
| HIOL101/HIOL111/HIOL103/HIOL109 (A1/—/—/—) | 72.52 | 0.48 | 71.57 | 73.47 | 73.74 | 0.48 | 72.81 | 74.67 |
| HIOL101/HIOL111/HIOL103/HIOL109 (A1/—/—/C2) | 73.70 | 0.48 | 72.75 | 74.65 | 73.35 | 0.48 | 72.42 | 74.29 |
| HIOL101/HIOL111/HIOL103/HIOL109 (A1/—/C1/—) | 85.38 | 0.48 | 84.43 | 86.33 | 81.79 | 0.48 | 80.86 | 82.73 |
| HIOL101/HIOL111/HIOL103/HIOL109 (A1/A2/—/—) | 70.16 | 0.48 | 69.21 | 71.11 | 71.71 | 0.48 | 70.78 | 72.64 |
| HIOL101/HIOL111/HIOL103/HIOL109 (A1/A2/—/C2) | 72.64 | 0.48 | 71.69 | 73.59 | 71.93 | 0.48 | 71.00 | 72.86 |
| HIOL101/HIOL111/HIOL103/HIOL109 (A1/A2/C1/—) | 83.81 | 0.48 | 82.86 | 84.76 | 81.80 | 0.48 | 80.87 | 82.73 |
| HIOL101/HIOL111/HIOL103/HIOL109 (A1/A2/C1/C2) | 85.86 | 0.48 | 84.91 | 86.81 | 82.22 | 0.48 | 81.28 | 83.15 |
| Wild-type check | 61.73 | 0.48 | 60.78 | 62.68 | 62.15 | 0.48 | 61.22 | 63.09 |

A1, A2 C1, C2 refers to presence of mutant alleles;
— refers to presence of wild-type alleles.

TABLE 5b

Average C18:1 levels (% of oil weight in seed) and standard deviation (SD) in seeds of *Brassica napus* plants with different combinations of mutations in the BnFAD2-A1, BnFAD2-C1, BnFAD2-A2 and BnFAD2-C2 genes, grown in the field, caged and open-pollinated in geographical area B.

| | Caged | | | | Open-pollinated | | | |
|---|---|---|---|---|---|---|---|---|
| GENOTYPE | C18:1 | SE | CI. lower | CI. upper | C18:1 | SE | CI. lower | CI. upper |
| HIOL101/HIOL103/HIOL109 (—/—/—) | 61.45 | 0.44 | 60.6 | 62.31 | 60.96 | 0.44 | 60.11 | 61.82 |
| HIOL101/HIOL103/HIOL109 (—/—/C2) | 62.01 | 0.44 | 61.16 | 62.87 | 62.58 | 0.44 | 61.72 | 63.43 |
| HIOL101/HIOL103/HIOL109 (—/C1/—) | 66.18 | 0.45 | 65.3 | 67.06 | 66.19 | 0.44 | 65.34 | 67.05 |
| HIOL101/HIOL103/HIOL109 (—/C1/C2) | 69.38 | 0.44 | 68.53 | 70.24 | 68.96 | 0.44 | 68.1 | 69.82 |

TABLE 5b-continued

Average C18:1 levels (% of oil weight in seed) and standard deviation (SD) in seeds of *Brassica napus* plants with different combinations of mutations in the BnFAD2-A1, BnFAD2-C1, BnFAD2-A2 and BnFAD2-C2 genes, grown in the field, caged and open-pollinated in geographical area B.

| | Caged | | | | Open-pollinated | | | |
|---|---|---|---|---|---|---|---|---|
| GENOTYPE | C18:1 | SE | CI. lower | CI. upper | C18:1 | SE | CI. lower | CI. upper |
| HIOL101/HIOL103/HIOL109 (A1/—/—/—) | 70.32 | 0.44 | 69.46 | 71.18 | 70.27 | 0.44 | 69.42 | 71.13 |
| HIOL101/HIOL103/HIOL109 (A1/—/—/C2) | 73.48 | 0.44 | 72.63 | 74.34 | 73.41 | 0.44 | 72.55 | 74.26 |
| HIOL101/HIOL103/HIOL109 (A1/—/C1/—) | 81.99 | 0.47 | 81.07 | 82.92 | 79.31 | 0.44 | 78.45 | 80.16 |
| HIOL101/HIOL103/HIOL109 (A1/—/C1/C2) | NA | NA | NA | NA | 78.09 | 1.19 | 75.76 | 80.42 |
| HIOL101/HIOL111/HIOL103/HIOL109 (A1/—/C1/C2) | 85.08 | 0.65 | 83.8 | 86.36 | 79.83 | 0.58 | 78.7 | 80.97 |
| HIOL101/HIOL111/HIOL103/HIOL109 (A1/—/—/—) | 74.74 | 0.44 | 73.88 | 75.6 | 73.97 | 0.44 | 73.12 | 74.83 |
| HIOL101/HIOL111/HIOL103/HIOL109 (A1/—/—/C2) | 74.96 | 0.44 | 74.1 | 75.81 | 74.67 | 0.44 | 73.82 | 75.53 |
| HIOL101/HIOL111/HIOL103/HIOL109 (A1/—/C1/—) | 83.53 | 1.1 | 81.38 | 85.68 | 79.3 | 0.44 | 78.44 | 80.15 |
| HIOL101/HIOL111/HIOL103/HIOL109 (A1/A2/—/—) | 71.64 | 0.44 | 70.78 | 72.5 | 72.44 | 0.44 | 71.58 | 73.29 |
| HIOL101/HIOL111/HIOL103/HIOL109 (A1/A2/—/C2) | 72.91 | 0.44 | 72.05 | 73.77 | 73.08 | 0.44 | 72.22 | 73.93 |
| HIOL101/HIOL111/HIOL103/HIOL109 (A1/A2/C1/—) | 83.55 | 0.63 | 82.3 | 84.79 | 80.32 | 0.61 | 79.13 | 81.51 |
| HIOL101/HIOL111/HIOL103/HIOL109 (A1/A2/C1/C2) | 84.57 | 0.69 | 83.23 | 85.92 | 80.18 | 0.62 | 78.97 | 81.4 |
| Wild-type check | 65.51 | 0.44 | 64.65 | 66.37 | 65.52 | 0.44 | 64.66 | 66.37 |

A1, A2 C1, C2 refers to presence of mutant alleles;
— refers to presence of wild-type alleles.
NA = not analyzed.

From Tables 5a and 5b, it can be seen that, similar to in the greenhouse, also in the field, the combination of the A1 and the C1 mutation leads to the highest levels of C18:1 in the seed oil. Addition of the C2 mutation further increases the levels of C18:1 in the seed oil, but addition of the A2 mutation has only a minor contribution, or does not contribute at all, to increased C18:1 levels in the seed oil.

From Table 4, however, it can be observed that the combination of the A1 and C1 mutations leads to a significantly reduced agronomic performance of the plants: the vigor levels are significantly reduced from a level of 6.5 for the wild-type segregant, to between 1.3 and 2.3 for the mutant plants comprising both the A1 and the C1 mutations. Also, the number of days to flowering (DTF) is increased, the oil content is decreased, the protein content is increased, and the levels of glucosinolates are increased of plants comprising the A1 and the C1 mutation.

The plants with high levels of C18:1 which do not show this reduced agronomic performance are the plants comprising the A1 and the C2 mutation.

In summary, these results show that combination of a mutant FAD2 allele of the BnFAD2-A1 gene and of the BnFAD2-C2 gene, results in plants with high levels of oleic acid without agronomic penalty. More specifically, this combination of mutations can lead to levels of oleic acid of about 73% to almost 75% without agronomic penalty.

Example 6—Oil Composition in Seeds from *Brassica napus* Comprising Mutant FAD2 and Mutant FAD3 Alleles Plants comprising the mutant FAD2 alleles of the BnFAD2-A1 gene and on the BnFAD2-C2 gene as described herein, were combined with mutant FAD3 alleles as described in WO2011/060946 (incorporated herein by reference). Therefore, *Brassica* plants comprising mutant BnFAD2-A1, BnFAD2-C2, BnFAD3-A1, BnFAD3-A2, BnFAD3-A3, BnFAD3-C1, and BnFAD3-C2 alleles were crossed. Following selfing seeds from plants homozygous for BnFAD2-A1, BnFAD2-A2, BnFAD3-A1, BnFAD3-A2, BnFAD3-A3, BnFAD3-C1, or BnFAD3-C2 mutations and combinations thereof, or wild type segregants (i.e. not comprising any mutant FAD2 or FAD3 allele that would impact the normal function of a FAD2 or FAD3 protein) were obtained based on molecular marker based selection of plants (see below and WO2011/060946).

The levels of fatty acids in the seed oil were determined from plants grown in the greenhouse and from plants grown in the field as described above and in WO2011/060946. Table 6 shows the fatty acid levels of the plants grown in the greenhouse, and Table 7 shows the fatty acid levels of the plants grown in the field.

For the plants grown in the field, the agronomic performance was determined by determining the following plant performance parameters: Establishment (EST1) at the 2-3 leaf stage on a scale 1-9, wherein 1=very thin, 5=average, 9=very thick; Vigor (VIG1) at the 5-6 leaf stage on a scale 1-9, wherein 1=poor, 5=average, 9=vigorous; Flowering—Start (DTF): the stage (in days after seeding) at which 10% is in flower; Flowering—End (EOF): the stage (in days after seeding) at which 10% remains in flower; Plant Height (HICM) at the stage of flowering end in cm; Maturity (MAT) on a scale 1-9 wherein 1=late, 5=average, 9=early; Days to maturity (DTM) in days after seeding; Lodging Resistance at Maturity (LOM) at the maturity stage on a scale 1-9 wherein 1=0 degrees (flat), 5=45 degrees, 9=90 degrees (upright); Yield (YLD) of the seeds in grams per plot at 8% moisture; Oil content (OILN) in the seed in % of whole seed; protein content (PRON) in the seed in % of whole seed; and Glucosinolate content (GLUN) in the seed in μmoles/gram seeds. The agronomic parameters are shown in Table 8.

These data show that, by combining the knock-out mutant FAD2 alleles of the BnFAD2-A1 and the BnFAD2-C2 genes with mutant alleles of five FAD3 genes, seed oil can be obtained with increased C18:1 levels up to about 73 to about 75% and with reduced C18:3 levels. Whereas the vigor levels of the plants in the field is slightly reduced, the seed yield of the plants in the field is not significantly changed.

TABLE 6

Levels of different fatty acids of plants comprising mutant FAD2 and mutant FAD3 alleles grown in the greenhouse. Plants indicated with "HIOL101/HIOL109/LOLI105/LOLI108/LOLI111/LOLI103/LOLI115" contain the two mutant FAD2 alleles and the five mutant FAD3 alleles (homozygous) as indicated. Plants indicated with "LOLI105/LOLI108/LOLI111/LOLI103/LOLI115" contain the five mutant FAD3 alleles (homozygous), but wild-type FAD2 genes; plants indicated with HIOL101/HIOL109 contain the two mutant FAD2 alleles (homozygous) but wild-type FAD3 genes. *indicates a difference with the wild-type check.

| GENOTYPES | C14:0 % | C16:0 % | C16:1 % | C18:0 % | C18:1 % | C18:2 % | C18:3 % |
|---|---|---|---|---|---|---|---|
| HIOL101/H1OL109/LOLI105/LOLI108/LOLI111/LOLI103/LOLI115 (A1A1/C2C2/A1A1/A2A2/A3A3/C1C1/C2C2) | 0.07 | 3.87* | 0.34 | 1.69 | 75.79* | 14.81* | 0.72* |
| LOLI105/LOLI108/LOLI111/LOLI103/LOLI115 (A1A1/A2A2/A3A3/C1C1/C2C2) | 0.08 | 4.28* | 0.36* | 1.69 | 64.77* | 25.47* | 0.71* |
| HIOL101/H1OL109(A1A1/C2C2) | 0.07 | 4.02* | 0.35* | 1.68 | 74.94* | 7.95* | 8.39* |
| Wild-tye check | 0.08 | 4.40 | 0.34 | 1.67 | 62.66 | 18.39 | 9.97 |

| GENOTYPES | C20:0 % | C20:1 % | C20:2 % | C22:0 % | C22:1 % | C24:0 % | C24:1 % | SATS % |
|---|---|---|---|---|---|---|---|---|
| HIOL101/H1OL109/LOLI105/LOLI108/LOLI111/LOLI103/LOLI115 (A1A1/C2C2/A1A1/A2A2/A3A3/C1C1/C2C2) | 0.58 | 1.05* | 0.05 | 0.31 | 0.00 | 0.10 | 0.10 | 6.62* |
| LOLI105/LOLI108/LOLI111/LOLI103/LOLI115 (A1A1/A2A2/A3A3/C1C1/C2C2) | 0.58 | 0.96* | 0.06 | 0.31 | 0.00 | 0.10 | 0.11 | 7.03 |
| HIOL101/H1OL109(A1A1/C2C2) | 0.57 | 1.04* | 0.04 | 0.30 | 0.00 | 0.09 | 0.10 | 6.73* |
| Wild-tye check | 0.55 | 0.93 | 0.06 | 0.29 | 0.00 | 0.09 | 0.11 | 7.07 |

TABLE 7

Levels of different fatty acids of plants comprising mutant FAD2 and mutant FAD3 alleles grown in the field at geographical region A (A) and at geographical region B (B). Plants indicated with "HIOL101/HIOL109/LOLI105/LOLI108/LOLI111/LOLI103/LOLI115" contain the two mutant FAD2 alleles and the five mutant FAD3 alleles (homozygous) as indicated. Plants indicated with "LOLI105/LOLI108/LOLI111/LOLI103/LOLI115" contain the five mutant FAD3 alleles (homozygous), but wild-type FAD2 genes; plants indicated with HIOL101/HIOL109 contain the two mutant FAD2 alleles (homozygous) but wild-type FAD3 genes. *indicates a significant difference with the wild-type check.

A.

| GENOTYPES | C14:0 % | C16:0 % | C16:1 % | C18:0 % | C18:1 % | C18:2 % | C18:3 % | C20:0 % |
|---|---|---|---|---|---|---|---|---|
| HIOL101/HIOL109/LOLI105/LOLI108/LOLI111/LOLI103/LOLI115 | 0.09 | 3.66* | 0.34 | 1.58* | 72.95* | 16.27* | 1.73* | 0.63 |
| HIOL101/HIOL109 | 0.09 | 3.71* | 0.34 | 1.63* | 73.64* | 9.80* | 7.45* | 0.65 |
| LOLI105/LOLI108/LOLI111/LOLI103/LOLI115 | 0.09 | 4.00 | 0.34 | 1.65 | 62.55 | 26.43* | 1.62* | 0.65 |
| Wild-tye check | 0.09 | 4.01 | 0.33 | 1.74 | 61.98 | 20.24 | 8.38 | 0.66 |
| CV | 25.9 | 2.1 | 6.2 | 7.7 | 1.2 | 4.1 | 6.4 | 8.8 |

| GENOTYPES | C20:1 | C20:2 | C22:0 % | C22:1 % | C24:0 % | C24:1 % | SATS % |
|---|---|---|---|---|---|---|---|
| HIOL101/HIOL109/LOLI105/LOLI108/LOLI111/LOLI103/LOLI115 | 1.41* | 0.07 | 0.38 | 0.00 | 0.17 | 0.14 | 6.53* |
| HIOL101/HIOL109 | 1.42* | 0.06* | 0.37 | 0.00 | 0.17 | 0.14 | 6.63* |
| LOLI105/LOLI108/LOLI111/LOLI103/LOLI115 | 1.28 | 0.09 | 0.39 | 0.00 | 0.17 | 0.15 | 6.96 |
| Wild-tye check | 1.27 | 0.09 | 0.37 | 0.00 | 0.17 | 0.15 | 7.04 |
| CV | 4.4 | 42.8 | 6.3 | 0.0 | 10.6 | 11.8 | 3.1 |

B.

| GENOTYPES | C14:0 % | C16:0 % | C16:1 % | C18:0 % | C18:1 % | C18:2 % | C18:3 % | C20:0 % |
|---|---|---|---|---|---|---|---|---|
| HIOL101/HIOL109/LOLI105/LOLI108/LOLI111/LOLI103/LOLI115 | 0.06 | 3.49* | 0.34* | 1.73 | 74.94* | 14.51* | 1.33* | 0.70 |
| HIOL101/HIOL109 | 0.06 | 3.50* | 0.33* | 1.77 | 75.30* | 7.97* | 7.63* | 0.70 |
| LOLI105/LOLI108/LOLI111/LOLI103/LOLI115 | 0.07 | 3.72 | 0.32 | 1.83 | 65.82* | 23.47* | 1.37* | 0.71 |
| Wild-tye check | 0.07 | 3.76 | 0.31 | 1.89 | 64.88 | 17.07 | 8.73 | 0.72 |
| CV | 12.0 | 2.7 | 4.5 | 11.8 | 1.4 | 5.3 | 12.1 | 9.6 |

TABLE 7-continued

Levels of different fatty acids of plants comprising mutant FAD2 and mutant FAD3 alleles grown in the field at geographical region A (A) and at geographical region B (B). Plants indicated with "HIOL101/HIOL109/LOLI105/LOLI108/LOLI111/LOLI103/LOLI115" contain the two mutant FAD2 alleles and the five mutant FAD3 alleles (homozygous) as indicated. Plants indicated with "LOLI105/LOLI108/LOLI111/LOLI103/LOLI115" contain the five mutant FAD3 alleles (homozygous), but wild-type FAD2 genes; plants indicated with HIOL101/HIOL109 contain the two mutant FAD2 alleles (homozygous) but wild-type FAD3 genes. *indicates a significant difference with the wild-type check.

| GENOTYPES | C20:1 % | C20:2 % | C22:0 % | C22:1 % | C24:0 % | C24:1 % | SATS % |
|---|---|---|---|---|---|---|---|
| HIOL101/HIOL109/LOLI105/LOLI108/LOLI111/LOLI103/LOLI115 | 1.50* | 0.06 | 0.43 | 0.00 | 0.25 | 0.11 | 6.67* |
| HIOL101/HIOL109 | 1.46* | 0.05* | 0.40 | 0.00 | 0.23 | 0.12 | 6.66* |
| LOLI105/LOLI108/LOLI111/LOLI103/LOLI115 | 1.35 | 0.07 | 0.42 | 0.00 | 0.22 | 0.12 | 6.98 |
| Wild-tye check | 1.33 | 0.07 | 0.41 | 0.00 | 0.20 | 0.11 | 7.06 |
| CV | 2.4 | 6.8 | 6.7 | 346.7 | 27.9 | 17.6 | 4.6 |

TABLE 8

Agronomic performance of plants comprising mutant FAD2 and mutant FAD3 alleles grown in the field at geographical region A (A) and at geographical region B (B). Plants indicated with "HIOL101/HIOL109/LOLI105/LOLI108/LOLI111/LOLI103/LOLI115" contain the two mutant FAD2 alleles and the five mutant FAD3 alleles (homozygous) as indicated. Plants indicated with "LOLI105/LOLI108/LOLI111/LOLI103/LOLI115" contain the five mutant FAD3 alleles (homozygous), but wild-type FAD2 genes; plants indicated with HIOL101/HIOL109 contain the two mutant FAD2 alleles (homozygous) but wild-type FAD3 genes. *indicates a significant difference with the wild-type check.

A.

| GENOTYPES | ESTI (1-9) | VIG1 (1-9) | DTF days | EOF days | HICM cm | MAT (1-9) | LOM (1-9) | YLD gram | OILN % | PRON % | GLUN μmol/g |
|---|---|---|---|---|---|---|---|---|---|---|---|
| HIOL101/HIOL109/LOLI105/LOLI108/LOLI111/LOLI1103/LOLI115 | 4.9 | 4.9* | 46.8 | 67.6 | 117.6 | 5.0 | 6.0 | 1662 | 40.5 | 29.6 | 11.8 |
| HIOL101/HIOL109 | 4.8 | 5.2* | 46.9 | 67.6 | 119.6 | 5.0 | 5.8 | 1656 | 40.8 | 29.2 | 10.2 |
| LOLI105/LOLI108/LOLI111/LOLI103/LOLI115 | 5.0 | 4.9* | 46.5 | 67.2 | 115.9 | 5.1 | 6.0 | 1650 | 40.4 | 29.1 | 11.0 |
| Wild-tye check | 4.9 | 5.8 | 46.6 | 67.2 | 118.8 | 4.8 | 6.0 | 1764 | 40.2 | 29.2 | 10.8 |
| CV | 6.2 | 10.8 | 1.6 | 4.4 | 6.9 | 6.5 | 26.7 | 16.9 | 3.7 | 7.1 | 24.4 |

B.

| GENOTYPES | EST1 (1-9) | VIG1 (1-9) | DTF days | EOF days | HICM cm | DTM days | LOM (1-9) | YLD gram | OILN % | PRON % | GLUN μmol/g |
|---|---|---|---|---|---|---|---|---|---|---|---|
| HIOL101/HIOL109/LOLI105/LOLI108/LOLI111/LOLI103/LOLI115 | 8.1 | 6.9* | 40.1 | 68.4 | 98.3 | 95.1 | 8.2 | 2323 | 44.7 | 27.1 | 17.3 |
| HIOL101/HIOL109 | 8.2 | 7.3 | 40.0 | 68.5 | 98.8 | 94.7 | 8.1 | 2500 | 45.1 | 27.0 | 17.8 |
| LOLI105/LOLI108/LOLI111/LOLI103/LOLI115 | 8.0 | 6.9* | 39.8 | 68.4 | 95.8 | 95.4 | 8.3 | 2364 | 44.8 | 27.1 | 17.8 |
| Wild-tye check | 8.2 | 7.7 | 39.7 | 68.8 | 93.3 | 94.8 | 8.2 | 2420 | 44.1 | 27.6 | 17.8 |
| CV | 10.6 | 9.1 | 2.5 | 10.2 | 8.5 | 2.6 | 8.8 | 7.9 | 3.9 | 7.5 | 16.7 |

Example 7—Detection and/or Transfer of Mutant FAD2 Alleles into (Elite) *Brassica* Lines The mutant FAD2 genes are transferred into (elite) *Brassica* breeding lines by the following method: A plant containing a mutant FAD2 gene (donor plant), is crossed with an (elite) *Brassica* line (elite parent/recurrent parent) or variety lacking the mutant FAD2 gene. The following introgression scheme is used (the mutant FAD2 allele is abbreviated to fad2 while the wild type is depicted as FAD2):

BC1 cross: fad2/fad2 (donor plant) X FAD2/FAD2 (elite parent)

F1 plant: FAD2/fad2

BC2 cross: FAD2/fad2 X FAD2/FAD2 (recurrent parent)

BC2 plants: 50% FAD2/fad2 and 50% FAD2/FAD2

The 50% FAD2/fad2 are selected using molecular markers (e.g. AFLP, PCR, Invader™, TaqMan®, KASP assay, and the like; see also below) for the mutant FAD2 allele (fad2).

BC3 cross: FAD2/fad2 (13C1 plant) X FAD2/FAD2 (recurrent parent)

BC3 plants: 50% FAD2/fad2 and 50% FAD2/FAD2

The 50% FAD2/fad2 are selected using molecular markers for the mutant FAD2 allele (fad2).

Backcrossing is repeated until BC4 to BC7.

BC4-7 plants: 50% FAD2/fad2 and 50% FAD2/FAD2

The 50% FAD2/fad2 are selected using molecular markers for the mutant FAD2 allele (fad2). To reduce the number of backcrossings (e.g. until BC4 instead of BC7), molecular markers can be used specific for the genetic background of the elite parent.

BC4-7 S1 cross: FAD2/fad2 X FAD2/fad2

BC4-7 S1 plants: 25% FAD2/FAD2 and 50% FAD2/fad2 and 25% fad2/fad2

Plants containing fad2 are selected using molecular markers for the mutant FAD2 allele (fad2). Individual BC4-7 S1 or BC4-7 S2 plants that are homozygous for the mutant FAD2 allele (fad2/fad2) are selected using molecular markers for the mutant and the wild-type FAD2 alleles. These plants are then used for seed production.

To select for plants comprising a point mutation in a FAD2 allele, direct sequencing by standard sequencing techniques known in the art can be used.

Alternatively, Invader™ technology (Third Wave Agbio) can be used to discriminate plants comprising a specific point mutation in an FAD2 allele from plants not comprising that specific point mutation. Discriminating Invader® probes are thus developed to detect the presence or absence and the zygosity status of mutant alleles identified in Example 3, based on the single nucleotide difference between the mutant and wildtype allele. Briefly, probes specific for the mutant or corresponding wild-type target FAD2 gene and "invading" probes which can be used in combination with them are developed. Generally, each probe set consists of one probe specific for the mutant or the wild type target gene of which the first nucleotide after the "5' flap" sequence matches with the nucleotide difference (the so-called "primary probe") and one probe specific for the nucleotides upstream of the nucleotide difference (the so-called "Invader® oligo"). The last nucleotide of the latter primer may match with the nucleotide difference in the mutant, but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio). The Invader® assay procedure and interpretation of the data are performed as prescribed by the manufacturer (Third Wave Agbio). Briefly, 5' "flap" nucleotide sequences (flap1 for the mutant allele and flap2 for the wild-type allele) are cleaved from the primary probes in the primary phase of the Invader™ assay and are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target FAD2 gene, respectively.

Alternatively, KASP assays (KBioscience) can be used to discriminate plants comprising a specific point mutation in an FAD2 allele from plants not comprising that specific point mutation. Discriminating primers were developed to detect the presence or absence and the zygosity status of mutant alleles identified in Example 3.

Briefly, forward primers specific for the mutant or corresponding wild-type target FAD2 gene and a reverse primer that can be used in combination with them were developed. The nucleotide at the 3' end of the forward primers corresponds to the nucleotide which differs between the mutant and the corresponding wild-type allele. The primers can be used in combination with fluorescent dyes, such as FAM and VIC according to the protocol as described by the manufacturer (KBioscience).

Primers to detect the presence or absence and the zygosity status of the mutant FAD2 alleles are shown in Table 9.

TABLE 9

Forward (Fw) and reverse (Rv) primers to detect mutant FAD2 alleles and the corresponding wild-type alleles.
FAM probe: wild-type allele, VIC probe: mutant allele

| Name | | Primer | SEQ ID |
|---|---|---|---|
| HIOL101 | Fw FAM | GAAGGTGACCAAGTTCATGCTGTAGTCGCTGAAGGCGTGGTG | 28 |
| | Fw VIC | GAAGGTCGGAGTCAACGGATTGTAGTCGCTGAAGGCGTGGTA | 29 |
| | Rv | TCTCTACTGGGCCTGCCAG | 30 |
| HIOL103 | Fw FAM | GAAGGTGACCAAGTTCATGCTCGCACTCGTGGGCTATGACC | 31 |
| | Fw VIC | GAAGGTCGGAGTCAACGGATTCCGCACTCGTGGGCTATGACT | 32 |
| | Rv | TCTACTGGGCCTGCCAAGGG | 33 |
| HIOL109 | Fw FAM | GAAGGTGACCAAGTTCATGCTGTCCAGTTCACGCTCGGCTG | 37 |
| | Fw VIC | GAAGGTCGGAGTCAACGGATTCGTCCAGTTCACGCTCGGCTA | 38 |
| | Rv | CCGTCGCTGTAAGGTCTTCCA | 39 |

The invention claimed is:

1. A *Brassica napus* plant, cell, seed or progeny of said plant, comprising a BnFAD2-A1, a BnFAD2-A2, a BnFAD2-C1 and a BnFAD2-C2 gene, wherein said plant comprises knock-out fad2 alleles of the BnFAD2-A1 and of the BnFAD2-C2 genes, and wherein the fad2 alleles of said BnFAD2-C1 gene encode a functional BnFAD2-C1 protein.

2. The *Brassica napus* plant, cell, seed or progeny of said plant, according to claim 1, wherein the fad2 alleles of said BnFAD2-C1 gene are wild-type alleles.

3. The *Brassica napus* plant, cell, seed or progeny of said plant, according to claim 2, wherein the fad2 alleles of the BnFAD2-A2 gene are knock-out fad2 alleles.

4. The *Brassica napus* plant, cell, seed or progeny of said plant, according to claim 1, wherein said knock-out fad2 allele of said BnFAD2-A1 gene is a fad2 allele encoding a protein in which the His at position 109 of SEQ ID NO: 6 is substituted with another amino acid, and wherein said knock-out fad2 allele of said BnFAD2-C2 allele is a fad2 allele comprising a stop codon mutation in the codon encoding the Trp at position 190 of SEQ ID NO: 15.

5. The *Brassica napus* plant, cell, seed or progeny of said plant, according to claim 4, which is derived or obtained from:
   a. seed comprising HIOL101 having been deposited at NCIMB under accession number NCIMB 42376; and
   b. seed comprising HIOL109 having been deposited at NCIMB under accession number NCIMB 42375.

6. The *Brassica napus* plant, cell, seed or progeny of said plant, according to claim 1 which is homozygous for any one of the knock-out fad2 alleles.

7. The *Brassica napus* plant, cell, seed or progeny of said plant, according to claim 1, said plant further comprising at least a knock-out fad3 allele of at least one *Brassica napus* FAD3 gene.

8. The *Brassica napus* plant, cell, seed or progeny of said plant, according to claim 7, said plant further comprising knock-out fad3 alleles of *Brassica napus* FAD3 genes FAD3-A1, FAD3-A2, FAD3-A3, FAD3-C1 and FAD3-C2.

9. The *Brassica napus* plant, cell, seed or progeny of said plant, according to claim 7, wherein said at least one *Brassica napus* FAD3 gene is:
   a. a FAD3-A1 gene comprising a sequence having at least 90% sequence identity to the sequence of SEQ ID NO: 37, or having a cDNA sequence having at least 90% sequence identity to the sequence of SEQ ID NO: 39, or encoding a protein having at least 90% sequence identity to the sequence of SEQ ID NO: 38;
   b. a FAD3-A2 gene comprising a sequence having at least 90% sequence identity to the sequence of SEQ ID NO: 40, or having a cDNA sequence having at least 90% sequence identity to the sequence of SEQ ID NO: 42, or encoding a protein having at least 90% sequence identity to the sequence of SEQ ID NO: 41;
   c. a FAD3-A3 gene comprising a sequence having at least 90% sequence identity to the sequence of SEQ ID NO: 43, or having a cDNA sequence having at least 90% sequence identity to the sequence of SEQ ID NO: 45, or encoding a protein having at least 90% sequence identity to the sequence of SEQ ID NO: 44;
   d. a FAD3-C1 gene comprising a sequence having at least 90% sequence identity to the sequence of SEQ ID NO: 46, or having a cDNA sequence having at least 90% sequence identity to the sequence of SEQ ID NO: 48, or encoding a protein having at least 90% sequence identity to the sequence of SEQ ID NO: 47; or
   e. a FAD3-C2 gene comprising a sequence having at least 90% sequence identity to the sequence of SEQ ID NO: 49, or having a cDNA sequence having at least 90% sequence identity to the sequence of SEQ ID NO: 51, or encoding a protein having at least 90% sequence identity to the sequence of SEQ ID NO: 50.

10. The *Brassica napus* plant, cell, seed or progeny of said plant, according to claim 1, which has increased levels of C18:1 in the seed oil and which maintains normal agronomic development when compared to a control plant.

11. The *Brassica napus* plant, cell, seed or progeny of said plant, according to claim 7, which has increased levels of C18:1 and decreased levels of C18:3 in the seed oil when compared to a control plant.

12. A method for increasing the levels of C18:1 in seed oil while maintaining normal agronomic development, said method comprising introducing a knock-out fad2 allele of a BnFAD2-A1 gene and a knock-out fad2 allele of a BnFAD2-C2 gene into a *Brassica napus* plant, and selecting a *Brassica napus* plant comprising said knock-out fad2 allele of said BnFAD2-A1 gene, and said knock-out fad2 allele of said BnFAD2-C2 gene, and wherein said plant further contains a BnFAD2-C1 gene of which the fad2 alleles of said BnFAD2-C1 gene encode a functional BnFAD2-C1 protein, thereby increasing the levels of C18:1 in seed oil while maintaining normal agronomic development in a *Brassica napus* plant when compared to a control plant.

13. The method according to claim 12 for increasing the levels of C18:1 and decreasing the levels of C18:3 in seed oil while maintaining normal agronomic development, said method further comprising introducing a knock-out fad3 allele of a FAD3-A1 gene, a knock-out fad3 allele of a FAD3-A2 gene, a knock-out fad3 allele of a FAD3-A3 gene, a knock-out fad3 allele of a FAD3-C1 gene, and a knock-out fad3 allele of a FAD3-C2 gene, into a *Brassica napus* plant, and selecting a *Brassica napus* plant comprising said knock-out fad3 allele of said FAD3-A1 gene, said knock-out fad3 allele of said FAD3-A2 gene, said knock-out fad3 allele of said FAD3-A3 gene, said knock-out fad3 allele of said FAD3-C1 gene, and said knock-out fad3 allele of said FAD3-C2 gene, thereby increasing the levels of C18:1 and decreasing the levels of C18:3 in seed oil while maintaining normal agronomic development in a *Brassica napus* plant when compared to a control plant.

14. A method for producing oil, comprising harvesting the seed according to claim 1 and extracting the oil from said seed.

15. A method of producing food, feed, or an industrial product comprising preparing the food, feed or industrial product from the plant, cell, seed or progeny of said plant according to claim 1.

16. A method to produce a *Brassica napus* plant comprising an increased level of C18:1 in the seed oil and which maintains normal agronomic development compared to a control plant, said method comprising sowing seeds according to claim 1 and growing plants from said seeds.

* * * * *